United States Patent
Yoshida et al.

(10) Patent No.: US 7,982,044 B2
(45) Date of Patent: *Jul. 19, 2011

(54) IMINOPYRIDINE DERIVATIVES AND USE THEREOF

(75) Inventors: Masato Yoshida, Osaka (JP); Nobuki Sakauchi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/022,563

(22) Filed: Feb. 7, 2011

(65) Prior Publication Data

US 2011/0124876 A1  May 26, 2011

Related U.S. Application Data

(63) Continuation of application No. 12/900,045, filed on Oct. 7, 2010, which is a continuation-in-part of application No. 12/428,368, filed on Apr. 22, 2009.

(30) Foreign Application Priority Data

Apr. 23, 2008 (JP) .................................. 2008-113135

(51) Int. Cl.
C07D 213/82 (2006.01)

(52) U.S. Cl. ...................................................... 546/309
(58) Field of Classification Search .................... None
See application file for complete search history.

(56) References Cited

U.S. PATENT DOCUMENTS

| | | | |
|---|---|---|---|
| 3,997,666 A | 12/1976 | Witte et al. | |
| 4,699,918 A | 10/1987 | Maillard et al. | |
| 5,250,498 A | 10/1993 | Andree et al. | |
| 6,488,922 B1 | 12/2002 | Damm et al. | |
| 7,288,549 B2 | 10/2007 | Aszodi et al. | |
| 2009/0105239 A1 | 4/2009 | Brimert et al. | |
| 2009/0270393 A1 | 10/2009 | Yoshida et al. | |
| 2010/0016315 A1 | 1/2010 | Yoshida et al. | |
| 2011/0034464 A1 | 2/2011 | Yoshida et al. | |
| 2011/0039846 A1 | 2/2011 | Yoshida et al. | |
| 2011/0039892 A1 | 2/2011 | Yoshida et al. | |

FOREIGN PATENT DOCUMENTS

| | | |
|---|---|---|
| AR | 071392 | 6/2010 |
| AU | 2009238938 | 4/2009 |
| BD | 101/2009 | 4/2009 |
| BR | PI 0910737-1 | 4/2009 |
| CA | 2723216 | 4/2009 |
| CL | 964-2009 | 3/2010 |
| CN | 200980123875.8 | 4/2009 |
| CO | 10.145.079 | 4/2009 |
| CR | 11765 | 4/2009 |
| DE | 106 377 | 6/1973 |
| DE | 263 759 A1 | 4/1986 |
| DO | P2010-0321 | 11/2010 |
| DZ | 100716 | 4/2009 |
| EA | 201071229 | 4/2009 |
| EC | SP-10-10626 | 4/2009 |
| EG | PCT1750/2010 | 4/2009 |
| EP | 0 047 977 A2 | 3/1982 |
| EP | 432600 A1 | 6/1991 |
| EP | 2771624 | 1/2011 |
| GC | 13335 | 4/2009 |
| GE | AP 2009 012013 | 4/2009 |
| ID | W00201003644 | 4/2009 |
| IL | 208771 | 4/2009 |
| IN | 7546/DELNP/2010 | 4/2009 |
| JO | 146/2009 | 4/2009 |
| JP | 48-40544 | 12/1973 |
| JP | 8-208614 | 8/1996 |
| JP | 2002-503724 | 2/2002 |
| JP | 2008/113135 | 4/2008 |
| JP | 2010-541619 | 4/2009 |
| KE | P/2010/001170 | 4/2009 |
| KR | 2010-130235 | 12/2010 |
| LB | 8596 | 8/2010 |
| MA | PV/33353 | 4/2009 |
| MX | A/2010/011652 | 4/2009 |
| MY | PI2010004943 | 4/2009 |

(Continued)

OTHER PUBLICATIONS

Goetz et al., "BMY 7378 is a selective antagonist of the D subtype of α1-adrenoceptors." European Journal of Pharmacology, 272, pp. R5-R6 (1995).

Indra et al., "(±)-Domesticine, a novel and selective α1D-adrenoceptor antagonist in animal tissues and human α1-adrenoceptors." European Journal of Pharmacology 445, pp. 21-29, (2002).

Elassar, "A Facile and Efficient Synthesis of Bisazine Derivatives." Heteroatom Chemistry, vol. 15, No. 4, pp. 293-299 (2004).

Rampa et al., "Structure-Activity Relationship Studies in the Field of Calcium Antagonists: Xanthome 1,4-dihydropyridines bearing a 2,3-lactone ring." Arzeim-Forsch./Drug Res. 45 (II), No. 9, pp. 957-962 (1995).

(Continued)

*Primary Examiner* — Zinna Northington Davis
(74) *Attorney, Agent, or Firm* — Sughrue Mion, PLLC

(57) ABSTRACT

The present invention aims to provide an iminopyridine derivative compound having an $\alpha_{1D}$ adrenergic receptor antagonistic action, which is useful as an agent for the prophylaxis or treatment of a lower urinary tract disease and the like. The present invention provides a compound represented by the formula

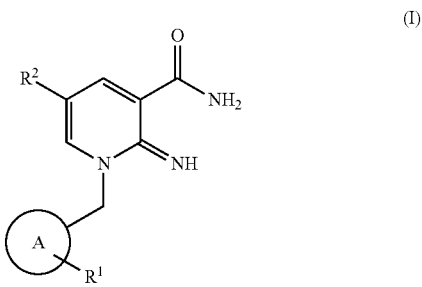

(I)

wherein each symbol is as defined in the specification, or a salt thereof.

1 Claim, No Drawings

FOREIGN PATENT DOCUMENTS

| | | |
|---|---|---|
| NG | C/2010/796 | 4/2009 |
| NZ | 588909 | 4/2009 |
| PE | 000559-2009/DIN | 12/2009 |
| PH | 1-2010-502392 | 4/2009 |
| PK | 346/2009 | 4/2009 |
| SG | 165762 | 11/2010 |
| TH | 0901001782 | 4/2009 |
| TN | 2010/0451 | 4/2009 |
| TW | 200948784 | 12/2009 |
| UA | A2010 13899 | 4/2009 |
| UY | 31.781 | 4/2009 |
| VE | 2009-000731 | 4/2009 |
| VN | 1-2010-03138 | 4/2009 |
| WO | 00/04012 A1 | 1/2000 |
| WO | 00/04027 A1 | 1/2000 |
| WO | 00/19969 A1 | 4/2000 |
| WO | 02/32872 | 4/2002 |
| WO | 2005/026124 A1 | 3/2005 |
| WO | 2008/050732 A1 | 5/2008 |
| WO | 2009/131135 A1 | 10/2009 |
| WO | 2009/131245 | 10/2009 |
| ZA | 2010/07643 | 4/2009 |

OTHER PUBLICATIONS

Mohareb et al., "Heterocyclic Synthesis with Enamines: Convenient Syntheses of Polyfunctionally Substituted Pyrazole, Pyridine, Pyrimidine and Pyrazolo [3,4-*d*]pyrimidine Derivatives." Journal of the Chinese Chemical Society, 40, pp. 181-187 (1993).

Pluske et al., "Δα, β-Butenolides. XII. Syntheses based on 2,4-pentadienoic acid derivatives", Latvijas PSR Zinatnu Akademijas Vestis, Kimijas Serija, 4:471-478 (1986).

Pluske et al., "Δα, β-Butenolides. X. Reactions of halobutenolides with aliphatic amines", Latvijas PSR Zinatnu Akademijas Vestis, Kimijas Serija, 3:351-358, 1985.

Pluske et al., "Δα, β-Butenolides. IX, Derivatives of muconic acid and synthesis from them", Latvijas PSR Zinatnu Akademijas Vestis, Kimijas Serija, No. 2, pp. 200-205, 1985.

Karklina et al., "Butenolides, 21. Synthesis of N- and O-heterocycles based on 2,4-pentadienoic acid derivatives", Latvijas PSR Zinatnu Akademijas Vestis, Kimijas Serija, Zurnals, No. 3-4, pp. 109-113 (1995).

Moracci et al. "Covalent Adducts From 1,3-Disubstituted Pyridinium Salts and Piperidine." Tetrahedon vol. 36, pp. 785-789 (1980).

Moracci et al., "Reactivity of Pseudobases from Pyridinium Salts Competition Between Hydrogen Transfer and Ring-Opening Reactions." Tetrahedon, vol. 35, pp. 2591-2593 (1979).

Franke et al., "Reactivity of methoxybutenone" Fette, Seifen, Anstrichmittel, 82, No. 2, pp. 82-86 (1980).

Moracci et al. "Reactivity of 3-Cyano-1-Methylpyridinium Iodide in Aqueous Ammonia or Amine Solutions." Tetrahedon, vol. 35, pp. 809-812, 1979.

Hong et al., "Syntheses of 2-Oxo- and 2-Imino-1,2-dihydropyridines by Cobalt-catalyzed Cyclocotrimerization of Acetylenes with Isocyanates and Carbodiimides," The Institute of Physical and Chemical Research (Japan). Nihon Kagaku Kaishi, No. 5, pp. 730-736 (1978).

Hong et al., "Syntheses of 2-Oxo- and 2-Imino-1,2-Dihdropyridines by Cobalt-catalyzed Cyclocotrimerization of Acetylenes with Isocyanates and Carbodiimides." Tetrahedon Letters No. 15, pp. 1333-1336 (1977).

Liebscher et al., "Chemistry of activated vinyl halides. Synthesis and reaction behavior of 3-(β-chlorovinyl)acrylonitriles", Journal für Praktische Chemie, Band, 318, No. 5, pp. 705-730 (1976).

Liebscher et al., "Heterocyclic dyes and precursors. 24. Simple pathway to 2-aminothiapyrylium and -pyridinium salts", Zeitschrift fuer Chemie, 13 (9), pp. 342-343 (1973).

Blanch et al., "Formation of 2-Methylaminopyridine-3-carbaldehyde and the Corresponding Methylimine by Ring-opening and Ring-closing Reactions of 3-Cyano-1-methylpyridinium Iodide in N-Sodium Hydroxide." J. Chem. Soc (C), pp. 1892-1895 (1971).

Gompper et al., "Cycloaddition to Diethyl 2,4-Bis(diethylamino)cyclobutadiene-1,3-dicarboxylate", Angewandte Chemie, International Edition, vol. 10, No. 1, pp. 68-70 (1971).

Adachi, "Isoxazoles. XXI. Ring Conversion Reactions of 2,3,4-Trisubstituted Isoxazolium Salts with Some Nucleophiles." Chem. Pharm. Bull., vol. 17, No. 11, pp. 2209-2216 (1969).

Hirai, "The Behavior of 4-Amino-5-carboxy-2-methylpyrimidine in Aqueous Solution." Chem. Pharm. Bull. vol. 14, No. 8, pp. 861-865 (1966).

Kondakova et al., "Action of alkyl halides on α- and α'-aminonicotines", Doklady Akademii Nauk SSSR vol. 66, pp. 647-650 (1949).

Belyakov et al., Zhurnal Strukturnoi Khimi.. vol. 29, No. 5, pp. 169-172 (1988). Abstract at p. 8 of STN Search Result, AN 1989:67326 ZCAPLUS.

Guendel, "Studies on quaternary pyridinim salts. X. A condensation reaction of 3-cyanopyridinium salts on addition of alkoxides", Zeitschrift Fuer Natuforschung, Teil B: Anorganische Chemie, Organische Chemie. vol. 35B, No. 4, pp. 490-493 (1980).

Mumm et al., "Pyridone methide", Ann., 443, pp. 272-309 (1925).

Ruan, "Effects of Cl-channel blockers on $Ca^{2+}$ influx induced by α1-adrenoceptor sybtypes", Chinese Pharmacological Bulletin, 17(2):147-150 (2001).

Széll et al., "Smooth muscle and parasympathetic nerve terminals in the rat urinary bladder have different subtypes of α1 adrenoceptors", British Journal of Pharmacology, 130(7):1685-1691 (2000).

International Search Report for PCT/JP2007/070581 mailed Dec. 25, 2007.

International Search Report for PCT/JP2009/058434 mailed Jul. 16, 2009.

Beheshita et al., "DABCO as an efficient catalyst for the synthesis of 3-cyano-2(1*H*)-pyridinones and their 2-imino analogues" European Journal Chemistry, 1(3):232-235 (2010).

Non-Final Office Action for U.S. Appl. No. 12/428,368 mail date Mar. 11, 2011.

Non-Final Office Action for U.S. Appl. No. 12/900,045 mail date Mar. 11, 2011.

Non-Final Office Action for U.S. Appl. No. 13/022,537 mail date Mar. 14, 2011.

Response under 37 C.F.R. § 1.111 for U.S. Appl. No. 13/022,537, filed Apr. 1, 2011.

Notice of Allowance for U.S. Appl. No. 13/022,537 mail date Apr. 20, 2011.

Non-Final Office Action for U.S. Appl. No. 13/022,556 mail date Mar. 10, 2011.

Response under 37 C.F.R. § 1.111 for U.S. Appl. No. 13/022,556, filed Apr. 1, 2011.

Notice of Allowance for U.S. Appl. No. 13/022,556 mail date Apr. 18, 2011.

SEQUENCE LISTING

```
<160> NUMBER OF SEQ ID NOS: 2

<210> SEQ ID NO 1
<211> LENGTH: 45
<212> TYPE: DNA
<213> ORGANISM: Artificial Sequence
<220> FEATURE:
<223> OTHER INFORMATION: Primer for cloning human alpha1D adrenaline
``` receptor gene

<400> SEQUENCE: 1
ccgacggccg ctagcgagat gactttccgc gatctcctga gcgtc              45

<210> SEQ ID NO 2
<211> LENGTH: 38
<212> TYPE: DNA
<213> ORGANISM: Artificial Sequence
<220> FEATURE:
<223> OTHER INFORMATION: Primer for cloning human alpha1D adrenaline
      receptor gene

<400> SEQUENCE: 2
gctctgggta ccttaaatat cggtctcccg taggttgc                      38

IMINOPYRIDINE DERIVATIVES AND USE THEREOF

CROSS-REFERENCE TO RELATED APPLICATIONS

This application is a Continuation of U.S. application Ser. No. 12/900,045, filed Oct. 7, 2010; which is a Continuation-In-Part of U.S. application Ser. No. 12/428,368, filed Apr. 22, 2009; which claims priority to Japan Application No. 113135/2008, filed Apr. 23, 2008; the entire disclosure of each of which is incorporated herein by reference.

SEQUENCE LISTING

This application contains a Sequence Listing. The entire contends of the ASCII text file, file name Q122348SequenceListing_ST25.txt, created Dec. 20, 2010 (file size: 801 Bytes), is incorporated-herein-by-reference.

TECHNICAL FIELD

The present invention relates to an iminopyridine derivative having a superior selective $\alpha_{1D}$ adrenergic receptor (hereinafter to be simply also referred to as an $\alpha_{1D}$ receptor) antagonistic action and useful as an agent for the prophylaxis or treatment of a lower urinary tract disease and the like, and a screening method for a compound having an $\alpha_{1D}$ adrenergic receptor antagonistic action.

BACKGROUND OF THE INVENTION $\alpha_1$ Adrenergic receptors are widely distributed in the cardiovascular system, lower urinary tracts and the like, and involved in sympathetic nerve response activities. Since the relationship with pathologies such as hypertension, cardiac hypertrophy and dysuria has been suggested, $\alpha_1$ receptors have attracted attention for some time, and many attempts have been made to develop therapeutic drugs. In recent years, it has been clarified that $\alpha_1$ blockers are effective for dysuria associated with benign prostatic hypertrophy (BPH). Coupled with the marketability thereof, extensive interests have been created again (non-patent document 1).

The $\alpha_1$ receptor gene was cloned from the late 1980s to the early 1990s, and the presence of three subtypes of $\alpha_{1A}$, $\alpha_{1B}$ and $\alpha_{1D}$ has been clarified. Among these, $\alpha_{1D}$ receptor has been confirmed to express in a number of tissues such as blood vessel, brain, spinal cord, gastrointestinal tract, bladder, kidney and the like. While the physiological function of $\alpha_{1D}$ receptor has not been elucidated, $\alpha_{1D}$ receptor antagonists may provide therapeutic drugs for various diseases since they are localized widely.

A greater distribution of $\alpha_{1D}$ receptors in the bladder, parasympathetic nerve nucleus of the sacral cord, and the like as compared to other subtypes has been confirmed (non-patent documents 2, 3), thus suggesting strong involvement in urine storage. In fact, there is a report on a significant increase in the bladder capacity and the single voided volume in $\alpha_{1D}$ knockout mouse (non-patent document 4). Recent reports have documented that the expression amount of $\alpha_{1D}$ receptor mRNA increases in the bladder of BPH patients and BPH model animal (non-patent documents 5 and 6), the bladder muscle isolated from BPH patients may show a promoted contractile function via $\alpha_{1D}$ receptor (non-patent document 7) and the like, thus suggesting a possible involvement of an $\alpha_{1D}$ receptor expressed in the bladder in the pathology of BPH. From the foregoing, an $\alpha_{1D}$ receptor antagonist is promising as an agent for the prophylaxis or treatment of a lower urinary tract disease and the like.

As examples of the compound showing an $\alpha_{1D}$ receptor antagonistic action, non-patent document 8 describes a compound represented by the formula

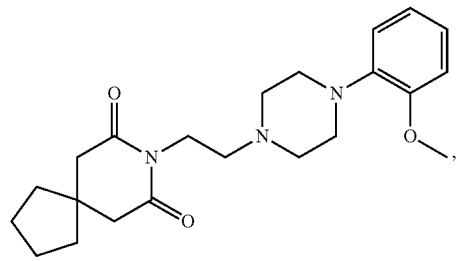

patent document 1 describes a compound represented by the formula

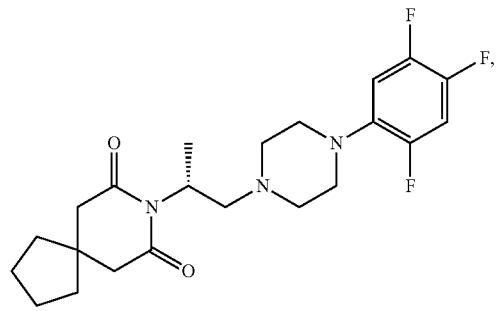

patent document 2 describes a compound represented by the formula

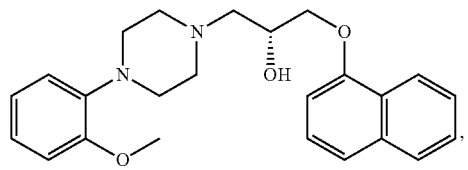

patent document 3 describes a compound represented by the formula

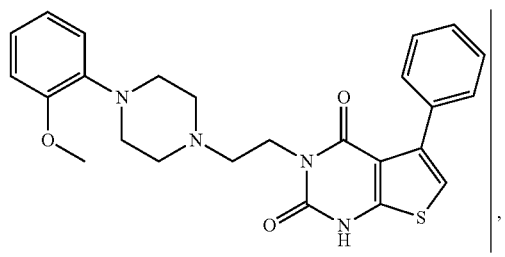

and non-patent document 9 describes a compound represented by the formula
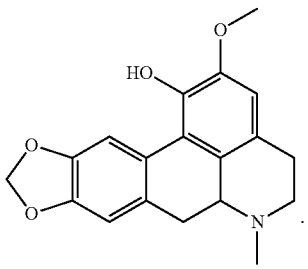
In addition, as iminopyridine derivatives, those described in patent documents 4 to 7 and non-patent documents 10 to 32 are known.
Patent document 8 describes compounds represented by the formulas
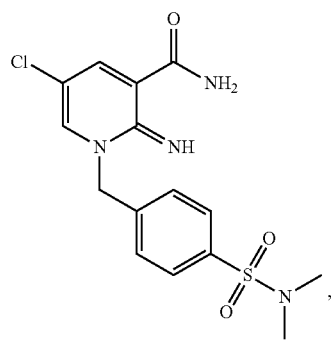
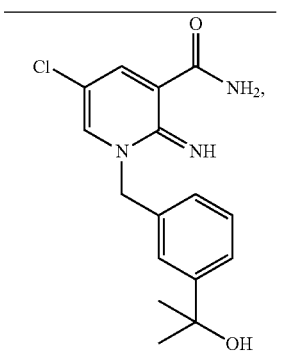
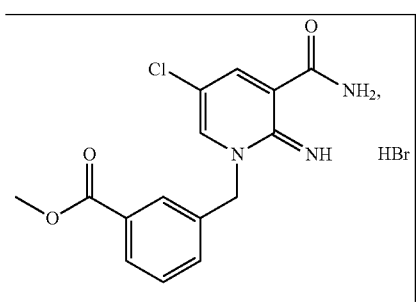
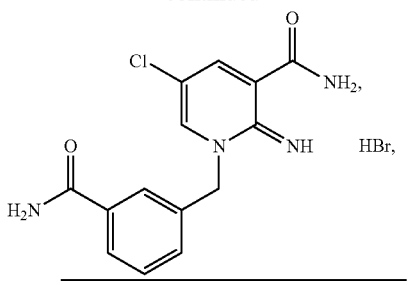
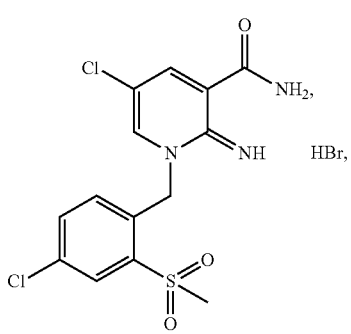
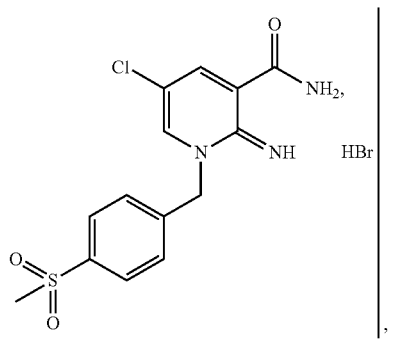
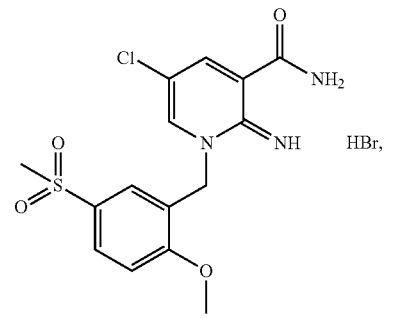
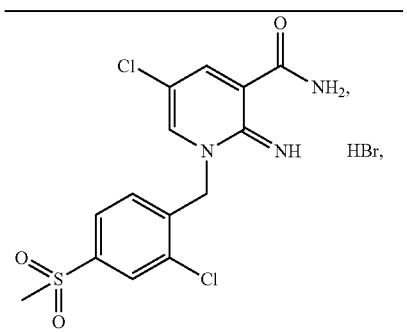

-continued

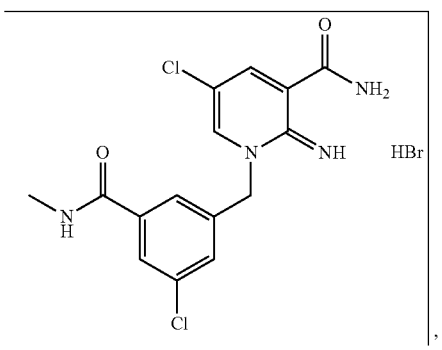

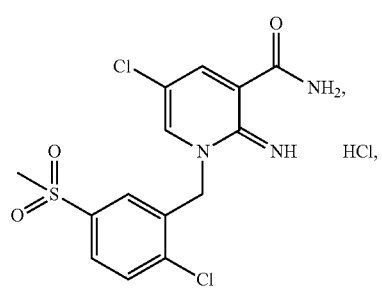

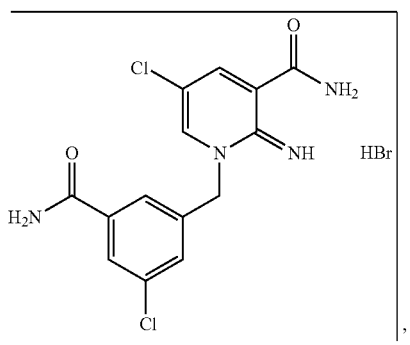

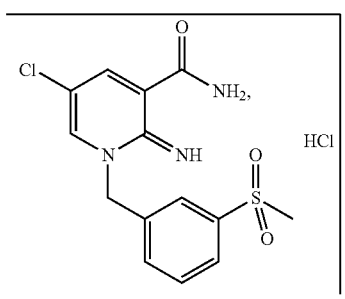

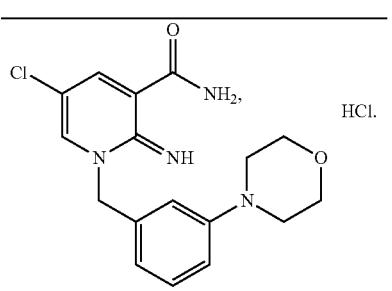

CITATION LIST

Patent Literature patent document 1: WO00/04012
patent document 2: U.S. Pat. No. 3,997,666
patent document 3: WO00/04027
patent document 4: DD 263759
patent document 5: EP47977
patent document 6: DD106377
patent document 7: JP-B-48-40544
patent document 8: WO08/050732

Non-Patent Literature non-patent document 1: Yakugaku Zasshi 126, 187-198, 2006
non-patent document 2: Molecular Brain Research 63, 254-261, 1999
non-patent document 3: J. Urol. 160: 937-943., 1998
non-patent document 4: J. Urol. 174: 370-4., 2005
non-patent document 5: J. Urol. 170: 649-653., 2003
non-patent document 6: J. Urol. 167: 1513-1521., 2002
non-patent document 7: J. Urol. 173: 657-61., 2005
non-patent document 8: Eur. J. Pharmacol., 272, (1995), R5-R6
non-patent document 9: Eur. J. Pharmacol., 445, (2002), 21-29
non-patent document 10: Heteroatom Chemistry (2004), 15(4), 293-299
non-patent document 11: Latvijas Kimijas Zurnals (1995), (3-4), 109-113
non-patent document 12: Arzneimittel-Forschung (1995), 45(9), 957-62
non-patent document 13: Journal of the Chinese Chemical Society (Taipei, Taiwan) (1993), 40(2), 181-7
non-patent document 14: Zhurnal Strukturnoi Khimii (1988), 29(5), 169-72
non-patent document 15: Latvijas PSR Zinatnu Akademijas Vestis, Kimijas Serija (1986), (4), 471-8
non-patent document 16: Latvijas PSR Zinatnu Akademijas Vestis, Kimijas Serija (1985), (3), 351-8
non-patent document 17: Latvijas PSR Zinatnu Akademijas Vestis, Kimijas Serija (1985), (2), 200-5
non-patent document 18: Tetrahedron (1980), 36(6), 785-9
non-patent document 19: Zeitschrift fuer Naturforschung, Teil B: Anorganische Chemie, Organische Chemie (1980), 35B(4), 490-3
non-patent document 20: Tetrahedron (1979), 35(21), 2591-3
non-patent document 21: Fette, Seifen, Anstrichmittel (1980), 82(2), 82-6
non-patent document 22: Tetrahedron (1979), 35(6), 809-12
non-patent document 23: Journal of Chemical Society of Japan (1978), (5), 730-6
non-patent document 24: Tetrahedron Letters (1977), (15), 1333-6
non-patent document 25: Journal fuer Praktische Chemie (Leipzig) (1976), 318(5), 705-30
non-patent document 26: Zeitschrift fuer Chemie (1973), 13(9), 342-3
non-patent document 27: Journal of Chemical Society [Section] C: Organic (1971), (10), 1892-5
non-patent document 28: Angewandte Chemie, International Edition in English (1971), 10(1), 68-70
non-patent document 29: Chemical & Pharmaceutical Bulletin (1969), 17(11), 2209-16
non-patent document 30: Chemical & Pharmaceutical Bulletin (1966), 14(8), 861-6
non-patent document 31: Doklady Akademii Nauk SSSR (1949), 66, 647-50
non-patent document 32: Ann. (1925), 443, 272-309

SUMMARY OF THE INVENTION

The present invention aims to provide a compound useful as an agent for the prophylaxis or treatment of a lower urinary tract disease and the like.

The present inventors have conducted intensive studies in view of the above-mentioned situation and found that a compound represented by the formula

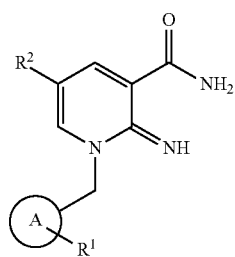

(I)

wherein
ring A- is an aromatic ring group having at least one substituent $R^1$ and optionally further having substituent(s),
$R^1$ is a group selected from
(1) a group represented by the formula —S(O)$_n$R$^3$ wherein $R^3$ is a hydrogen atom, a hydrocarbon group optionally having substituent(s) or an amino group optionally having substituent(s), and n is an integer of 0 to 2,
(2) a non-aromatic nitrogen-containing heterocyclic group optionally having substituent(s),
(3) a carbamoyl group optionally having substituent(s),
(4) an amino group substituted by carbamoyl optionally having substituent(s),
(5) an alkoxycarbonyl group, and
(6) an alkyl group substituted by hydroxy, and
$R^2$ is a hydrogen atom, a halogen atom, a cyano group, a hydrocarbon group optionally having substituent(s), an acyl group, a heterocyclic group optionally having substituent(s), an amino group optionally having substituent(s), a hydroxy group optionally having a substituent, or a mercapto group optionally having a substituent (hereinafter to be abbreviated as compound (I)), or a salt thereof has an $\alpha_{1D}$ adrenergic receptor antagonistic action based on its specific chemical structure. Based on the finding, they have completed the present invention.

Accordingly, the present invention relates to
[1] a compound represented by the formula

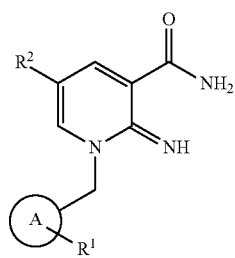

(I)

wherein
ring A- is an aromatic ring group having at least one substituent $R^1$ and optionally further having substituent(s),
$R^1$ is a group selected from
(1) a group represented by the formula —S(O)$_n$R$^3$ wherein $R^3$ is a hydrogen atom, a hydrocarbon group optionally having substituent(s) or an amino group optionally having substituent(s), and n is an integer of 0 to 2,
(2) a non-aromatic nitrogen-containing heterocyclic group optionally having substituent(s),
(3) a carbamoyl group optionally having substituent(s),
(4) an amino group substituted by carbamoyl optionally having substituent(s),
(5) an alkoxycarbonyl group, and
(6) an alkyl group substituted by hydroxy, and
$R^2$ is a hydrogen atom, a halogen atom, a cyano group, a hydrocarbon group optionally having substituent(s), an acyl group, a heterocyclic group optionally having substituent(s), an amino group optionally having substituent(s), a hydroxy group optionally having a substituent, or a mercapto group optionally having a substituent,
provided that
5-chloro-1-{4-[(dimethylamino)sulfonyl]benzyl}-2-imino-1,2-dihydropyridine-3-carboxamide,
5-chloro-1-[3-(1-hydroxy-1-methylethyl)benzyl]-2-imino-1,2-dihydropyridine-3-carboxamide,
methyl 3-{[3-(aminocarbonyl)-5-chloro-2-iminopyridin-1 (2H)-yl]methyl}benzoate,
1-[3-(aminocarbonyl)benzyl]-5-chloro-2-imino-1,2-dihydropyridine-3-carboxamide,
5-chloro-1-[4-chloro-2-(methylsulfonyl)benzyl]-2-imino-1,2-dihydropyridine-3-carboxamide,
5-chloro-2-imino-1-[4-(methylsulfonyl)benzyl]-1,2-dihydropyridine-3-carboxamide,
5-chloro-2-imino-1-[2-methoxy-5-(methylsulfonyl)benzyl]-1,2-dihydropyridine-3-carboxamide,
5-chloro-1-[2-chloro-4-(methylsulfonyl)benzyl]-2-imino-1,2-dihydropyridine-3-carboxamide,
5-chloro-1-{3-chloro-5-[(methylamino)carbonyl]benzyl}-2-imino-1,2-dihydropyridine-3-carboxamide,
5-chloro-1-[2-chloro-5-(methylsulfonyl)benzyl]-2-imino-1,2-dihydropyridine-3-carboxamide,
1-[3-(aminocarbonyl)-5-chlorobenzyl]-5-chloro-2-imino-1,2-dihydropyridine-3-carboxamide,
5-chloro-2-imino-1-[3-(methylsulfonyl)benzyl]-1,2-dihydropyridine-3-carboxamide, and
5-chloro-2-imino-1-(3-morpholin-4-ylbenzyl)-1,2-dihydropyridine-3-carboxamide are excluded,
or a salt thereof;
[2] the compound of the above-mentioned [1], wherein ring A- is a group represented by

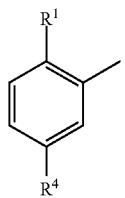

wherein
$R^1$ is as defined in the above-mentioned [1], and
$R^4$ is a halogen atom or an alkyl group optionally having substituent(s);

[3] the compound of the above-mentioned [1], wherein ring A- is a group represented by

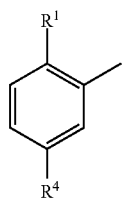

wherein
R¹ is as defined in the above-mentioned [1], and
R⁴ is a halogen atom or an alkyl group optionally having substituent(s), and
R² is a halogen atom or a $C_{1-6}$ alkyl group;

[4] the compound of the above-mentioned [1], wherein ring A- is a group represented by

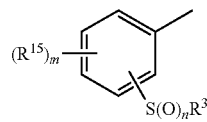

wherein
$R^{15}$ is (1) a halogen atom, (2) a $C_{1-6}$ alkoxy group optionally having 1 to 3 halogen atoms, or (3) an alkyl group optionally having substituent(s),
m is an integer of 0 to 2, and
other symbols are as defined in the above-mentioned [1];

[5] the compound of the above-mentioned [4], wherein ring A- is a group represented by

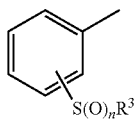

wherein each symbol is as defined in the above-mentioned [1];

[6] a compound represented by the formula

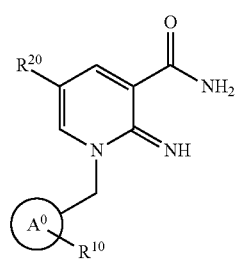

(I')

wherein
ring $A^0$- is an aromatic ring group having at least one substituent $R^{10}$ and optionally further having substituent(s),
$R^{10}$ is a group selected from
(1) a group represented by the formula —S(O)$_n$R$^{30}$ wherein $R^{30}$ is a non-aromatic nitrogen-containing heterocyclic group optionally having substituent(s), and n is an integer of 0 to 2, (2) an alkoxycarbonylamino group,
(3) an alkylsulfonylamino group, and
(4) an alkylcarbonylamino group, and
$R^{20}$ is a hydrogen atom, a halogen atom, a cyano group, a hydrocarbon group optionally having substituent(s), an acyl group, a heterocyclic group optionally having substituent(s), an amino group optionally having substituent(s), a hydroxy group optionally having a substituent, or a mercapto group optionally having a substituent, or a salt thereof (hereinafter to be abbreviated as compound (I'));

[7] 5-chloro-1-[5-chloro-2-(methylsulfonyl)benzyl]-2-imino-1,2-dihydropyridine-3-carboxamide or a salt thereof;

[8] 5-chloro-1-[5-chloro-2-(methylsulfinyl)benzyl]-2-imino-1,2-dihydropyridine-3-carboxamide or a salt thereof;

[9] 5-chloro-1-[5-fluoro-2-(methylsulfonyl)benzyl]-2-imino-1,2-dihydropyridine-3-carboxamide or a salt thereof;

[10] 5-chloro-1-[2-(ethylsulfonyl)-5-fluorobenzyl]-2-imino-1,2-dihydropyridine-3-carboxamide or a salt thereof;

[11] 5-chloro-1-(5-chloro-2-sulfamoylbenzyl)-2-imino-1,2-dihydropyridine-3-carboxamide or a salt thereof;

[12] 5-chloro-1-[5-chloro-2-(2-oxopyrrolidin-1-yl)benzyl]-2-imino-1,2-dihydropyridine-3-carboxamide or a salt thereof;

[13] a prodrug of the compound of the above-mentioned [1] or the compound of the above-mentioned [6];

[14] a pharmaceutical agent comprising the compound of the above-mentioned [1] or a prodrug thereof, or the compound of the above-mentioned [6] or a prodrug thereof;

[15] the pharmaceutical agent of the above-mentioned [14], which is $\alpha_{1D}$ adrenoceptor antagonist;

[16] the pharmaceutical agent of the above-mentioned [14], which is an agent for the prophylaxis or treatment of lower urinary tract diseases;

[17] a method for the prophylaxis or treatment of lower urinary tract diseases in a mammal, which comprises administering an effective amount of compound of the above-mentioned [1] or a prodrug thereof, or the compound of the above-mentioned [6] or a prodrug thereof to the mammal;

[18] use of the compound of the above-mentioned [1] or a prodrug thereof, or the compound of the above-mentioned [6] or a prodrug thereof for the production of an agent for the prophylaxis or treatment of lower urinary tract diseases;

and the like.

Advantageous Effect of the Invention

The compound (I) of the present invention has a superior selective $\alpha_{1D}$ adrenaline receptor antagonistic action, and is useful as an agent for the prophylaxis or treatment of a lower urinary tract disease and the like.

DETAILED DESCRIPTION OF THE INVENTION

The present invention is explained in detail in the following.

In the formula (I), examples of the "aromatic ring group" of the "aromatic ring group having at least one substituent $R^1$ and optionally further having substituent(s)" for ring A- include an aryl group and a 5- or 6-membered aromatic heterocyclic group.

Examples of the aryl group include $C_{6-14}$ aryl groups such as phenyl, 1- or 2-naphthyl, 1-, 2- or 9-anthryl and the like.

Examples of the 5- or 6-membered aromatic heterocyclic group include a 5- or 6-membered aromatic heterocyclic group containing, besides carbon atoms, 1 to 4 hetero atoms selected from a nitrogen atom, a sulfur atom and an oxygen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl etc.).

The "aromatic ring group" is preferably a $C_{6-14}$ aryl group, particularly preferably phenyl.

The "aromatic ring group" has at least one substituent $R^1$ and optionally further has substituent(s).

$R^1$ is a group selected from
(1) a group represented by the formula —$S(O)_nR^3$ wherein $R^3$ is a hydrogen atom, a hydrocarbon group optionally having substituent(s) or an amino group optionally having substituent(s), and n is an integer of 0 to 2,
(2) a non-aromatic nitrogen-containing heterocyclic group optionally having substituent(s),
(3) a carbamoyl group optionally having substituent(s),
(4) an amino group substituted by carbamoyl optionally having substituent(s),
(5) an alkoxycarbonyl group, and
(6) an alkyl group substituted by hydroxy.

Examples of the "hydrocarbon group" of the "hydrocarbon group optionally having substituent(s)" for $R^3$ include a chain or cyclic hydrocarbon group (e.g., alkyl, alkenyl, alkynyl, cycloalkyl, aryl, aralkyl etc.). Of these, a chain or cyclic hydrocarbon group having 1 to 16 carbon atoms and the like are preferable.

Examples of the alkyl include $C_{1-6}$ alkyl (e.g., methyl, ethyl, propyl, isopropyl, butyl, isobutyl, sec-butyl, tert-butyl, pentyl, hexyl etc.) and the like.

Examples of the alkenyl include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of the alkynyl include $C_{2-6}$ alkynyl (e.g., ethynyl, propargyl, 1-butynyl, 2-butynyl, 3-butynyl, 1-hexynyl etc.) and the like.

Examples of the cycloalkyl include $C_{3-7}$ cycloalkyl (e.g., cyclopropyl, cyclobutyl, cyclopentyl, cyclohexyl, cycloheptyl etc.) and the like.

Examples of the aryl include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of the aralkyl include $C_{7-16}$ aralkyl (e.g., phenyl-$C_{1-6}$ alkyl such as benzyl, phenethyl, diphenylmethyl, 2,2-diphenylethyl, 3-phenylpropyl, 4-phenylbutyl, 5-phenylpentyl and the like; naphthyl-$C_{1-6}$ alkyl such as 1-naphthylmethyl, 2-naphthylmethyl and the like; diphenyl-$C_{1-4}$ alkyl etc.) and the like.

When the "hydrocarbon group" is alkyl, alkenyl or alkynyl, it is optionally substituted by 1 to 3 substituents selected from
(1) a halogen atom (e.g., fluorine atom, chlorine atom, bromine atom, iodine atom etc.),
(2) nitro,
(3) cyano,
(4) hydroxy,
(5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.),
(6) $C_{6-14}$ aryloxy (e.g., phenyloxy, naphthyloxy etc.),
(7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.),
(8) mercapto,
(9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.),
(10) $C_{6-14}$ arylthio (e.g., phenylthio, naphthylthio etc.),
(11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.),
(12) amino,
(13) mono-$C_{1-6}$ alkylamino (e.g., methylamino, ethylamino etc.),
(14) mono-$C_{6-14}$ arylamino (e.g., phenylamino, 1-naphthylamino, 2-naphthylamino etc.),
(15) mono-$C_{7-16}$ aralkylamino (e.g., benzylamino etc.),
(16) di-$C_{1-6}$ alkylamino (e.g., dimethylamino, diethylamino etc.),
(17) di-$C_{6-14}$ arylamino (e.g., diphenylamino etc.),
(18) di-$C_{7-16}$ aralkylamino (e.g., dibenzylamino etc.),
(19) formyl,
(20) $C_{1-6}$ alkyl-carbonyl (e.g., acetyl, propionyl etc.),
(21) $C_{6-14}$ aryl-carbonyl (e.g., benzoyl, 1-naphthoyl, 2-naphthoyl etc.),
(22) carboxy,
(23) $C_{1-6}$ alkoxy-carbonyl (e.g., methoxycarbonyl, ethoxycarbonyl, propoxycarbonyl, tert-butoxycarbonyl etc.),
(24) $C_{6-14}$ aryloxy-carbonyl (e.g., phenoxycarbonyl etc.),
(25) carbamoyl,
(26) thiocarbamoyl,
(27) mono-$C_{1-6}$ alkyl-carbamoyl (e.g., methylcarbamoyl, ethylcarbamoyl etc.),
(28) di-$C_{1-6}$ alkyl-carbamoyl (e.g., dimethylcarbamoyl, diethylcarbamoyl, ethylmethylcarbamoyl etc.),
(29) $C_{6-14}$ aryl-carbamoyl (e.g., phenylcarbamoyl, 1-naphthylcarbamoyl, 2-naphthylcarbamoyl etc.),
(30) $C_{1-6}$ alkylsulfonyl (e.g., methylsulfonyl, ethylsulfonyl etc.),
(31) $C_{6-14}$ arylsulfonyl (e.g., phenylsulfonyl, 1-naphthylsulfonyl, 2-naphthylsulfonyl etc.),
(32) $C_{1-6}$ alkylsulfinyl (e.g., methylsulfinyl, ethylsulfinyl etc.),
(33) $C_{6-14}$ arylsulfinyl (e.g., phenylsulfinyl, 1-naphthylsulfinyl, 2-naphthylsulfinyl etc.),
(34) formylamino,
(35) $C_{1-6}$ alkyl-carbonylamino (e.g., acetylamino etc.),
(36) $C_{6-14}$ aryl-carbonylamino (e.g., benzoylamino, naphthoylamino etc.),
(37) $C_{1-6}$ alkoxy-carbonylamino (e.g., methoxycarbonylamino, ethoxycarbonylamino, propoxycarbonylamino, butoxycarbonylamino etc.),
(38) $C_{1-6}$ alkylsulfonylamino (e.g., methylsulfonylamino, ethylsulfonylamino etc.),
(39) $C_{6-14}$ arylsulfonylamino (e.g., phenylsulfonylamino, 2-naphthylsulfonylamino, 1-naphthylsulfonylamino etc.),
(40) $C_{1-6}$ alkyl-carbonyloxy (e.g., acetoxy, propionyloxy etc.),
(41) $C_{6-14}$ aryl-carbonyloxy (e.g., benzoyloxy, naphthylcarbonyloxy etc.),
(42) $C_{1-6}$ alkoxy-carbonyloxy (e.g., methoxycarbonyloxy, ethoxycarbonyloxy, propoxycarbonyloxy, butoxycarbonyloxy etc.),

(43) mono-$C_{1-6}$ alkyl-carbamoyloxy (e.g., methylcarbamoyloxy, ethylcarbamoyloxy etc.),
(44) di-$C_{1-6}$ alkyl-carbamoyloxy (e.g., dimethylcarbamoyloxy, diethylcarbamoyloxy etc.),
(45) $C_{6-14}$ aryl-carbamoyloxy (e.g., phenylcarbamoyloxy, naphthylcarbamoyloxy etc.),
(46) 5- to 7-membered saturated cyclic amino optionally containing, besides carbon atoms and one nitrogen atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.),
(47) a 5- to 10-membered aromatic heterocyclic group containing, besides carbon atoms, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.),
(48) $C_{1-3}$ alkylenedioxy (e.g., methylenedioxy, ethylenedioxy etc.),
(49) $C_{3-7}$ cycloalkyl (e.g., cyclopropyl, cyclobutyl, cyclopentyl, cyclohexyl, cycloheptyl etc.)
and the like.

In addition, when the above-mentioned "hydrocarbon group" is cycloalkyl, aryl or aralkyl, it is optionally substituted by 1 to 5 (preferably 1 to 3) substituents selected from
(1) a halogen atom (e.g., fluorine atom, chlorine atom, bromine atom, iodine atom etc.),
(2) nitro,
(3) cyano,
(4) hydroxy,
(5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.),
(6) $C_{6-14}$ aryloxy (e.g., phenyloxy, naphthyloxy etc.),
(7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.),
(8) mercapto,
(9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.),
(10) $C_{6-14}$ arylthio (e.g., phenylthio, naphthylthio etc.),
(11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.),
(12) amino,
(13) mono-$C_{1-6}$ alkylamino (e.g., methylamino, ethylamino etc.),
(14) mono-$C_{6-14}$ arylamino (e.g., phenylamino, 1-naphthylamino, 2-naphthylamino etc.),
(15) mono-$C_{7-16}$ aralkylamino (e.g., benzylamino etc.),
(16) di-$C_{1-6}$ alkylamino (e.g., dimethylamino, diethylamino etc.),
(17) di-$C_{6-14}$ arylamino (e.g., diphenylamino etc.),
(18) di-$C_{7-16}$ aralkylamino (e.g., dibenzylamino etc.),
(19) formyl,
(20) $C_{1-6}$ alkyl-carbonyl (e.g., acetyl, propionyl etc.),
(21) $C_{6-14}$ aryl-carbonyl (e.g., benzoyl, 1-naphthoyl, 2-naphthoyl etc.),
(22) carboxy,
(23) $C_{1-6}$ alkoxy-carbonyl (e.g., methoxycarbonyl, ethoxycarbonyl, propoxycarbonyl, tert-butoxycarbonyl etc.),
(24) $C_{6-14}$ aryloxy-carbonyl (e.g., phenoxycarbonyl etc.),
(25) carbamoyl,
(26) thiocarbamoyl,
(27) mono-$C_{1-6}$ alkyl-carbamoyl (e.g., methylcarbamoyl, ethylcarbamoyl etc.),
(28) di-$C_{1-6}$ alkyl-carbamoyl (e.g., dimethylcarbamoyl, diethylcarbamoyl, ethylmethylcarbamoyl etc.),
(29) $C_{6-14}$ aryl-carbamoyl (e.g., phenylcarbamoyl, 1-naphthylcarbamoyl, 2-naphthylcarbamoyl etc.),
(30) $C_{1-6}$ alkylsulfonyl optionally having 1 to 3 halogen atoms (e.g., fluorine atom, chlorine atom, bromine atom, iodine atom) (e.g., methylsulfonyl, ethylsulfonyl, trifluoromethylsulfonyl etc.),
(31) $C_{6-14}$ arylsulfonyl (e.g., phenylsulfonyl, 1-naphthylsulfonyl, 2-naphthylsulfonyl etc.),
(32) $C_{1-6}$ alkylsulfinyl (e.g., methylsulfinyl, ethylsulfinyl etc.),
(33) $C_{6-14}$ arylsulfinyl (e.g., phenylsulfinyl, 1-naphthylsulfinyl, 2-naphthylsulfinyl etc.),
(34) formylamino,
(35) $C_{1-6}$ alkyl-carbonylamino (e.g., acetylamino etc.),
(36) $C_{6-14}$ aryl-carbonylamino (e.g., benzoylamino, naphthoylamino etc.),
(37) $C_{1-6}$ alkoxy-carbonylamino (e.g., methoxycarbonylamino, ethoxycarbonylamino, propoxycarbonylamino, butoxycarbonylamino etc.),
(38) $C_{1-6}$ alkylsulfonylamino (e.g., methylsulfonylamino, ethylsulfonylamino etc.),
(39) $C_{6-14}$ arylsulfonylamino (e.g., phenylsulfonylamino, 2-naphthylsulfonylamino, 1-naphthylsulfonylamino etc.),
(40) $C_{1-6}$ alkyl-carbonyloxy (e.g., acetoxy, propionyloxy etc.),
(41) $C_{6-14}$ aryl-carbonyloxy (e.g., benzoyloxy, naphthylcarbonyloxy etc.),
(42) $C_{1-6}$ alkoxy-carbonyloxy (e.g., methoxycarbonyloxy, ethoxycarbonyloxy, propoxycarbonyloxy, butoxycarbonyloxy etc.),
(43) mono-$C_{1-6}$ alkyl-carbamoyloxy (e.g., methylcarbamoyloxy, ethylcarbamoyloxy etc.),
(44) di-$C_{1-6}$ alkyl-carbamoyloxy (e.g., dimethylcarbamoyloxy, diethylcarbamoyloxy etc.),
(45) $C_{6-14}$ aryl-carbamoyloxy (e.g., phenylcarbamoyloxy, naphthylcarbamoyloxy etc.),
(46) 5- to 7-membered saturated cyclic amino optionally containing, besides carbon atoms and one nitrogen atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.),
(47) a 5- to 10-membered aromatic heterocyclic group containing, besides carbon atoms, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.),
(48) $C_{1-3}$ alkylenedioxy (e.g., methylenedioxy, ethylenedioxy etc.),
(49) $C_{3-7}$ cycloalkyl (e.g., cyclopropyl, cyclobutyl, cyclopentyl, cyclohexyl, cycloheptyl etc.),

(50) $C_{1-6}$ alkyl (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 substituents selected from halogen atoms (e.g., fluorine atom, chlorine atom, bromine atom, iodine atom) and hydroxy,

(51) $C_{2-6}$ alkenyl (e.g., allyl, isopropenyl, isobutenyl, 1-methylallyl, 2-pentenyl, 2-hexenyl etc.) optionally having 1 to 3 halogen atoms (e.g., fluorine atom, chlorine atom, bromine atom, iodine atom),

(52) $C_{2-6}$ alkynyl (e.g., propargyl, 2-butynyl, 3-butynyl, 3-pentynyl, 3-hexynyl etc.),

(53) mono-$C_{3-7}$ cycloalkyl-carbamoyl (e.g., cyclopropylcarbamoyl, cyclobutylcarbamoyl etc.),

(54) 5- to 10-membered heterocyclyl-carbonyl containing, besides carbon atoms, one or two kinds of 1 to 4 hetero atoms selected from a nitrogen atom, a sulfur atom and an oxygen atom (e.g., 4-morpholinocarbonyl etc.),

(55) oxo and the like.

Examples of the "amino group optionally having substituent(s)" for $R^3$ include a group represented by —$NR^5R^6$ wherein $R^5$ and $R^6$ are the same or different and each is a hydrogen atom, a hydrocarbon group optionally having substituent(s), a heterocyclic group optionally having substituent(s) or an acyl group.

Examples of the "hydrocarbon group optionally having substituent(s)" for $R^5$ or $R^6$ include those similar to the above-mentioned "hydrocarbon group optionally having substituent(s)" for $R^3$.

Examples of the "heterocyclic group" of the "heterocyclic group optionally having substituent(s)" for $R^5$ or $R^6$ include a 3- to 8-membered heterocyclic group (preferably a 5- or 6-membered heterocyclic group) containing 1 to 4 hetero atoms selected from a nitrogen atom (optionally oxidized), an oxygen atom, a sulfur atom (optionally mono- or di-oxidized) and the like; and a group derived from a fused ring formed by a 3- to 8-membered heterocycle (preferably a 5- or 6-membered heterocycle) containing 1 to 4 hetero atoms selected from a nitrogen atom (optionally oxidized), an oxygen atom, a sulfur atom (optionally mono- or di-oxidized) and the like, and a benzene ring or a 3- to 8-membered heterocycle (preferably a 5- or 6-membered heterocycle) containing 1 to 4 hetero atoms selected from a nitrogen atom (optionally oxidized), an oxygen atom, a sulfur atom (optionally mono- or di-oxidized) and the like, preferably a group derived from a fused ring formed by a 3- to 8-membered heterocycle (preferably a 5- or 6-membered heterocycle) containing 1 to 4 hetero atoms selected from a nitrogen atom (optionally oxidized), an oxygen atom, a sulfur atom (optionally mono- or di-oxidized) and the like, and a benzene ring.

Specific examples thereof include aziridinyl (e.g., 1- or 2-aziridinyl), azirinyl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or -5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein the sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), triazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein the nitrogen atom is oxidized (e.g., 2-, 3- or 4-pyridyl-N-oxide), pyridazinyl (e.g., 3- or 4-pyridazinyl), pyridazinyl wherein one or both of the nitrogen atom is/are oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atom is/are oxidized (e.g., 2-, 4-, 5- or 6-pyrimidinyl-N-oxide), pyrazinyl, piperidyl (e.g., 1-, 2-, 3- or 4-piperidyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein the sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromene-2- or 3-yl), 2-benzo[b]thienyl, 3-benzo[b]thienyl, 2-benzo[b]furanyl, 3-benzo[b]furanyl and the like.

Examples of the "substituent" that the "heterocyclic group" optionally has include those similar to the substituents that the "hydrocarbon group" of the above-mentioned "optionally substituted hydrocarbon group" for $R^3$ optionally has when the hydrocarbon group is cycloalkyl, aryl or aralkyl. The number of the substituents is 1 to 5, preferably 1 to 3.

Examples of the "acyl group" for $R^5$ or $R^6$ include an acyl group derived from an optionally substituted carboxylic acid, an optionally substituted oxycarboxylic acid, an optionally substituted sulfonic acid, an optionally substituted sulfinic acid and the like, and the like, for example, a group represented by the formula —$S(O)_p$—$R^7$ wherein p is 1 or 2, and $R^7$ is a hydroxy group, a hydrocarbon group optionally having substituent(s) or a heterocyclic group optionally having substituent(s); a group represented by the formula —$COOR^8$ wherein $R^8$ is a hydrogen atom, a hydrocarbon group optionally having substituent(s) or a heterocyclic group optionally having substituent(s); a group represented by the formula —$CONR^9R^{10}$ wherein $R^9$ and $R^{10}$ are the same or different and each is a hydrogen atom, a hydrocarbon group optionally having substituent(s) or a heterocyclic group optionally having substituent(s); a group represented by the formula —$SO_2NH$—$R^{11}$ wherein $R^{11}$ is a hydrogen atom, a hydrocarbon group optionally having substituent(s) or a heterocyclic group optionally having substituent(s); or a group represented by the formula —CO—$R^{12}$ wherein $R^{12}$ is a hydrogen atom, a hydrocarbon group optionally having substituent(s) or a heterocyclic group optionally having substituent(s); and the like.

Examples of the "hydrocarbon group optionally having substituent(s)" for $R^7$, $R^8$, $R^9$, $R^{10}$, $R^{11}$ or $R^{12}$ include those similar to the above-mentioned "hydrocarbon group optionally having substituent(s)" for $R^3$.

Examples of the "heterocyclic group optionally having substituent(s)" for $R^7$, $R^8$, $R^9$, $R^{10}$, $R^{11}$ or $R^{12}$ include those similar to the above-mentioned "heterocyclic group optionally having substituent(s)" for $R^5$ or $R^6$.

$R^3$ is preferably (1) a hydrogen atom, (2) a $C_{1-6}$ alkyl group, or (3) an amino group optionally substituted by 1 or 2 $C_{1-6}$ alkyl.

In another embodiment, $R^3$ is preferably
(1) a $C_{1-6}$ alkyl group optionally substituted by 1 to 3 $C_{1-6}$ alkoxy,
(2) a $C_{3-7}$ cycloalkyl group,
(3) a $C_{6-14}$ aryl group, or
(4) an amino group optionally substituted by 1 or 2 substituents selected from
   (a) $C_{1-6}$ alkyl optionally substituted by 1 to 3 $C_{1-6}$ alkoxy,
   (b) $C_{3-7}$ cycloalkyl, and
   (c) $C_{6-14}$ aryl.

n is an integer of 0 to 2, preferably 1 or 2, particularly preferably n is 2.

Examples of the "non-aromatic nitrogen-containing heterocyclic group" of the "non-aromatic nitrogen-containing heterocyclic group optionally having substituent(s)" for $R^1$ include a 3- to 8-membered (preferably 5 or 6-membered) saturated or unsaturated (preferably saturated) non-aromatic nitrogen-containing heterocycle (aliphatic nitrogen-containing heterocycle) such as azetidine, pyrrolidine, imidazolidine, thiazolidine, oxazolidine, piperidine, morpholine, thiomorpholine, piperazine and the like, and the like.

Examples of the "substituent" that the "non-aromatic nitrogen-containing heterocyclic group" optionally has include those similar to the substituents that the "hydrocarbon group" of the above-mentioned "optionally substituted hydrocarbon group" for $R^3$ optionally has when the hydrocarbon group is cycloalkyl, aryl or aralkyl. The number of the substituents is 1 to 5, preferably 1 to 3.

The "non-aromatic nitrogen-containing heterocyclic group optionally having substituent(s)" is preferably

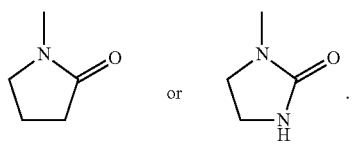

Examples of the "substituent" that the "carbamoyl group" of the "carbamoyl group optionally having substituent(s)" for $R^1$ optionally has include those similar to the "optionally substituted hydrocarbon group" for $R^3$, "heterocyclic group optionally having substituent(s)" for $R^5$ or $R^6$, and the like.

The number of the substituents is 1 or 2.

The "carbamoyl group optionally having substituent(s)" is preferably a carbamoyl group optionally substituted by 1 or 2 $C_{1-6}$ alkyl (e.g., methyl, ethyl etc.).

Examples of the "carbamoyl optionally having substituent(s)" that "amino group" of the "amino group substituted by carbamoyl optionally having substituent(s)" for $R^1$ optionally has include those similar to the aforementioned "carbamoyl group optionally having substituent(s)" for $R^1$. The number of the substituents on the amino group is 1 or 2.

The "amino group substituted by carbamoyl optionally having substituent(s)" is preferably a carbamoylamino group, a mono- or di-$C_{1-6}$ alkyl (e.g., methyl, ethyl etc.)-carbamoylamino group and the like.

Examples of the "alkoxycarbonyl group" for $R^1$ include a $C_{1-6}$ alkoxy-carbonyl group such as methoxycarbonyl, ethoxycarbonyl, propoxycarbonyl, tert-butoxycarbonyl and the like.

Examples of the "alkyl group substituted by hydroxy" for $R^1$ include a $C_{1-6}$ alkyl group (e.g., methyl, ethyl, propyl, isopropyl, butyl, isobutyl, sec-butyl, tert-butyl, pentyl, hexyl etc.) substituted by 1 to 3 hydroxy, and the like.

Of the aforementioned $R^1$, a group represented by the formula —$S(O)_nR^3$ wherein $R^3$ is a hydrogen atom, a hydrocarbon group optionally having substituent(s) or an amino group optionally having substituent(s), and n is an integer of 0 to 2, is preferable.

Moreover, a group represented by the formula —$S(O)_nR^3$
wherein
$R^3$ is
(1) a hydrogen atom,
(2) a $C_{1-6}$ alkyl group, or
(3) an amino group optionally substituted by 1 or 2 $C_{1-6}$ alkyl, and n is an integer of 1 or 2,
is more preferable.

In another embodiment, a group represented by the formula —$S(O)_nR^3$
wherein
$R^3$ is
(1) a $C_{1-6}$ alkyl group optionally substituted by 1 to 3 $C_{1-6}$ alkoxy,
(2) a $C_{3-7}$ cycloalkyl group,
(3) a $C_{6-14}$ aryl group, or
(4) an amino group optionally substituted by 1 or 2 substituents selected from
   (a) $C_{1-6}$ alkyl optionally substituted by 1 to 3 $C_{1-6}$ alkoxy,
   (b) $C_{3-7}$ cycloalkyl, and
   (c) $C_{6-14}$ aryl, and n is an integer of 1 or 2,
is more preferable.

$R^1$ is preferably a group selected from
(1) a group represented by the formula —$S(O)_nR^3$
wherein
$R^3$ is
(1) a hydrogen atom,
(2) a $C_{1-6}$ alkyl group, or
(3) an amino group optionally substituted by 1 or 2 $C_{1-6}$ alkyl, and n is an integer of 1 or 2,
(2)

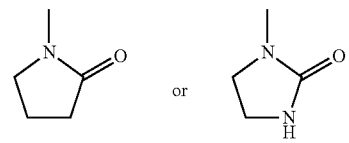

(3) a carbamoyl group optionally substituted by 1 or 2 $C_{1-6}$ alkyl,
(4) a carbamoylamino group or a mono- or di-$C_{1-6}$ alkyl-carbamoylamino group,
(5) a $C_{1-6}$ alkoxy-carbonyl group, and
(6) a $C_{1-6}$ alkyl group substituted by hydroxy.

In another embodiment, $R^1$ is preferably a group selected from
(1) a group represented by the formula —$S(O)_nR^3$
wherein
$R^3$ is
(1) a $C_{1-6}$ alkyl group optionally substituted by 1 to 3 $C_{1-6}$ alkoxy,
(2) a $C_{3-7}$ cycloalkyl group,
(3) a $C_{6-14}$ aryl group, or (4) an amino group optionally substituted by 1 or 2 substituents selected from
(a) $C_{1-6}$ alkyl optionally substituted by 1 to 3 $C_{1-6}$ alkoxy,
(b) $C_{3-7}$ cycloalkyl, and
(c) $C_{6-14}$ aryl, and
n is an integer of 1 or 2, (2)

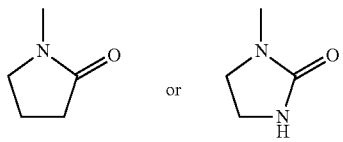

or (3) a carbamoyl group optionally substituted by 1 or 2 $C_{1-6}$ alkyl,
(4) a carbamoylamino group or a mono- or di-$C_{1-6}$ alkyl-carbamoylamino group,
(5) a $C_{1-6}$ alkoxy-carbonyl group, and
(6) a $C_{1-6}$ alkyl group substituted by hydroxy.

The "aromatic ring group" of the "aromatic ring group having at least one substituent $R^1$ and optionally further having substituent(s)" for ring A- optionally further has substituent(s) besides $R^1$ at substitutable positions. Examples of such substituent include
(1) a halogen atom (e.g., fluorine atom, chlorine atom, bromine atom, iodine atom etc.),
(2) nitro,
(3) cyano,
(4) hydroxy,
(5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.),
(6) $C_{6-14}$ aryloxy (e.g., phenyloxy, naphthyloxy etc.),
(7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.),
(8) mercapto,
(9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.),
(10) $C_{6-14}$ arylthio (e.g., phenylthio, naphthylthio etc.),
(11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.),
(12) amino,
(13) mono-$C_{1-6}$ alkylamino (e.g., methylamino, ethylamino etc.),
(14) mono-$C_{6-14}$ arylamino (e.g., phenylamino, 1-naphthylamino, 2-naphthylamino etc.),
(15) mono-$C_{7-16}$ aralkylamino (e.g., benzylamino etc.),
(16) di-$C_{1-6}$ alkylamino (e.g., dimethylamino, diethylamino etc.),
(17) di-$C_{6-14}$ arylamino (e.g., diphenylamino etc.),
(18) di-$C_{7-16}$ aralkylamino (e.g., dibenzylamino etc.),
(19) formyl,
(20) $C_{1-6}$ alkyl-carbonyl (e.g., acetyl, propionyl etc.),
(21) $C_{6-14}$ aryl-carbonyl (e.g., benzoyl, 1-naphthoyl, 2-naphthoyl etc.),
(22) carboxy,
(23) $C_{1-6}$ alkoxy-carbonyl (e.g., methoxycarbonyl, ethoxycarbonyl, propoxycarbonyl, tert-butoxycarbonyl etc.),
(24) $C_{6-14}$ aryloxy-carbonyl (e.g., phenoxycarbonyl etc.),
(25) carbamoyl,
(26) thiocarbamoyl,
(27) mono-$C_{1-6}$ alkyl-carbamoyl (e.g., methylcarbamoyl, ethylcarbamoyl etc.),
(28) di-$C_{1-6}$ alkyl-carbamoyl (e.g., dimethylcarbamoyl, diethylcarbamoyl, ethylmethylcarbamoyl etc.),
(29) $C_{6-14}$ aryl-carbamoyl (e.g., phenylcarbamoyl, 1-naphthylcarbamoyl, 2-naphthylcarbamoyl etc.),
(30) $C_{1-6}$ alkylsulfonyl optionally having 1 to 3 halogen atoms (e.g., fluorine atom, chlorine atom, bromine atom, iodine atom) (e.g., methylsulfonyl, ethylsulfonyl, trifluoromethylsulfonyl etc.),
(31) $C_{6-14}$ arylsulfonyl (e.g., phenylsulfonyl, 1-naphthylsulfonyl, 2-naphthylsulfonyl etc.),
(32) $C_{1-6}$ alkylsulfinyl (e.g., methylsulfinyl, ethylsulfinyl etc.),
(33) $C_{6-14}$ arylsulfinyl (e.g., phenylsulfinyl, 1-naphthylsulfinyl, 2-naphthylsulfinyl etc.),
(34) formylamino,
(35) $C_{1-6}$ alkyl-carbonylamino (e.g., acetylamino etc.),
(36) $C_{6-14}$ aryl-carbonylamino (e.g., benzoylamino, naphthoylamino etc.),
(37) $C_{1-6}$ alkoxy-carbonylamino (e.g., methoxycarbonylamino, ethoxycarbonylamino, propoxycarbonylamino, butoxycarbonylamino etc.),
(38) $C_{1-6}$ alkylsulfonylamino (e.g., methylsulfonylamino, ethylsulfonylamino etc.),
(39) $C_{6-14}$ arylsulfonylamino (e.g., phenylsulfonylamino, 2-naphthylsulfonylamino, 1-naphthylsulfonylamino etc.),
(40) $C_{1-6}$ alkyl-carbonyloxy (e.g., acetoxy, propionyloxy etc.),
(41) $C_{6-14}$ aryl-carbonyloxy (e.g., benzoyloxy, naphthylcarbonyloxy etc.),
(42) $C_{1-6}$ alkoxy-carbonyloxy (e.g., methoxycarbonyloxy, ethoxycarbonyloxy, propoxycarbonyloxy, butoxycarbonyloxy etc.),
(43) mono-$C_{1-6}$ alkyl-carbamoyloxy (e.g., methylcarbamoyloxy, ethylcarbamoyloxy etc.),
(44) di-$C_{1-6}$ alkyl-carbamoyloxy (e.g., dimethylcarbamoyloxy, diethylcarbamoyloxy etc.),
(45) $C_{6-14}$ aryl-carbamoyloxy (e.g., phenylcarbamoyloxy, naphthylcarbamoyloxy etc.),
(46) 5- to 7-membered saturated cyclic amino optionally containing, besides carbon atoms and one nitrogen atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.),
(47) a 5- to 10-membered aromatic heterocyclic group containing, besides carbon atoms, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.),
(48) $C_{1-3}$ alkylenedioxy (e.g., methylenedioxy, ethylenedioxy etc.),
(49) $C_{3-7}$ cycloalkyl (e.g., cyclopropyl, cyclobutyl, cyclopentyl, cyclohexyl, cycloheptyl etc.),
(50) alkyl optionally having substituent(s) (e.g., $C_{1-6}$ alkyl (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 substituents selected from a halogen atom (e.g., fluorine atom, chlorine atom, bromine atom, iodine atom) and hydroxy),

(51) $C_{2-6}$ alkenyl (e.g., allyl, isopropenyl, isobutenyl, 1-methylallyl, 2-pentenyl, 2-hexenyl etc.) optionally having 1 to 3 halogen atoms (e.g., fluorine atom, chlorine atom, bromine atom, iodine atom),

(52) $C_{2-6}$ alkynyl (e.g., propargyl, 2-butynyl, 3-butynyl, 3-pentynyl, 3-hexynyl etc.),

(53) mono-$C_{3-7}$ cycloalkyl-carbamoyl (e.g., cyclopropylcarbamoyl, cyclobutylcarbamoyl etc.),

(54) 5- to 10-membered heterocyclyl-carbonyl containing, besides carbon atoms, one or two kinds of 1 to 4 hetero atoms selected from a nitrogen atom, a sulfur atom and an oxygen atom (e.g., 4-morpholinocarbonyl etc.)

and the like.

The number of substituent other than $R^1$ is 0 to 5 (preferably 0 to 3, more preferably 1 or 2).

The substituent other than $R^1$ is preferably (1) a halogen atom, (2) $C_{1-6}$ alkoxy optionally having 1 to 3 halogen atoms, (3) alkyl optionally having substituent(s) (e.g., $C_{1-6}$ alkyl optionally having 1 to 3 substituents selected from a halogen atom and hydroxyl, and the like)

and the like, particularly preferably (1) a halogen atom, (3) alkyl optionally having substituent(s) (e.g., $C_{1-6}$ alkyl optionally having 1 to 3 substituents selected from a halogen atom and hydroxyl, and the like)

and the like.

Ring A- is preferably a group represented by

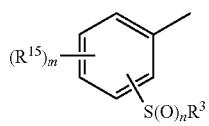

wherein $R^{15}$ is (1) a halogen atom, (2) a $C_{1-6}$ alkoxy group optionally having 1 to 3 halogen atoms, or (3) an alkyl group optionally having substituent(s) (e.g., a $C_{1-6}$ alkyl group optionally having 1 to 3 substituents selected from a halogen atom and hydroxyl, and the like), m is an integer of 0 to 2, and other symbols are as defined above.

Ring A- is particularly preferably a group represented by

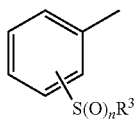

wherein each symbol is as defined above.

In the embodiment, it is particularly preferable that $R^3$ is (1) a $C_{1-6}$ alkyl group, or (2) an amino group optionally substituted by 1 or 2 $C_{1-6}$ alkyl, and n is an integer of 1 or 2.

Alternatively, it is particularly preferable that $R^3$ is (1) a $C_{1-6}$ alkyl group optionally substituted by 1 to 3 $C_{1-6}$ alkoxy, (2) a $C_{3-7}$ cycloalkyl group, (3) a $C_{6-14}$ aryl group, or (4) an amino group optionally substituted by 1 or 2 substituents selected from (a) $C_{1-6}$ alkyl optionally substituted by 1 to 3 $C_{1-6}$ alkoxy, (b) $C_{3-7}$ cycloalkyl, and (c) $C_{6-14}$ aryl, and n is an integer of 1 or 2.

In another embodiment, ring A- is preferably a group represented by

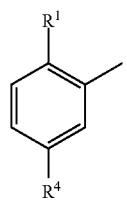

wherein $R^1$ is as defined above, $R^4$ is a halogen atom (e.g., fluorine, chlorine, bromine, iodine) or an alkyl group optionally having substituent(s) (e.g., a $C_{1-6}$ alkyl group optionally having 1 to 3 substituents selected from a halogen atom and hydroxyl, and the like).

The structure wherein $R^1$ is bonded to the 2-position of the phenyl group and $R^4$ is bonded to the 5-position of the phenyl group is effective for activity expression.

In embodiment, $R^1$ is preferably a group selected from (1) a group represented by the formula —S(O)$_n$R$^3$ wherein $R^3$ is (1) a hydrogen atom, (2) a $C_{1-6}$ alkyl group, or (3) an amino group optionally substituted by 1 or 2 $C_{1-6}$ alkyl, and n is an integer of 1 or 2, (2)

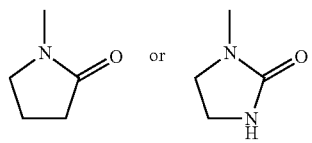

(3) a carbamoyl group optionally substituted by 1 or 2 $C_{1-6}$ alkyl, (4) a carbamoylamino group or a mono- or di-$C_{1-6}$ alkyl-carbamoylamino group, (5) a $C_{1-6}$ alkoxy-carbonyl group, and (6) a $C_{1-6}$ alkyl group substituted by hydroxyl.

Alternatively, $R^1$ is preferably a group selected from (1) a group represented by the formula —S(O)$_n$R$^3$ wherein $R^3$ is (1) a $C_{1-6}$ alkyl group optionally substituted by 1 to 3 $C_{1-6}$ alkoxy, (2) a $C_{3-7}$ cycloalkyl group, (3) a $C_{6-14}$ aryl group, or
(4) an amino group optionally substituted by 1 or 2 substituents selected from
   (a) $C_{1-6}$ alkyl optionally substituted by 1 to 3 $C_{1-6}$ alkoxy,
   (b) $C_{3-7}$ cycloalkyl, and
   (c) $C_{6-14}$ aryl, and
n is an integer of 1 or 2, (2)

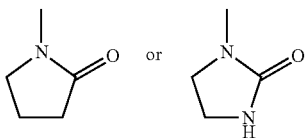

(3) a carbamoyl group optionally substituted by 1 or 2 $C_{1-6}$ alkyl,
(4) a carbamoylamino group or a mono- or di-$C_{1-6}$ alkyl-carbamoylamino group,
(5) a $C_{1-6}$ alkoxy-carbonyl group, and
(6) a $C_{1-6}$ alkyl group substituted by hydroxy.

In the formula (I), $R^2$ is a hydrogen atom, a halogen atom, a cyano group, a hydrocarbon group optionally having substituent(s), an acyl group, a heterocyclic group optionally having substituent(s), an amino group optionally having substituent(s), a hydroxy group optionally having a substituent, or a mercapto group optionally having a substituent.

Examples of the "halogen atom" for $R^2$ include fluorine atom, chlorine atom, bromine atom and iodine atom.

Examples of the "hydrocarbon group optionally having substituent(s)" for $R^2$ include those similar to the aforementioned "optionally substituted hydrocarbon group" for $R^3$.

Examples of the "acyl group" for $R^2$ include those similar to the aforementioned "acyl group" for $R^5$ or $R^6$. Preferable examples thereof include a $C_{1-7}$ alkanoyl group (e.g., formyl; $C_{1-6}$ alkyl-carbonyl such as acetyl, propionyl, butyryl, isobutyryl, pentanoyl, hexanoyl, heptanoyl and the like, etc.), a $C_{6-14}$ aryl-carbonyl group (e.g., benzoyl, naphthalenecarbonyl etc.), a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), a $C_{6-14}$ aryloxy-carbonyl group (e.g., phenoxycarbonyl group), a $C_{7-19}$ aralkyl-carbonyl group (e.g., phenyl-$C_{1-4}$ alkylcarbonyl such as benzylcarbonyl, phenethylcarbonyl, phenylpropylcarbonyl and the like; naphthyl-$C_{1-4}$ alkylcarbonyl such as naphthylethylcarbonyl and the like, etc.), a $C_{7-19}$ aralkyloxy-carbonyl group (e.g., phenyl-$C_{1-4}$ alkyloxycarbonyl such as benzyloxycarbonyl and the like, etc.), a 5- or 6-membered heterocyclyl-carbonyl group or a fused heterocyclyl-carbonyl group thereof (e.g., a 5- or 6-membered heterocyclyl-carbonyl group containing 1 to 4 hetero atoms selected from a nitrogen atom (optionally oxidized), an oxygen atom, a sulfur atom (optionally mono- or di-oxidized) and the like, such as pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolylcarbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like; oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl wherein the nitrogen atom is oxidized such as 2-, 3- or 4-pyridyl-N-oxidocarbonyl and the like; pyridazinylcarbonyl such as 3- or 4-pyridazinylcarbonyl and the like; pyridazinylcarbonyl wherein one or both of the nitrogen atom is oxidized such as 3-, 4-, 5- or 6-pyridazinyl-N-oxidocarbonyl and the like; pyrimidinylcarbonyl such as 2-, 4- or 5-pyrimidinylcarbonyl and the like; pyrimidinylcarbonyl wherein one or both of the nitrogen atom is oxidized such as 2-, 4-, 5- or 6-pyrimidinyl-N-oxidocarbonyl and the like; pyrazinylcarbonyl; piperidylcarbonyl such as 2-, 3- or 4-piperidylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl such as 1,5-, 1,6-, 1,7-, 1,8-, 2,6- or 2,7-naphthyridinylcarbonyl (e.g., 1,5-naphthyridin-2- or 3-ylcarbonyl) and the like; thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); chromenylcarbonyl (e.g., 2H-chromen-2- or 3-ylcarbonyl etc.) and the like), a 5- or 6-membered heterocyclyl-acetyl group (e.g., a 5- or 6-membered heterocyclyl-acetyl group containing 1 to 4 hetero atoms selected from a nitrogen atom (optionally oxidized), an oxygen atom, a sulfur atom (optionally mono- or di-oxidized) and the like, such as 2-pyrrolylacetyl, 3-imidazolylacetyl, 5-isoxazolylacetyl and the like) and the like.

The "acyl group" is optionally substituted. For example, when the "acyl group" is a $C_{1-7}$ alkanoyl group or a $C_{1-6}$ alkoxy-carbonyl group, it is optionally substituted by 1 to 3 substituents selected from alkylthio (e.g., $C_{1-4}$ alkylthio such as methylthio, ethylthio, n-propylthio, isopropylthio and the like, and the like), a halogen atom (e.g., fluorine, chlorine, bromine, iodine), alkoxy (e.g., $C_{1-6}$ alkoxy such as methoxy, ethoxy, n-propoxy, tert-butoxy, n-hexyloxy and the like, and the like), nitro, alkoxy-carbonyl (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), alkylamino (e.g., mono- or di-$C_{1-6}$ alkylamino such as methylamino, ethylamino, n-propylamino, n-butylamino, tert-butylamino, n-pentylamino, n-hexylamino, dimethylamino, diethylamino, methylethylamino, di-(n-propyl)amino, di-(n-butyl)amino and the like, and the like), alkoxyimino (e.g., $C_{1-6}$ alkoxyimino such as methoxyimino, ethoxyimino, n-propoxyimino, tert-butoxy imino, n-hexyloxy-imino and the like, and the like), and hydroxyimino.

When the "acyl group" is a $C_{6-14}$ aryl-carbonyl group, a $C_{6-14}$ aryloxy-carbonyl group, a $C_{7-19}$ aralkyl-carbonyl group, a $C_{7-19}$ aralkyloxy-carbonyl group, a 5- or 6-membered heterocyclyl-carbonyl group or a fused heterocyclyl-carbonyl group thereof, or a 5- or 6-membered heterocyclyl-acetyl group, it is optionally substituted by 1 to 5 (preferably 1 to 3) substituents selected from alkyl (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like; $C_{3-6}$ cycloalkyl such as cyclohexyl and the like, and the like), alkenyl (e.g., $C_{2-6}$ alkenyl such as allyl, isopropenyl, isobutenyl, 1-methylallyl, 2-pentenyl, 2-hexenyl and the like, and the like), alkynyl (e.g., $C_{2-6}$ alkynyl such as propargyl, 2-butynyl, 3-butynyl, 3-pentynyl, 3-hexynyl and the like, and the like), alkoxy (e.g., $C_{1-6}$ alkoxy such as methoxy, ethoxy, n-propoxy, tert-butoxy, n-hexyloxy and the like, and the like), acyl [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like], nitro, amino, hydroxy, cyano, sulfamoyl, mercapto, a halogen atom (e.g., fluorine, chlorine, bromine, iodine), and alkylthio ($C_{1-4}$ alkylthio such as methylthio, ethylthio, n-propylthio, isobutylthio and the like, and the like).

Examples of the "heterocyclic group optionally having substituent(s)" for $R^2$ include those similar to the above-mentioned "heterocyclic group optionally having substituent(s)" for $R^5$ or $R^6$.

Examples of the "amino group optionally having substituent(s)" for $R^2$ include those similar to the above-mentioned "amino group optionally having substituent(s)" for $R^3$.

Examples of the "hydroxy group optionally having a substituent" for $R^2$ include a group represented by the formula —$OR^{13}$ wherein $R^{13}$ is a hydrogen atom, a hydrocarbon group optionally having substituent(s), a heterocyclic group optionally having substituent(s) or an acyl group.

Examples of the "hydrocarbon group optionally having substituent(s)" for $R^{13}$ include those similar to the above-mentioned "hydrocarbon group optionally having substituent(s)" for $R^3$.

Examples of the "heterocyclic group optionally having substituent(s)" for $R^{13}$ include those similar to the above-mentioned "heterocyclic group optionally having substituent(s)" for $R^5$ or $R^6$.

Examples of the "acyl group" for $R^{13}$ include those similar to the above-mentioned "acyl group" for $R^2$.

Examples of the "mercapto group optionally having a substituent" include a group represented by the formula —$SR^{14}$ wherein $R^{14}$ is a hydrogen atom, a hydrocarbon group optionally having substituent(s), a heterocyclic group optionally having substituent(s) or an acyl group.

Examples of the "hydrocarbon group optionally having substituent(s)" for $R^{14}$ include those similar to the above-mentioned "hydrocarbon group optionally having substituent(s)" for $R^3$.

Examples of the "heterocyclic group optionally having substituent(s)" for $R^{14}$ include those similar to the above-mentioned "heterocyclic group optionally having substituent(s)" for $R^5$ or $R^6$.

Examples of the "acyl group" for $R^{14}$ include those similar to the above-mentioned "acyl group" for $R^2$.

$R^2$ is preferably a halogen atom or a $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.), particularly preferably a halogen atom.

Preferable embodiment of compound (I) is shown in the following.

(1) A compound represented by the formula

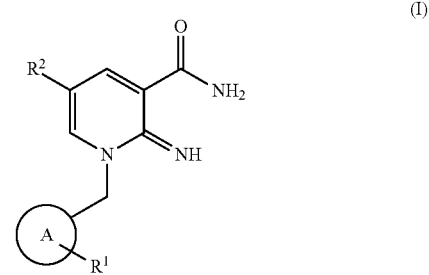

(I)

wherein ring A- is a $C_{6-14}$ aryl group (preferably, phenyl) or a 5- or 6-membered aromatic heterocyclic group, each of having at least one substituent $R^1$ and optionally further having substituent(s);

$R^1$ is a group selected from (1) A group represented by the formula —$S(O)_nR^3$ wherein $R^3$ is (1) a hydrogen atom, (2) a $C_{1-6}$ alkyl group, or (3) an amino group optionally substituted by 1 or 2 $C_{1-6}$ alkyl, and n is an integer of 1 or 2, (2)

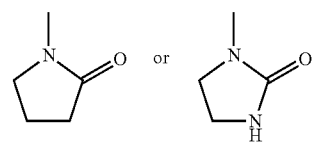

(3) a carbamoyl group optionally substituted by 1 or 2 $C_{1-6}$ alkyl, (4) a carbamoylamino group or a mono- or di-$C_{1-6}$ alkyl-carbamoylamino group, (5) a $C_{1-6}$ alkoxy-carbonyl group, and (6) a $C_{1-6}$ alkyl group substituted by hydroxyl;

$R^2$ is a halogen atom or a $C_{1-6}$ alkyl group; and ring A- optionally further has, besides $R^1$, 1 or 2 substituents selected from (1) a halogen atom, (2) $C_{1-6}$ alkoxy optionally having 1 to 3 halogen atoms, and (3) $C_{1-6}$ alkyl optionally having 1 to 3 substituents selected from a halogen atom and hydroxyl.

(1') A compound represented by the formula

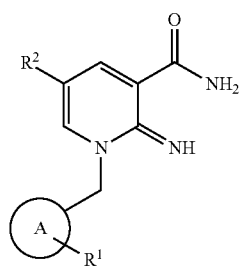
(I)

wherein
ring A- is a $C_{6-14}$ aryl group (preferably, phenyl) or a 5- or 6-membered aromatic heterocyclic group, each of having at least one substituent $R^1$ and optionally further having substituent(s);
$R^1$ is a group selected from
(1) a group represented by the formula —$S(O)_nR^3$
wherein
$R^3$ is
  (1) a $C_{1-6}$ alkyl group optionally substituted by 1 to 3 $C_{1-6}$ alkoxy,
  (2) a $C_{3-7}$ cycloalkyl group,
  (3) a $C_{6-14}$ aryl group, or
  (4) an amino group optionally substituted by 1 or 2 substituents selected from
    (a) $C_{1-6}$ alkyl optionally substituted by 1 to 3 $C_{1-6}$ alkoxy,
    (b) $C_{3-7}$ cycloalkyl, and
    (c) $C_{6-14}$ aryl, and
n is an integer of 1 or 2,
(2)

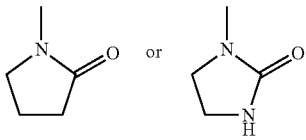

(3) a carbamoyl group optionally substituted by 1 or 2 $C_{1-6}$ alkyl,
(4) a carbamoylamino group or a mono- or di-$C_{1-6}$ alkyl-carbamoylamino group,
(5) a $C_{1-6}$ alkoxy-carbonyl group, and
(6) a $C_{1-6}$ alkyl group substituted by hydroxy;
$R^2$ is a halogen atom or a $C_{1-6}$ alkyl group; and
ring A- optionally further has, besides $R^1$, 1 or 2 substituents selected from
(1) a halogen atom,
(2) $C_{1-6}$ alkoxy optionally having 1 to 3 halogen atoms, and
(3) $C_{1-6}$ alkyl optionally having 1 to 3 substituents selected from a halogen atom and hydroxyl.

(2) A compound represented by the formula

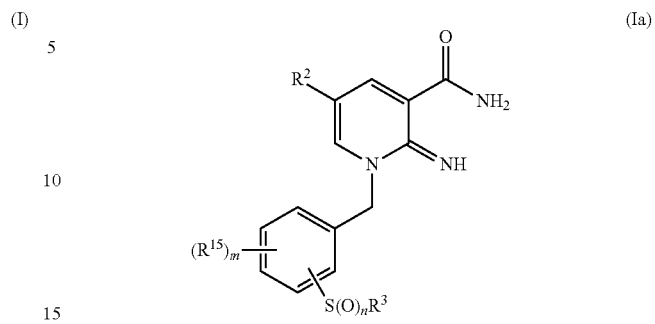
(Ia)

wherein
$R^2$ is a halogen atom or a $C_{1-6}$ alkyl group;
$R^3$ is
(1) a $C_{1-6}$ alkyl group, or
(2) an amino group optionally substituted by 1 or 2 $C_{1-6}$ alkyl;
n is an integer of 1 or 2;
$R^{15}$ is
(1) a halogen atom,
(2) a $C_{1-6}$ alkoxy group optionally having 1 to 3 halogen atoms, or
(3) a $C_{1-6}$ alkyl group optionally having 1 to 3 substituents selected from a halogen atom and hydroxyl; and
m is an integer of 0 to 2.

(2') A compound represented by the formula

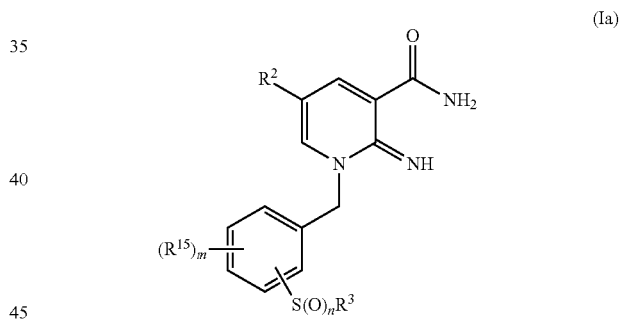
(Ia)

wherein
$R^2$ is a halogen atom or a $C_{1-6}$ alkyl group;
$R^3$ is
(1) a $C_{1-6}$ alkyl group optionally substituted by 1 to 3 $C_{1-6}$ alkoxy,
(2) a $C_{3-7}$ cycloalkyl group,
(3) a $C_{6-14}$ aryl group, or
(4) an amino group optionally substituted by 1 or 2 substituents selected from
  (a) $C_{1-6}$ alkyl optionally substituted by 1 to 3 $C_{1-6}$ alkoxy,
  (b) $C_{3-7}$ cycloalkyl, and
  (c) $C_{6-14}$ aryl; and
n is an integer of 1 or 2;
$R^{15}$ is
(1) a halogen atom,
(2) a $C_{1-6}$ alkoxy group optionally having 1 to 3 halogen atoms, or
(3) a $C_{1-6}$ alkyl group optionally having 1 to 3 substituents selected from a halogen atom and hydroxyl; and
m is an integer of 0 to 2.

(3) A compound represented by the formula

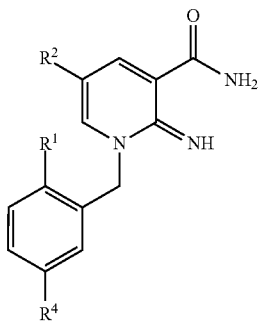

(Ib)

wherein
R¹ is a group selected from
(1) a group represented by the formula —S(O)$_n$R³
wherein
R³ is
(1) a C$_{1-6}$ alkyl group, or
(2) an amino group optionally substituted by 1 or 2 C$_{1-6}$ alkyl, and
n is 1 or 2,
(2)

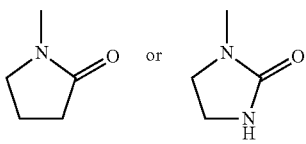

(3) a carbamoyl group optionally substituted by 1 or 2 C$_{1-6}$ alkyl,
(4) a carbamoylamino group or a mono- or di-C$_{1-6}$ alkyl-carbamoylamino group,
(5) a C$_{1-6}$ alkoxy-carbonyl group, and
(6) a C$_{1-6}$ alkyl group substituted by hydroxy;
R⁴ is
(1) a halogen atom,
(2) a C$_{1-6}$ alkoxy group optionally having 1 to 3 halogen atoms, or
(3) a C$_{1-6}$ alkyl group optionally having 1 to 3 substituents selected from a halogen atom and hydroxy; and
R² is a halogen atom or a C$_{1-6}$ alkyl group.
(3') A compound represented by the formula

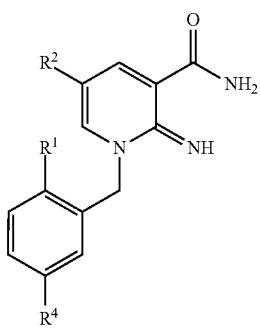

(Ib)

wherein
R¹ is a group selected from
(1) a group represented by the formula —S(O)$_n$R³
wherein
R³ is
(1) a C$_{1-6}$ alkyl group optionally substituted by 1 to 3 C$_{1-6}$ alkoxy,
(2) a C$_{3-7}$ cycloalkyl group,
(3) a C$_{6-14}$ aryl group, or
(4) an amino group optionally substituted by 1 or 2 substituents selected from
(a) C$_{1-6}$ alkyl optionally substituted by 1 to 3 C$_{1-6}$ alkoxy,
(b) C$_{3-7}$ cycloalkyl, and
(c) C$_{6-14}$ aryl, and
n is an integer of 1 or 2,
(2)

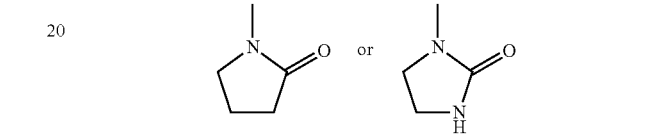

(3) a carbamoyl group optionally substituted by 1 or 2 C$_{1-6}$ alkyl,
(4) a carbamoylamino group or a mono- or di-C$_{1-6}$ alkyl-carbamoylamino group,
(5) a C$_{1-6}$ alkoxy-carbonyl group, and
(6) a C$_{1-6}$ alkyl group substituted by hydroxy;
R⁴ is
(1) a halogen atom,
(2) a C$_{1-6}$ alkoxy group optionally having 1 to 3 halogen atoms, or
(3) a C$_{1-6}$ alkyl group optionally having 1 to 3 substituents selected from a halogen atom and hydroxy; and
R² is a halogen atom or a C$_{1-6}$ alkyl group.
Of compound (I),
5-chloro-1-[5-chloro-2-(methylsulfonyl)benzyl]-2-imino-1,2-dihydropyridine-3-carboxamide (Example 1),
5-chloro-2-imino-1-[5-methyl-2-(methylsulfonyl)benzyl]-1,2-dihydropyridine-3-carboxamide (Example 8),
5-chloro-1-[3-chloro-5-(methylsulfonyl)benzyl]-2-imino-1,2-dihydropyridine-3-carboxamide (Example 12),
5-chloro-1-[5-chloro-2-(methylsulfinyl)benzyl]-2-imino-1,2-dihydropyridine-3-carboxamide (Example 14),
5-chloro-1-[4-chloro-3-(methylsulfonyl)benzyl]-2-imino-1,2-dihydropyridine-3-carboxamide (Example 15),
5-chloro-1-[5-chloro-2-(ethylsulfonyl)benzyl]-2-imino-1,2-dihydropyridine-3-carboxamide (Example 17),
5-chloro-1-[5-fluoro-2-(methylsulfonyl)benzyl]-2-imino-1,2-dihydropyridine-3-carboxamide (Example 18)
and a salt thereof and the like are preferable.
In another embodiment,
5-chloro-1-[5-chloro-2-(methylsulfonyl)benzyl]-2-imino-1,2-dihydropyridine-3-carboxamide (Example 1),
5-chloro-2-imino-1-[5-methyl-2-(methylsulfonyl)benzyl]-1,2-dihydropyridine-3-carboxamide (Example 8),
5-chloro-1-[3-chloro-5-(methylsulfonyl)benzyl]-2-imino-1,2-dihydropyridine-3-carboxamide (Example 12),
5-chloro-1-[5-chloro-2-(methylsulfinyl)benzyl]-2-imino-1,2-dihydropyridine-3-carboxamide (Example 14),
5-chloro-1-[4-chloro-3-(methylsulfonyl)benzyl]-2-imino-1,2-dihydropyridine-3-carboxamide (Example 15),
5-chloro-1-[5-chloro-2-(ethylsulfonyl)benzyl]-2-imino-1,2-dihydropyridine-3-carboxamide (Example 17), 5-chloro-1-[5-fluoro-2-(methylsulfonyl)benzyl]-2-imino-1,2-dihydropyridine-3-carboxamide (Example 18),
5-chloro-1-[2-(ethylsulfonyl)-5-fluorobenzyl]-2-imino-1,2-dihydropyridine-3-carboxamide (Example 24),
5-chloro-1-(5-chloro-2-sulfamoylbenzyl)-2-imino-1,2-dihydropyridine-3-carboxamide (Example 28),
5-chloro-1-[5-chloro-2-(2-oxopyrrolidin-1-yl)benzyl]-2-imino-1,2-dihydropyridine-3-carboxamide (Example 35)
and a salt thereof and the like are preferable.

Of these,
5-chloro-1-[5-chloro-2-(methylsulfonyl)benzyl]-2-imino-1,2-dihydropyridine-3-carboxamide (Example 1),
5-chloro-1-[5-chloro-2-(methylsulfinyl)benzyl]-2-imino-1,2-dihydropyridine-3-carboxamide (Example 14),
5-chloro-1-[5-fluoro-2-(methylsulfonyl)benzyl]-2-imino-1,2-dihydropyridine-3-carboxamide (Example 18),
5-chloro-1-[2-(ethylsulfonyl)-5-fluorobenzyl]-2-imino-1,2-dihydropyridine-3-carboxamide (Example 24),
5-chloro-1-(5-chloro-2-sulfamoylbenzyl)-2-imino-1,2-dihydropyridine-3-carboxamide (Example 28),
5-chloro-1-[5-chloro-2-(2-oxopyrrolidin-1-yl)benzyl]-2-imino-1,2-dihydropyridine-3-carboxamide (Example 35)
and a salt thereof and the like are particularly preferable.

Compound (I) does not encompass
5-chloro-1-{4-[(dimethylamino)sulfonyl]benzyl}-2-imino-1,2-dihydropyridine-3-carboxamide,
5-chloro-1-[3-(1-hydroxy-1-methylethyl)benzyl]-2-imino-1,2-dihydropyridine-3-carboxamide,
methyl 3-{[3-(aminocarbonyl)-5-chloro-2-iminopyridin-1(2H)-yl]methyl}benzoate,
1-[3-(aminocarbonyl)benzyl]-5-chloro-2-imino-1,2-dihydropyridine-3-carboxamide,
5-chloro-1-[4-chloro-2-(methylsulfonyl)benzyl]-2-imino-1,2-dihydropyridine-3-carboxamide,
5-chloro-2-imino-1-[4-(methylsulfonyl)benzyl]-1,2-dihydropyridine-3-carboxamide,
5-chloro-2-imino-1-[2-methoxy-5-(methylsulfonyl)benzyl]-1,2-dihydropyridine-3-carboxamide,
5-chloro-1-[2-chloro-4-(methylsulfonyl)benzyl]-2-imino-1,2-dihydropyridine-3-carboxamide,
5-chloro-1-{3-chloro-5-[(methylamino)carbonyl]benzyl}-2-imino-1,2-dihydropyridine-3-carboxamide,
5-chloro-1-[2-chloro-5-(methylsulfonyl)benzyl]-2-imino-1,2-dihydropyridine-3-carboxamide,
1-[3-(aminocarbonyl)-5-chlorobenzyl]-5-chloro-2-imino-1,2-dihydropyridine-3-carboxamide,
5-chloro-2-imino-1-[3-(methylsulfonyl)benzyl]-1,2-dihydropyridine-3-carboxamide, and
5-chloro-2-imino-1-(3-morpholin-4-ylbenzyl)-1,2-dihydropyridine-3-carboxamide.

When compound (I) or (I') is the form of a salt, examples of such salt include salts with inorganic bases, ammonium salts, salts with organic bases, salts with inorganic acids, salts with organic acids, salts with basic or acidic amino acids and the like.

Preferable examples of the salt with inorganic base include sodium salt, potassium salt and the like alkali metal salt; calcium salt, magnesium salt, barium salt and the like alkaline earth metal salt; aluminum salt and the like.

Preferable examples of the salt with organic base include a salt with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like.

Preferable examples of the salt with acidic amino acid include a salt with aspartic acid, glutamic acid and the like.

Of these, a pharmaceutically acceptable salt is preferable.

Compound (I) or (I') may be a hydrate, and hydrate, non-hydrate, solvate and non-solvate are encompassed in the scope of the present invention.

Compound (I) or (I') may be labeled with an isotope (e.g., $^3H$, $^{14}C$, $^{35}S$, $^{125}I$ and the like) or the like.

Compound (I) or (I') may also a deuterium conversion form wherein $^1H$ has been converted to $^2H(D)$.

When compound (I) or (I') has an asymmetric center, isomers such as enantiomer, diastereomer and the like may be present. Such isomers and a mixture thereof are all encompassed in the scope of the present invention. When an isomer due to conformation is present, such isomer and a mixture thereof are also encompassed in compound (I) of the present invention.

The production methods of compound (I) or a salt thereof of the present invention is explained in the following.

Compound (I) can be produced according to the following Method A' or a method analogous thereto. Starting material compounds in each step of the following production methods may be used in the form of a salt, and examples of such salt include those similar to the salts of compound (I).

[Method A]

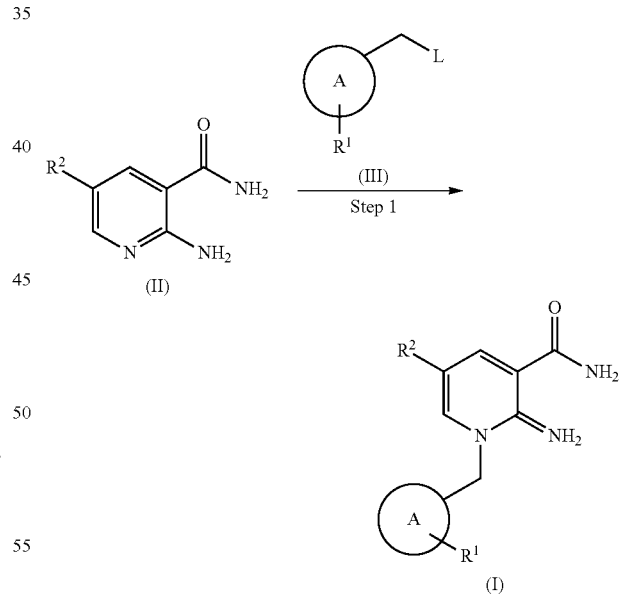

A compound represented by the formula (II) used as a starting material in this method can be produced according to a method known per se or a method analogous thereto, for example, the method described in J. Org. Chem., (1954), 19, 1633, Tetrahedron. Lett., (1994), 35(32), 5775, or the like.

A compound represented by the formula (III) wherein L is a leaving group, and ring $A^0$- and $R^{10}$ are as defined above, which is used as a starting material in this method, may be a commercially available product, which can be used directly or after isolation and purification, or can be produced according to a method known per se or a method analogous thereto.

(Step 1)

Compound (I) can be produced, for example, by reacting compound (II) with compound (III).

Examples of the "leaving group" for L include a halogen atom (e.g., chlorine atom, bromine atom, iodine atom and the like), a substituted sulfonyloxy group (e.g., a $C_{1-6}$ alkylsulfonyloxy group such as methanesulfonyloxy, ethanesulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy group and the like, and the like) and the like, and a halogen atom is particularly preferable.

This reaction is generally carried out in a solvent inert to the reaction.

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), dimethylacetamide (DMA) and the like; alcohols such as methanol, ethanol, propanol, tert-butanol, methoxyethanol and the like; ketones such as acetone and the like; nitriles such as acetonitrile and the like; sulfoxides such as dimethyl sulfoxide (DMSO) and the like; and a mixed solvent thereof.

The amount of compound (III) to be used is generally about 1 to about 5 mol, preferably about 1 to about 3 mol, per 1 mol of compound (II).

This reaction is generally carried out at about 0° C. to about 200° C., preferably about 20° C. to about 150° C. The reaction time of this reaction is generally about 0.5 hr to about 60 hr.

The thus-obtained compound (I) can be isolated and purified by known separation and purification means, for example, concentration, concentration under reduced pressure, solvent extraction, crystallization, recrystallization, phase transfer, chromatography and the like.

Of compound (I), a compound represented by the formula

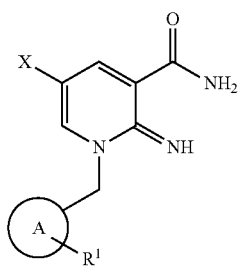

(I-A)

wherein X is a halogen atom, and other symbols are as defined above (hereinafter to be abbreviated as compound (I-A)) can be produced according to the following Method B' or a method analogous thereto. Starting material compounds in each step of the following production methods may be used in the form of a salt, and Examples of such salt include those similar to the salts of compound (I).

[Method B]

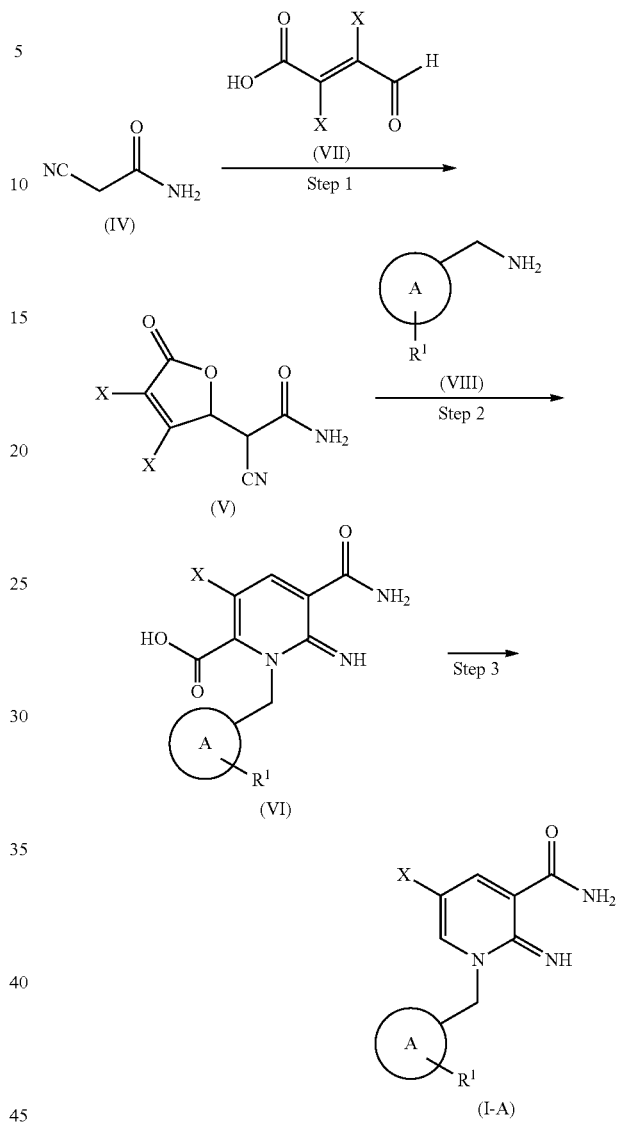

A compound represented by the formula (IV) and a compound represented by the formula (VIII), each of which is used as a starting material in this method, may be a commercially available product, which can be used directly or after isolation and purification, or can be produced according to a method known per se or a method analogous thereto.

A compound represented by the formula (VII) used as a starting material in this method can be produced according to a method known per se or a method analogous thereto, for example, the method described in J. Am. Chem. Soc., 1953, 75, 1909, or the like.

(Step 1)

This step is a step of reacting compound (IV) with aldehyde (VII) wherein X is a halogen atom, in the presence of a base, to produce compound (V).

Examples of the "halogen atom" for X include chlorine atom, bromine atom, iodine atom and the like.

This reaction is generally carried out in a solvent inert to the reaction.

Examples of the base used for this reaction include alkali metal salts such as potassium hydroxide, sodium hydroxide, sodium carbonate, potassium carbonate and the like; amines such as pyridine, trimethylamine, N,N-dimethylaniline, 1,8-diazabicyclo[5.4.0]undec-7-en (DBU) and the like; metal alkoxides such as sodium methoxide, sodium ethoxide, potassium tert-butoxide and the like; metal hydrides such as sodium hydride, potassium hydride and the like, and the like.

The amount of the base to be used is generally about 1 to about 20 mol, preferably about 1 to about 3 mol, per 1 mol of compound (IV).

The amount of aldehyde (VII) to be used is generally about 1 to about 5 mol, preferably about 1 to about 3 mol, per 1 mol of compound (IV).

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; sulfoxides such as dimethyl sulfoxide (DMSO) and the like; water; and a mixed solvent thereof.

This reaction is generally carried out at about −50° C. to about 200° C., preferably about −10° C. to about 100° C. The reaction time of this reaction is generally about 0.5 hr to about 60 hr.

The thus-obtained compound (V) can be isolated and purified by known separation and purification means, for example, concentration, concentration under reduced pressure, solvent extraction, crystallization, recrystallization, phase transfer, chromatography and the like.

(Step 2)

This step is a step of subjecting compound (V) to cyclization with amine (VIII) in an inert solvent, in the presence of a base to produce compound (VI).

The amount of amine (VIII) to be used is generally about 1 to about 10 mol, preferably about 1 to about 3 mol, per 1 mol of compound (V).

Examples of the base used for this reaction include alkali metal salts such as potassium hydroxide, sodium hydroxide, sodium carbonate, potassium carbonate and the like; amines such as pyridine, trimethylamine, triethylamine, N,N-dimethylaniline, 1,8-diazabicyclo[5.4.0]undec-7-en (DBU) and the like; metal alkoxides such as sodium methoxide, sodium ethoxide, potassium tert-butoxide and the like; organic metals such as n-butyllithium, lithiumdiisopropylamide (LDA) and the like; metal hydrides such as sodium hydride, potassium hydride and the like; and the like.

The amount of the base to be used is generally about 1 to about 10 mol, preferably about 1 to about 3 mol, per 1 mol of compound (V).

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; ketones such as acetone and the like; nitriles such as acetonitrile and the like; sulfoxides such as dimethyl sulfoxide (DMSO) and the like; water; and a mixed solvent thereof.

This reaction is generally carried out at about −50° C. to about 200° C., preferably about −10° C. to about 100° C. The reaction time of this reaction is generally about 0.1 hr to about 60 hr.

The thus-obtained compound (VI) can be isolated and purified by known separation and purification means, for example, concentration, concentration under reduced pressure, solvent extraction, crystallization, recrystallization, phase transfer, chromatography and the like. In addition, compound (VI) may be used in the form of a reaction mixture in the next step (Step 3) without isolation and purification.

(Step 3)

This step is a step of by subjecting a compound represented by the formula (VI) to a decarboxylation reaction to produce compound (I-A). In this decarboxylation reaction, a known decarboxylation reaction can be used. For example, methods such as heating, using an acid or a base with heating if necessary, and the like can be used. The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; sulfoxides such as dimethyl sulfoxide (DMSO) and the like; nitriles such as acetonitrile and the like; organic acids such as acetic acid, trifluoroacetic acid and the like; water; and a mixed solvent thereof.

Examples of the base to be used for this reaction include alkali metal salts such as potassium hydroxide, sodium hydroxide, sodium carbonate, potassium carbonate and the like; amines such as pyridine, trimethylamine, N,N-dimethylaniline, 1,8-diazabicyclo[5.4.0]undec-7-en (DBU) and the like; metal alkoxides such as sodium methoxide, sodium ethoxide, potassium tert-butoxide and the like; metal hydrides such as sodium hydride, potassium hydride and the like, and the like. Examples of the acid include inorganic acids such as hydrochloric acid, sulfuric acid, hydrobromic acid and the like; organic acids such as acetic acid, trifluoroacetic acid and the like, and the like.

The amount of the base or acid to be used is generally about 1 to about 100 mol, preferably about 1 to about 10 mol, per 1 mol of compound (VI).

This reaction is generally carried out at about −50° C. to about 200° C., preferably about −10° C. to about 100° C. The reaction time of this reaction is generally about 0.1 hr to about 60 hr.

The thus-obtained compound (I-A) can be isolated and purified by known separation and purification means, for example, concentration, concentration under reduced pressure, solvent extraction, crystallization, recrystallization, phase transfer, chromatography and the like.

The production methods of compound (I') or a salt thereof of the present invention are explained in the following.

Compound (I') can be produced according to the following Method A' or a method analogous thereto. Starting material compounds in each step of the following production methods may be used in the form of a salt, and examples of such salt include those similar to the salts of compound (I').

[Method A']

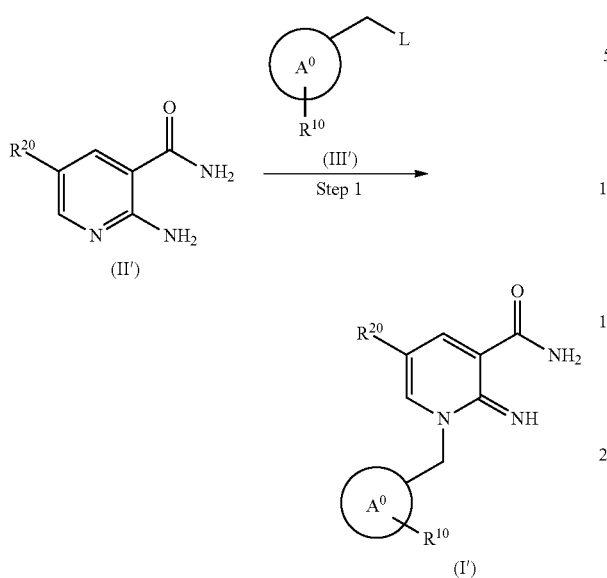

A compound represented by the formula (II') used as a starting material in this method can be produced according to a method known per se or a method analogous thereto, for example, the method described in J. Org. Chem., (1954), 19, 1633, Tetrahedron. Lett., (1994), 35(32), 5775, or the like.

A compound represented by the formula (III') wherein L is a leaving group, and ring $A^0$- and $R^{10}$ are as defined above, which is used as a starting material in this method, may be a commercially available product, which can be used directly or after isolation and purification, or can be produced according to a method known per se or a method analogous thereto.

(Step 1)

Compound (I') can be produced, for example, by reacting compound (II') with compound (III').

Examples of the "leaving group" for L include a halogen atom (e.g., chlorine atom, bromine atom, iodine atom and the like), a substituted sulfonyloxy group (e.g., a $C_{1-6}$ alkylsulfonyloxy group such as methanesulfonyloxy, ethanesulfonyloxy and the like; a $C_{6-14}$ arylsulfonyloxy group such as benzenesulfonyloxy, p-toluenesulfonyloxy and the like; a $C_{7-16}$ aralkylsulfonyloxy group such as benzylsulfonyloxy group and the like, and the like) and the like, and a halogen atom is particularly preferable.

This reaction is generally carried out in a solvent inert to the reaction.

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), dimethylacetamide (DMA) and the like; alcohols such as methanol, ethanol, propanol, tert-butanol, methoxyethanol and the like; ketones such as acetone and the like; nitriles such as acetonitrile and the like; sulfoxides such as dimethyl sulfoxide (DMSO) and the like; and a mixed solvent thereof.

The amount of compound (III') to be used is generally about 1 to about 5 mol, preferably about 1 to about 3 mol, per 1 mol of compound (II').

This reaction is generally carried out at about 0° C. to about 200° C., preferably about 20° C. to about 150° C. The reaction time of this reaction is generally about 0.5 hr to about 60 hr.

The thus-obtained compound (I') can be isolated and purified by known separation and purification means, for example, concentration, concentration under reduced pressure, solvent extraction, crystallization, recrystallization, phase transfer, chromatography and the like.

Of compound (I'), a compound represented by the formula

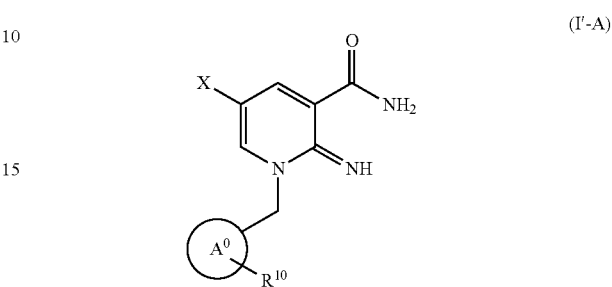

wherein X is a halogen atom, and other symbols are as defined above (hereinafter to be abbreviated as compound (I'-A)) can be produced according to the following Method B' or a method analogous thereto. Starting material compounds in each step of the following production methods may be used in the form of a salt, and Examples of such salt include those similar to the salts of compound (I').

[Method B']

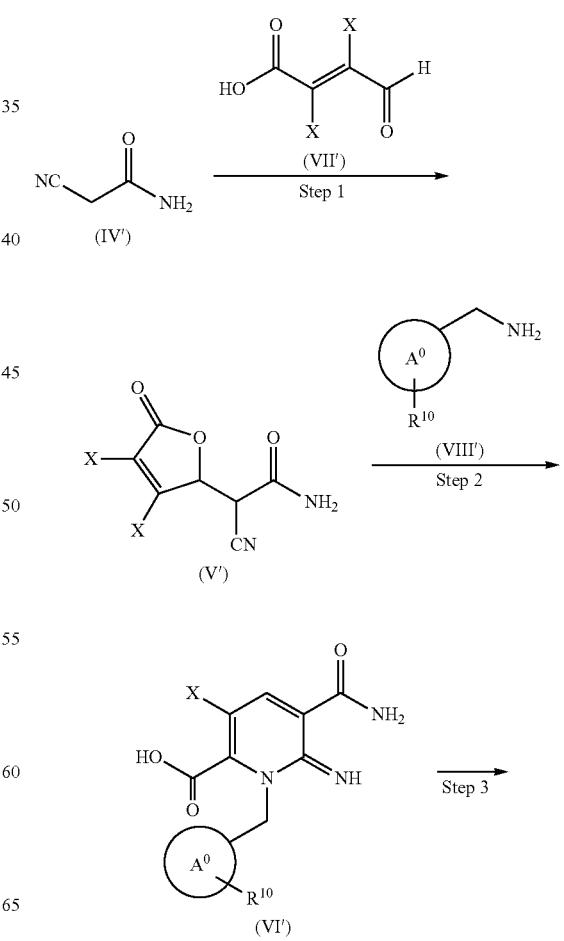

-continued

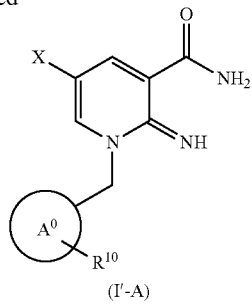

(I'-A)

A compound represented by the formula (IV') and a compound represented by the formula (VIII'), each of which is used as a starting material in this method, may be a commercially available product, which can be used directly or after isolation and purification, or can be produced according to a method known per se or a method analogous thereto.

A compound represented by the formula (VII') used as a starting material in this method can be produced according to a method known per se or a method analogous thereto, for example, the method described in J. Am. Chem. Soc., 1953, 75, 1909, or the like.

(Step 1)

This step is a step of reacting compound (IV') with aldehyde (VII') wherein X is a halogen atom, in the presence of a base, to produce compound (V').

Examples of the "halogen atom" for X include chlorine atom, bromine atom, iodine atom and the like.

This reaction is generally carried out in a solvent inert to the reaction.

Examples of the base used for this reaction include alkali metal salts such as potassium hydroxide, sodium hydroxide, sodium carbonate, potassium carbonate and the like; amines such as pyridine, trimethylamine, N,N-dimethylaniline, 1,8-diazabicyclo[5.4.0]undec-7-en (DBU) and the like; metal alkoxides such as sodium methoxide, sodium ethoxide, potassium tert-butoxide and the like; metal hydrides such as sodium hydride, potassium hydride and the like, and the like.

The amount of the base to be used is generally about 1 to about 20 mol, preferably about 1 to about 3 mol, per 1 mol of compound (IV').

The amount of aldehyde (VII') to be used is generally about 1 to about 5 mol, preferably about 1 to about 3 mol, per 1 mol of compound (IV').

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; sulfoxides such as dimethyl sulfoxide (DMSO) and the like; water; and a mixed solvent thereof.

This reaction is generally carried out at about −50° C. to about 200° C., preferably about −10° C. to about 100° C. The reaction time of this reaction is generally about 0.5 hr to about 60 hr.

The thus-obtained compound (V') can be isolated and purified by known separation and purification means, for example, concentration, concentration under reduced pressure, solvent extraction, crystallization, recrystallization, phase transfer, chromatography and the like.

(Step 2)

This step is a step of subjecting compound (V') to cyclization with amine (VIII') in an inert solvent, in the presence of a base to produce compound (VI').

The amount of amine (VIII') to be used is generally about 0.5 to about 10 mol, preferably about 1 to about 10 mol, more preferably about 1 to about 3 mol, per 1 mol of compound (V').

Examples of the base used for this reaction include alkali metal salts such as potassium hydroxide, sodium hydroxide, sodium carbonate, potassium carbonate and the like; amines such as pyridine, trimethylamine, triethylamine, N,N-dimethylaniline, 1,8-diazabicyclo[5.4.0]undec-7-en (DBU), N,N-diisopropylethylamine and the like; metal alkoxides such as sodium methoxide, sodium ethoxide, potassium tert-butoxide and the like; organic metals such as n-butyllithium, lithiumdiisopropylamide (LDA) and the like; metal hydrides such as sodium hydride, potassium hydride and the like, and the like.

The amount of the base to be used is generally about 0.5 to about 10 mol, preferably about 1 to about 10 mol, more preferably about 1 to about 3 mol, per 1 mol of compound (V').

The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; ketones such as acetone and the like; nitriles such as acetonitrile and the like; sulfoxides such as dimethyl sulfoxide (DMSO) and the like; water; and a mixed solvent thereof.

This reaction is generally carried out at about −50° C. to about 200° C., preferably about −10° C. to about 100° C. The reaction time of this reaction is generally about 0.1 hr to about 60 hr.

The thus-obtained compound (VI') can be isolated and purified by known separation and purification means, for example, concentration, concentration under reduced pressure, solvent extraction, crystallization, recrystallization, phase transfer, chromatography and the like. In addition, compound (VI') may be used in the form of a reaction mixture in the next step (Step 3) without isolation and purification.

(Step 3)

This step is a step of by subjecting a compound represented by the formula (VI') to a decarboxylation reaction to produce compound (I'-A). In this decarboxylation reaction, a known decarboxylation reaction can be used. For example, methods such as heating, using an acid or a base with heating if necessary, and the like can be used. The solvent for this reaction is not particularly limited as long as the reaction proceeds. Examples thereof include aromatic hydrocarbons such as benzene, toluene, xylene and the like; ethers such as tetrahydrofuran, dimethoxyethane, dioxane, diethyl ether and the like; amides such as N,N-dimethylformamide (DMF), N,N-dimethylacetamide (DMA), 1-methyl-2-pyrrolidone and the like; alcohols such as methanol, ethanol, propanol, tert-butanol, methoxyethanol and the like; sulfoxides such as dimethyl sulfoxide (DMSO) and the like; nitriles such as acetonitrile and the like; organic acids such as acetic acid, trifluoroacetic acid and the like; water; and a mixed solvent thereof.

Examples of the base to be used for this reaction include alkali metal salts such as potassium hydroxide, sodium hydroxide, sodium carbonate, potassium carbonate and the like; amines such as pyridine, trimethylamine, N,N-dimethylaniline, 1,8-diazabicyclo[5.4.0]undec-7-en (DBU), N,N-diisopropylethylamine and the like; metal alkoxides such as sodium methoxide, sodium ethoxide, potassium tert-butoxide and the like; metal hydrides such as sodium hydride, potassium hydride and the like, and the like. Examples of the acid include inorganic acids such as hydrochloric acid, sulfuric acid, hydrobromic acid and the like; organic acids such as acetic acid, trifluoroacetic acid and the like, and the like.

The amount of the base or acid to be used is generally about 1 to about 100 mol, preferably about 1 to about 10 mol, per 1 mol of compound (VI').

This reaction is generally carried out at about −50° C. to about 200° C., preferably about −10° C. to about 100° C. The reaction time of this reaction is generally about 0.1 hr to about 60 hr.

The thus-obtained compound (I'-A) can be isolated and purified by known separation and purification means, for example, concentration, concentration under reduced pressure, solvent extraction, crystallization, recrystallization, phase transfer, chromatography and the like.

In each of the reactions for the synthesis of the objective compounds and the starting materials, when the starting compounds have an amino group, a carboxyl group or a hydroxyl group as a substituent, such groups may be protected with the protecting groups which are generally used in peptide chemistry etc. In such a case, if necessary, such protecting groups can be removed to obtain the objective compounds after the reactions.

Such a protecting group includes, for example, protecting groups described in "Protective Groups in Organic Synthesis, $3^{rd}$ Ed. (1999)", edited by Theodara W. Greene, Peter G. M. Wuts, published by Wiley-Interscience.

Examples of the protecting group for the amino group include a formyl group, a $C_{1-6}$ alkyl-carbonyl group (e.g., an acetyl group, a propionyl group etc.), a phenylcarbonyl group, a $C_{1-6}$ alkyl-oxycarbonyl group (e.g., methoxycarbonyl group, an ethoxycarbonyl group etc.), an aryloxycarbonyl group (e.g., a phenyloxycarbonyl group etc.), a $C_{7-10}$ aralkyl-carbonyl group (e.g., a benzyloxycarbonyl group etc.), a benzyl group, a benzhydryl group, a trityl group, a phthaloyl etc., each of which may have substituent(s). Examples of such substituent include a halogen atom (e.g., a fluorine atom, a chlorine atom, a bromine atom, an iodine atom etc.), a $C_{1-6}$ alkyl-carbonyl group (e.g., an acetyl group, a propionyl group, a butylcarbonyl group etc.), a nitro group and the like. The number of substituent(s) is 1 to 3.

Examples of the protecting group for the carboxyl group include a $C_{1-6}$ alkyl group (e.g., a methyl group, an ethyl group, a n-propyl group, an i-propyl group, a n-butyl group, a tert-butyl group etc.), a phenyl group, a trityl group, a silyl group and the like, each of which may have substituent(s). Examples of these substituents include a halogen atom (a fluorine atom, a chlorine atom, a bromine atom, an iodine atom), a formyl group, a $C_{1-6}$ alkyl-carbonyl group (e.g., an acetyl group, a propionyl group, a butylcarbonyl group etc.), a nitro group and the like. The number of substituent(s) is 1 to 3.

Examples of the hydroxyl-protecting group include a $C_{1-6}$ alkyl group (e.g., a methyl group, an ethyl group, a n-propyl group, an i-propyl group, a n-butyl group, a tert-butyl group etc.), a phenyl group, a $C_{7-10}$ aralkyl group (e.g., a benzyl group etc.), a formyl group, $C_{1-6}$ alkyl-carbonyl group (e.g., an acetyl group, a propionyl group etc.), an aryloxycarbonyl group (e.g., a phenyloxycarbonyl group etc.), a $C_{7-10}$ aralkyl-carbonyl group (e.g., a benzyloxycarbonyl group etc.), a pyranyl group, a furanyl group, a silyl group and the like, each of which may have substituent(s). Examples of these substituents include a halogen atom (a fluorine atom, a chlorine atom, a bromine atom, an iodine atom), a $C_{1-6}$ alkyl group, a phenyl group, a $C_{7-10}$ aralkyl group, a nitro group and the like. The number of substituent(s) is 1 to 4.

Such protecting groups can be removed by a known method or the method described in "Protective Groups in Organic Synthesis, $3^{rd}$ Ed. (1999)", edited by Theodora W. Greene, Peter G. M. Wuts, published by Wiley-Interscience, or the like, or an analogous method thereto. For example, treatment with an acid, a base, reduction, ultraviolet radiation, hydrazine, phenylhydrazine, sodium N-methyldithiocarbamate, tetrabutylammonium fluoride, palladium acetate or the like, can be used.

In the above-mentioned methods, when compound (I) or compound (I') is obtained as a free compound, it can form a salt with, for example, inorganic acid (e.g., hydrochloric acid, sulfuric acid, hydrobromic acid and the like), organic acid (e.g., methanesulfonic acid, benzenesulfonic acid, toluenesulfonic acid, oxalic acid, fumaric acid, maleic acid, tartaric acid and the like), inorganic base (e.g., alkali metals such as sodium, potassium and the like, alkaline earth metals such as calcium, magnesium and the like, aluminum, ammonium and the like) or organic base (e.g., trimethylamine, triethylamine, pyridine, picoline, ethanolamine, diethanolamine, triethanolamine, dicyclohexylamine, N,N'-dibenzylethylenediamine and the like) and the like according to a conventional method. When compound (I) (or compound (I')) is obtained in the form of a salt, it can also be converted to a free compound or other salt according to a conventional method.

In addition, when the starting compound forms a salt in each of the above-mentioned reactions, the compound may be used as a salt. Such salt includes, for example, those exemplified as the salt of compound (I) (or compound (I')).

Compound (I) (or compound (I')) thus prepared by such methods, can be isolated and purified by a typical separation means such as recrystallization, distillation, chromatography and the like.

When compound (I) (or compound (I')) includes an optical isomer, a stereoisomer, a regioisomer and a rotamer, these are also included in the scope of compound (I) (or compound (I')), and can be obtained as single products according to synthesis and separation methods known per se (e.g., concentration, solvent extraction, column chromatography, recrystallization etc.). For example, when compound (I) (or compound (I')) has an optical isomer, the optical isomer resolved from this compound is also encompassed in compound (I) (or compound (I')).

The optical isomer can be prepared by a method known per se. To be specific, an optically active synthetic intermediate is used, or the final racemate product is subjected to optical resolution according to a conventional method to give an optical isomer.

The method of optical resolution may be a method known per se, such as a fractional recrystallization method, a chiral column method, a diastereomer method etc.

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer, etc.) and organic solvents (e.g., ethanol, methanol, isopropanol, acetonitrile, trifluoroacetic acid, diethylamine etc.) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to separate an optically active reagent moiety, whereby an optical isomer is obtained. For example, when compound (I) (or compound (I')) contains hydroxy, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) (or compound (I')) has a carboxyl group, this compound and an optically active amine or an optically active alcohol are subjected to condensation reaction to give diastereomers of the amide compound or the ester compound, respectively. The separated diastereomer is converted to an optical isomer of the original compound by acid hydrolysis or base hydrolysis.

Compound (I) (or compound (I')) may be in the form of crystals.

The crystal of compound (I) (or compound (I')) can be prepared by crystallization of compound (I) (or compound (I')) by a crystallization method known per se.

Examples of the crystallization method include a method of crystallization from a solution, a method of crystallization from vapor, a method of crystallization from the melts and the like.

The "crystallization from a solution" is typically a method of shifting a non-saturated state to supersaturated state by varying factors involved in solubility of compounds (solvent composition, pH, temperature, ionic strength, redox state etc.) or the amount of solvent. To be specific, for example, a concentration method, a cold removing method, a reaction method (a diffusion method, an electrolysis method), a hydrothermal growth method, a flux method and the like. Examples of the solvent to be used include aromatic hydrocarbons (e.g., benzene, toluene, xylene etc.), halogenated hydrocarbons (e.g., dichloromethane, chloroform etc.), saturated hydrocarbons (e.g., hexane, heptane, cyclohexane etc.), ethers (e.g., diethyl ether, diisopropyl ether, tetrahydrofuran, dioxane etc.), nitriles (e.g., acetonitrile etc.), ketones (e.g., acetone etc.), sulfoxides (e.g., dimethyl sulfoxide etc.), acid amides (e.g., N,N-dimethylformamide etc.), esters (e.g., ethyl acetate etc.), alcohols (e.g., methanol, ethanol, isopropyl alcohol etc.), water and the like. These solvents are used alone or in a combination of two or more at a suitable ratio (e.g., 1:1 to 1:100 (a volume ratio)). Where necessary, a seed crystal can also be used.

The "crystallization from vapor" is, for example, a vaporization method (a sealed tube method, a gas stream method), a gas phase reaction method, a chemical transportation method and the like.

The "crystallization from the melts" is, for example, a normal freezing method (a Czochralski method, a temperature gradient method and a Bridgman method), a zone melting method (a zone leveling method and a floating zone method), a special growth method (a VLS method and a liquid phase epitaxy method) and the like.

Preferable examples of the crystallization method include a method of dissolving compound (I) (or compound (I')) in a suitable solvent (e.g., alcohols such as methanol, ethanol etc. and the like) at a temperature of 20 to 120° C., and cooling the resulting solution to a temperature not higher than the temperature of dissolution (e.g., 0 to 50° C., preferably 0 to 20° C.) and the like.

The thus obtained crystals of compound (I) (or compound (I')) can be isolated, for example, by filtration and the like.

As an analysis method of the obtained crystal, crystal analysis by powder X-ray diffraction is generally employed. Moreover, as a method for determining the crystal orientation, a mechanical method, an optical method and the like can also be mentioned.

The crystals of compound (I) (or compound (I')) obtained in the above-mentioned production method (hereinafter to be abbreviated as "crystal of the present invention") has high purity, high quality and low hygroscopicity, is free of denaturation even after a long-term preservation under normal conditions, and is extremely superior in stability. The crystal is also superior in biological properties (e.g., in vivo kinetics (absorbability, distribution, metabolism, excretion), efficacy expression etc.), and is extremely useful as a pharmaceutical agent.

In the present specification, the melting point means that measured using, for example, a micromelting point apparatus (Yanako, MP-500D) or a DSC (differential scanning calorimetry) device (SEIKO, EXSTAR 6000) and the like.

The prodrug of compound (I) (or compound (I')) means a compound which is converted to compound (I) (or compound (I')) with a reaction due to an enzyme, gastric acid, etc. under the physiological condition in the living body, that is, a compound which is converted to compound (I) (or compound (I')) by enzymatic oxidation, reduction, hydrolysis, etc.; a compound which is converted to compound (I) (or compound (I')) by hydrolysis etc. due to gastric acid, and the like. A prodrug of compound (I) (or compound (I')) may be a compound obtained by subjecting an amino group in compound (I) (or compound (I')) to an acylation, alkylation or phosphorylation (e.g., a compound obtained by subjecting an amino group in compound (I) (or compound (I')) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting a hydroxy group in compound (I) (or compound (I')) to an acylation, alkylation, phosphorylation or boration (e.g., a compound obtained by subjecting a hydroxy group in compound (I) (or compound (I')) to an acetylation, palmitoylation, propanoylation, pivaloylation, succinylation, fumarylation, alanylation, dimethylaminomethylcarbonylation, etc.); a compound obtained by subjecting a carboxyl group in compound (I) (or compound (I')) to an esterification or amidation (e.g., a compound obtained by subjecting a carboxyl group in compound (I) (or compound (I')) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) (or compound (I')) by a method known per se.

A prodrug for compound (I) (or compound (I')) may also be one which is converted into compound (I) (or compound (I')) under a physiological condition, such as those described in IYAKUHIN no KAIHATSU (Development of Pharmaceuticals), Vol. 7, Design of Molecules, p. 163-198, 1990, Published by HIROKAWA SHOTEN.

Compound (I), a salt thereof and a prodrug thereof, as well as compound (I'), a salt thereof and a prodrug thereof are hereinafter collectively abbreviated as "the compound of the present invention".

The compound of the present invention has a superior $\alpha_{1D}$ adrenergic receptor antagonistic action. Specifically, the compound of the present invention is a compound having a selective $\alpha_{1D}$ adrenergic receptor antagonistic action. The selective $\alpha_{1D}$ adrenergic receptor antagonistic action here means the presence of an antagonistic activity at least 10-fold or above for $\alpha_{1A}$ adrenergic receptor, and at least 10-fold or above for $\alpha_{1B}$ adrenergic receptor. Since the compound of the present invention has a selective $\alpha_{1D}$ adrenergic receptor antagonistic action, it decreases a blood pressure lowering effect and the like considered to be based on the antagonistic action on the $\alpha_{1A}$ receptor or $\alpha_{1B}$ receptor. Therefore, the compound of the present invention is considered to provide a pharmaceutical agent with few side effects.

In addition, since the compound of the present invention shows low toxicity (e.g., cardiotoxicity (e.g., human ether-a-go-go related gene (HERG) inhibitory activity), phospholipidosis (PLsis), acute toxicity, chronic toxicity, genotoxicity, reproductive toxicity), drug-drug interaction, carcinogenicity, phototoxicity etc.), it can be safely administered to a mammal (e.g., mouse, rat, hamster, rabbit, cat, dog, bovine, sheep, monkey, human etc.).

Moreover, the compound of the present invention is superior in pharmacokinetics (e.g., absorbability, clearance etc.).

Based on the $\alpha_{1D}$ adrenergic receptor antagonistic action, the compound of the present invention is useful as a drug for the prophylaxis or treatment of any $\alpha_{1D}$ adrenergic receptor associated diseases in mammals (e.g., mouse, rat, hamster, rabbit, cat, dog, bovine, sheep, monkey, human etc.), for example, (1) lower urinary tract diseases (including all diseases having lower urinary tract symptom as described in the following, e.g., overactive bladder, benign prostatic hyperplasia, interstitial cystitis, chronic prostatitis etc.) storage symptom (daytime urinary frequency, nocturia, urinary urgency, urinary incontinence, stress urinary incontinence, urge urinary incontinence, mixed urinary incontinence, enuresis, nocturnal enuresis, continuous urinary incontinence, other urinary incontinence, enhanced, decreased or missing bladder sensation etc.), voiding symptom (weak urinary stream or slow stream), split urinary stream (or splitting stream), spraying stream, intermittent urinary stream (or intermittent stream), voiding postponement (or hesitancy), straining at urination (or straining), terminal dribbling (or terminal dribble) etc.), post-micturition symptom (sense of residual urine, post-micturition dribble etc.), symptom due to sexual intercourse (coital pain, vaginal dryness, urinary incontinence etc.), symptom due to pelvic organ prolapse (foreign body sensation, lumbago etc.), genital organ pain or lower urinary tract pain (cystalgia, urethral pain, pudendalgia, vaginodynia, scrotal pain, perineal pain, pelvic pain etc.), genital organ or urinary tract pain syndrome (cystalgia syndrome, urethral pain syndrome, pudendalgia syndrome, vaginal syndrome, scrotal pain syndrome, perineal pain syndrome, pelvic pain syndrome etc.), symptom syndrome suggesting lower urinary tract dysfunction (overactive bladder syndrome, lower urinary tract symptom suggesting bladder outlet obstruction etc.), polyuria, urolithiasis (urinary duct, urethra) and the like, (2) metabolic diseases [for example, diabetes (insulin dependent diabetes, diabetic complications, diabetic retinopathy, diabetic microangiopathy, diabetic neuropathy etc.), impaired glucose tolerance, obesity, benign prostatic hyperplasia, sexual dysfunction and the like], (3) central nervous system diseases [for example, neurodegenerative diseases (e.g., Alzheimer's disease, Down's disease, Parkinson's disease, Creutzfeldt-Jakob disease, amyotrophic lateral sclerosis (ALS), Huntington chorea, diabetic neuropathy, multiple sclerosis etc.), mental diseases (e.g., schizophrenia, depression, mania, anxiety neurosis, obsessive-compulsive neurosis, panic disorder, epilepsy, alcohol dependence, drug dependence, anxiety, anxious mental state, emotional abnormality, cyclothymia, nervous erethism, autism, faint, addiction, low sex drive etc.), disorders such as central nervous system and peripheral nerve disorders (e.g., head trauma, spinal trauma, brain edema, disorders of sensory function, abnormality of sensory function, disorders of autonomic nervous function, abnormality of autonomic nervous function, whiplash injury etc.), memory disorders (e.g., senile dementia, amnesia, cerebrovascular dementia etc.), cerebrovascular disorder (e.g., cerebral hemorrhage, cerebral infarction and the like and sequelae or complication thereof, asymptomatic cerebrovascular accident, transient cerebral ischemic attack, hypertensive encephalopathia, blood-brain barrier disorder, etc.), recurrence and sequelae of cerebrovascular disorders (e.g., neural symptoms, mental symptoms, subjective symptoms, disorders of daily living activities etc.), central nervous system hypofunction after brain blood vessel occlusion, disorder or abnormality of autoregulation ability of brain circulation or renal circulation etc.], sleep disorder, (4) genital insufficiency diseases [for example, male erectile dysfunction, dyssermia, female genital insufficiency etc.], (5) gastrointestinal diseases [for example, irritable bowel syndrome, inflammatory bowel disease, ulcerative colitis, Crohn's disease, abnormality (e.g., gastritis, gastric ulcer etc.) caused by urease positive herical gram negative bacteria (e.g., *Helicobacter pylori* etc.), gastric cancer, postgastrostomy disorder, dyspepsia, esophageal ulcer, pancreatitis, colon polyp, cholelithiasis, hemorrhoids, peptic ulcer, situational ileitis, gluttony, constipation, diarrhea, borborygmus etc.], (6) inflammatory or allergic diseases [for example, allergic rhinitis, conjunctivitis, gastrointestinal allergy, pollinosis, anaphylaxis, dermatitis, herpes, psoriasis, bronchitis, expectoration, retinopathy, postoperative and posttraumatic inflammation, regression of puffiness, pharyngitis, cystitis, meningitidis, inflammatory ophthalmic diseases etc.], (7) osteoarthropathy diseases [for example, rheumatoid arthritis (chronic rheumatoid arthritis), arthritis deformans, rheumatoid myelitis, osteoporosis, abnormal growth of cells, bone fracture, bone refracture, osteomalacia, osteopenia, osseous Behcet's disease, rigid myelitis, articular tissue destruction by gonarthrosis deformans and similar diseases thereto etc.], (8) respiratory diseases [for example, cold syndrome, pneumonia, asthma, pulmonary hypertension, pulmonary thrombi/pulmonary obliteration, pulmonary sarcoidosis, pulmonary tuberculosis, interstitial pneumonia, silicosis, adult respiratory distress syndrome, chronic obliterative pulmonary diseases, cough etc.], (9) infectious diseases [HIV infectious diseases, virus infectious diseases due to cytomegalo virus, influenza virus, herpes virus and the like, rickettsia infectious diseases, bacterial infectious diseases, sexually-transmitted diseases, carinii pneumonia, *helicobacter pylori* infectious disease, systemic fungal infectious diseases, tuberculosis, invasive staphylococcal infectious diseases, acute viral encephalitis, acute bacterial meningitidis, AIDS encephalitis, septicemia, sepsis, sepsis gravis, septic shock, endotoxin shock, toxic shock syndromes etc.],

(10) cancers [for example, primary, metastatic or recurrent breast cancer, prostatic cancer, pancreatic cancer, gastric cancer, lung cancer, colorectal cancer (colon cancer, rectal cancer, anal cancer), esophagus cancer, duodenal cancer, head and neck cancer (cancer of the tongue, pharynx cancer, laryngeal cancer), brain tumor, schwannoma, non-small cell lung cancer, small cell lung cancer, liver cancer, kidney cancer, biliary tract cancer, uterus cancer (endometrial cancer, cancer of the uterine cervix), ovarian cancer, urinary bladder cancer, skin cancer, Hemangioma, malignant lymphoma, malignant melanoma, thyroid cancer, bone tumor, vascular fibroma, retinosarcoma, penile cancer, solid cancer in childhood, Kaposi's sarcoma, Kaposi's sarcoma caused by AIDS, maxillary tumor, fibrous histiocytoma, leiomyosarcoma, rhabdomyosarcoma, liposarcoma, fibroid tumors of the uterus, osteoblastoma, osteosarcoma, chondrosarcoma, cancerous mesothelioma, tumors such as leukemia, Hodgkin's disease etc.],

(11) circulatory diseases [for example, acute coronary artery syndromes (e.g., acute myocardial infarction, unstable angina etc.), peripheral arterial obstruction, Raynaud's disease; Buerger disease; restenosis after coronary-artery intervention (percutaneous transluminal coronary angioplasty (PTCA), directional coronary atherectomy (DCA), stenting etc.), restenosis after coronary-artery bypass operation, restenosis after intervention (angioplasty, atherectomy, stenting etc.) or bypass operation in other peripheral artery, ischemic cardiac diseases (e.g., myocardial infarction, angina etc.), myocarditis, intermittent claudication, lacunar infarction, arteriosclerosis (e.g., atherosclerosis etc.), cardiac failure (acute cardiac failure, chronic cardiac failure accompanied by congestion), arrhythmia, progress of atherosclerotic plaque, thrombosis, hypertension, hypertensive tinnitus; hypotension etc.],

(12) pain [for example, headache, migraine, neuralgia and pelvic visceral pain including cystalgia etc.],

(13) autoimmune diseases [for example, collagen disease, systemic lupus erythematosus, scleroderma, polyarteritis, myasthenia gravis, multiple sclerosis, Sjogren's syndrome, Behcet's disease etc.],

(14) hepatic diseases [e.g., hepatitis (including chronic hepatitis), cirrhosis, interstitial hepatic diseases etc.],

(15) pancreatic diseases [e.g., pancreatitis (including chronic pancreatitis) etc.],

(16) renal diseases [e.g., nephritis, glomerulonephritis, glomerulosclerosis, renal failure, thrombotic microangiopathy, dialysis complications, organ disorders including nephropathia by radiation, diabetic nephropathy etc.],

(17) endocrine diseases [e.g., Addison's disease, Cushing's syndrome, melanocytoma, primary aldosteronism etc.],

(18) other diseases such as (a) transplant rejection [e.g., posttransplantational rejection, posttransplantational polycythemia, hypertension, organ disorder and/or vascular hypertrophy, graft-versus-host disease etc.], (b) abnormality in characteristic of blood and/or blood components [e.g., enhancement in platelet aggregation, abnormality of erythrocyte deformability, enhancement in leukocyte adhesiveness, increase in blood viscosity, polycythemia, vascular peliosis, autoimmune hemolytic anemia, disseminated intravascular coagulation syndrome (DIC), multiple myelopathy etc.], (c) gynecologic diseases [e.g., climacteric disorder, gestational toxicosis, endometriosis, hysteromyoma, ovarian disease, mammary disease, premenstrual syndrome, pelvic organ prolapse (e.g., prolapse of anterior wall of the vagina, prolapse of vaginal apex, prolapse of posterior wall of vagina, prolapse of uterus etc.), other diseases where organ is prolapsed from the normal position due to weakened pelvic floor muscle (e.g., rectal prolapse etc.) and the like], (d) dermatic diseases [e.g., keloid, Hemangioma, psoriasis, pruritus, etc.], (e) ophthalmic diseases [e.g., glaucoma, ocular hypertension disease etc.], (f) otolaryngological diseases [e.g., Menuel syndrome, tinnitus, gustation disorder, dizziness, disequilibrium, dysphagia etc.], (g) diseases due to environmental and/or occupational factors (e.g., radiation disorder, disorders by ultraviolet ray•infrared ray•laser ray, altitude sickness etc.), (h) ataxia, rigidity, tremor, motion impairment, akinesia, (i) chronic fatigue syndrome, (j) sudden infant death syndrome, (k) hiccup, (l) diseases causing palpitation, vertigo, heartburn and the like.

Among these diseases, the compound of the present invention is particularly useful as a drug for the prophylaxis, treatment or improvement of lower urinary tract diseases such as overactive bladder, stress urinary incontinence, benign prostatic hyperplasia and the like, as well as a drug for the prophylaxis or treatment of these lower urinary tract diseases.

A preparation comprising the compound of the present invention may be any of solid preparations such as powder, granule, tablet, capsule, orally disintegrable films and the like and liquids such as syrup, emulsion, injection and the like.

An agent for the prophylaxis or treatment of the present invention can be produced by any conventional method, for example, blending, kneading, granulation, tabletting, coating, sterilization, emulsification etc., in accordance with the form of the preparation to be produced. For the production of such pharmaceutical preparations, for example, reference can be made to each of the items in general principles for pharmaceutical preparations in the Japanese Pharmacopeia. In addition, the preparation of the present invention may be formulated into a sustained release preparation containing an active ingredient and a biodegradable polymer compound. The sustained release preparation can be produced according to the method described in JP-A-9-263545.

In the preparations of the present invention, the content of the compound of the present invention varies depending on the forms of the preparations, but is generally 0.01 to 100% by weight, preferably 0.1 to 50% by weight, more preferably 0.5 to 20% by weight, relative to the whole preparation.

When the compound of the present invention is used in the above-mentioned pharmaceutical product, it may be used alone, or in admixture with a suitable, pharmaceutically acceptable carrier, for example, excipients (e.g., starch, lactose, sucrose, calcium carbonate, calcium phosphate etc.), binders (e.g., starch, arabic gum, carboxymethyl cellulose, hydroxypropyl cellulose, crystalline cellulose, alginic acid, gelatin, polyvinyl pyrrolidone etc.), lubricants (e.g., stearic acid, magnesium stearate, calcium stearate, talc etc.), disintegrants (e.g., calcium carboxymethylcellulose, talc etc.), diluents (e.g., water for injection, physiological saline etc.) and if desired, with the additives (e.g., a stabilizer, a preservative, a colorant, a fragrance, a solubilizing agent, an emulsifier, a buffer, an isotonic agent etc.) and the like, by ordinary methods. It can be formulated into the solid preparations such as powders, fine granules, granules, tablets, capsules etc., or into the liquid preparations such as injections etc., and can be administered orally or parenterally. In this case, injection is preferably prepared. It can also be administered as a parenteral agent for topical administration (e.g., intramuscular, subcutaneous, organ or joint injection etc., solid preparation such as implant agent, granules, powder and the like, liquid such as suspension and the like, ointment etc.) and the like.

For example, to produce an injection, the compound of the present invention is prepared into an aqueous suspension together with a dispersing agent (e.g., surfactant such as Tween 80, HCO-60 and the like, polysaccharides such as carboxymethylcellulose, sodium alginate, hyaluronic acid and the like, polysorbate etc.), a preservative (e.g., methylparaben, propylparaben etc.), an isotonicity agent (e.g., sodium chloride, mannitol, sorbitol, glucose etc.), a buffering agent (e.g., calcium carbonate etc.), a pH adjuster (e.g., sodium phosphate, potassium phosphate etc.) and the like, whereby a practical preparation for injection is obtained. In addition, compound (I) is dispersed together with a vegetable oil such as sesame oil, corn oil and the like or a mixture thereof with a phospholipid such as lecithin and the like, or medium-chain fatty acid triglyceride (e.g., miglyol 812 etc.) to give an oily suspension for practical injection.

The prophylactic or therapeutic agent of the present invention can also be used together with other pharmaceutical agents.

A drug which is mixed or combined with the compound of the present invention (hereinafter briefly referred to as a combination drug) includes the following:

(1) Agent for the prophylaxis or treatment of other lower urinary tract diseases (including any disease having a symptom represented by lower urinary tract symptoms), adrenaline α1 receptor blocker (e.g., tamsulosin, urapidil, Naftopidil, silodosin, doxazosin, alfuzosin etc.), anti-choline drug (e.g., oxybutynin, propiverine, darifenacin, tolterodine, solifenacin, temiverine, trospium chloride and salts thereof etc.), NK-1 receptor antagonist (e.g., aprepitant, casopitant, LY686017 etc.), adrenaline β3 receptor agonist (e.g., solabegron, YM-178, KRP-204, KUC-7483, MN-246, CL-316243 etc.), TRPV1 receptor agonist (e.g., resiniferatoxin, capsaicin preparation etc.), TRPV1 receptor antagonist (e.g., SB-705498, NGD-8243 etc.), Botulinus toxin preparation (e.g., BTX-A etc.), adrenaline al receptor agonist (e.g., ephedrine hydrochloride, midodrine hydrochloride etc.), adrenaline β2 receptor agonist (e.g., clenbuterol etc.), noradrenaline uptake inhibitory substance, noradrenaline and serotonin uptake inhibitory substance (e.g., duloxetine etc.), tricyclic antidepressant (e.g., imipramine hydrochloride etc.), smooth muscle stimulant (e.g., celimeverine hydrochloride etc.), female sex hormone drug (e.g., binding type estrogen (premarin), estriol etc.) and the like.

(2) Agent for Treating Diabetes

Insulin preparations (e.g., animal insulin preparations extracted from the bovine or swine pancreas; human insulin preparations synthesized by a genetic engineering technique using *Escherichia coli* or a yeast; insulin zinc; protamine zinc insulin; a fragment or a derivative of insulin (e.g., INS-1 etc.), and the like), agents for potentiating insulin sensitivity (e.g., pioglitazone hydrochloride, troglitazone, rosiglitazone or its maleate, JTT-501, MCC-555, YM-440, GI-262570, KRP-297, FK-614, CS-011 etc.), α-glucosidase inhibitors (e.g., voglibose, acarbose, miglitol, emiglitate etc.), biguanides (e.g., phenformin, metformin, buformin etc.), sulfonylureas (e.g., tolbutamide, glibenclamide, gliclazide, chlorpropamide, tolazamide, acetohexamide, glyclopyramide, glimepiride etc.) and other insulin secretagogues (e.g., repaglinide, senaglinide, mitiglinide or its calcium salt hydrate, GLP-1, nateglinide etc.), dipeptidyl peptidase IV inhibitor (e.g., NVP-DPP-278, PT-100, P32/98 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (sodium-glucose cotransporter) inhibitors (e.g., T-1095 etc.) and the like.

(3) Agent for Treating Diabetic Complications

Aldose reductase inhibitors (e.g., tolrestat, epalrestat, zenarestat, zopolrestat, fidarestat (SNK-860), minalrestat (ARI-509), CT-112 etc.), neurotrophic factors (e.g., NGF, NT-3 etc.), AGE inhibitors (e.g., ALT-945, pimagedine, pyratoxathine, N-phenacylthiazolium bromide (ALT-766), EXO-226 etc.), active oxygen scavengers (e.g., thioctic acid etc.), cerebral vasodilators (e.g., tiapuride etc.) and the like.

(4) Antihyperlipidemic Agent

Statin compounds inhibiting cholesterol synthesis (e.g., pravastatin, simvastatin, lovastatin, atorvastatin, fluvastatin, cerivastatin or their salt (e.g., sodium salt etc.) and the like), squalene synthase inhibitors or fibrate compounds having triglyceride lowering action (e.g., bezafibrate, clofibrate, simfibrate, clinofibrate etc.) and the like.

(5) Hypotensive Agent

Angiotensin converting enzyme inhibitors (e.g., captopril, enalapril, delapril etc.), angiotensin II antagonists (e.g., losartan, candesartan cilexetil etc.), calcium antagonists (e.g., manidipine, nifedipine, amlodipine, efonidipine, nicardipine etc.), clonidine, and the like.

(6) Antiobesity Agent

Antiobesity drugs acting on the central nervous system (e.g. dexfenfluramine, fenfluramine, phentermine, sibutramine, anfepramone, dexamphetamine, mazindol, phenylpropanolamine, clobenzorex etc.), pancreatic lipase inhibitors (e.g. orlistat etc.), $β_3$ agonists (e.g. CL-316243, SR-58611-A, UL-TG-307, AJ-9677, AZ40140 etc.), anorectic peptides (e.g. leptin, CNTF (Ciliary Neurotrophic Factor) etc.), cholecystokinin agonists (e.g. lintitript, FPL-15849 etc.), serotonin 2C receptor agonist (e.g., APD-356, SCA-136, ATHX-105, WAY-163909, YM-348) and the like.

(7) Diuretic Agent

Xanthine derivatives (e.g., theobromine sodium salicylate, theobromine calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonic anhydrase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide etc.

(8) Chemotherapeutic Agent

Alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agents (e.g., vincristine, vindesine, taxol etc.), cisplatin, carboplatin, etoposide etc. Among these, 5-fluorouracil derivatives such as Furtulon and Neo-Furtulon are preferred.

(9) Immunotherapeutic Agent

Microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating factors (e.g., granulocyte colony stimulating factor, erythropoietin etc.) and the like. Among these, IL-1, IL-2, IL-12 etc. are preferred.

(10) Therapeutic Agent Recognized to Ameliorate Cachexia in Animal Models or Clinical Practice Progesterone derivatives (e.g., megestrol acetate) [Journal of Clinical Oncology, vol. 12, pp. 213-225, 1994], metoclopramide pharmaceuticals, tetrahydrocannabinol pharmaceuticals (the above reference is applied to both), fat metabolism ameliorating agents (e.g., eicosapentanoic acid) [British Journal of Cancer, vol. 68, pp. 314-318, 1993], growth hormones, IGF-1, and antibodies to the cachexia-inducing factors such as TNF-α, LIF, IL-6 and oncostatin M.

(11) Antiinflammatory Agent

Steroids (e.g., dexamethasone etc.), sodium hyaluronate, cyclooxygenase inhibitors (e.g., indomethacin, ketoprofen, loxoprofen, meloxicam, ampiroxicam, celecoxib, rofecoxib etc.) and the like.

(12) Miscellaneous

Glycosylation inhibitors (e.g., ALT-711 etc.), nerve regeneration promoting drugs (e.g., Y-128, VX853, prosaptide etc.), drugs acting on the central nervous system (e.g., antidepressants such as desipramine, amitriptyline, imipramine, fluoxetine, paroxetine, doxepin etc.), anticonvulsants (e.g., lamotrigine, carbamazepine), antiarrhythmic drugs (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), local analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), sleep-inducing drugs (e.g., triazolam, zolpidem), anticholinergic agents, $\alpha_1$ receptor blocking agents (e.g., tamsulosin), muscle relaxants (e.g., baclofen etc.), potassium channel openers (e.g., nicorandil), calcium channel blocking agents (e.g., nifedipine), agents for preventing or treating Alzheimer's disease (e.g., donepezil, rivastigmine, galanthamine), agents for treating Parkinson's disease (e.g., L-dopa), agents for preventing or treating multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonists, agents of treating HIV infection (saquinavir, zidovudine, lamivudine, nevirapine), agents of treating chronic obstructive pulmonary diseases (salmeterol, thiotropium bromide, cilomilast) and the like.

Anticholinergic agents include, for example, atropine, scopolamine, homatropine, tropicamide, cyclopentolate, butyl scopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrobromide, homatropine hydrobromide, cyclopentolate hydrochloride, flavoxate hydrochloride, pirenzepine hydrochloride, trihexyphenidyl hydrochloride, oxybutynin hydrochloride, tolterodine tartrate etc.) and the like, preferably, oxybutynin, propiverine, darifenacin, tolterodine, temiverine, trospium chloride or a salt thereof (e.g., oxybutynin hydrochloride, tolterodine tartrate etc.). In addition, acetylcholine esterase inhibitors (e.g., distigmine etc.) and the like can be used.

NK-2 receptor antagonists include, for example, a piperidine derivative such as GR159897, GR149861, SR48968 (saredutant), SR144190, YM35375, YM38336, ZD7944, L-743986, MDL105212A, ZD6021, MDL105172A, SCH205528, SCH62373, R-113281 etc., a perhydroisoindole derivative such as RPR-106145 etc., a quinoline derivative such as SB-414240 etc., a pyrrolopyrimidine derivative such as ZM-253270 etc., a pseudopeptide derivative such as MEN11420 (nepadutant), SCH217048, L-659877, PD-147714 (CAM-2291), MEN10376, 516474 etc., and others such as GR100679, DNK333, GR94800, UK-224671, MEN10376, MEN10627, or a salt thereof, and the like.

For a combined use, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:

(1) administration of a single preparation obtained by simultaneously processing the compound of the present invention or a pharmaceutical composition thereof and the concomitant drug, (2) simultaneous administration of two kinds of preparations of the compound of the present invention or a pharmaceutical composition thereof and the concomitant drug or a pharmaceutical composition thereof, which have been separately produced, by the same administration route, (3) administration of two kinds of preparations of the compound of the present invention or a pharmaceutical composition thereof and the concomitant drug or a pharmaceutical composition thereof, which have been separately produced, by the same administration route in a staggered manner, (4) simultaneous administration of two kinds of preparations of the compound of the present invention or a pharmaceutical composition thereof and the concomitant drug or a pharmaceutical composition thereof, which have been separately produced, by different administration routes, (5) administration of two kinds of preparations of the compound of the present invention or a pharmaceutical composition thereof and the concomitant drug or a pharmaceutical composition thereof, which have been separately produced, by different administration routes in a staggered manner (e.g., administration in the order of the compound of the present invention or a pharmaceutical composition thereof and the concomitant drug or a pharmaceutical composition thereof, or in the reverse order) and the like.

The compounding ratio of the compound of the present invention to the concomitant drug in the combination agent of the present invention can be appropriately selected depending on the administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

While the dose varies depending on the kind of the compound of the present invention or a pharmaceutically acceptable salt thereof, administration route, symptom, age of patient and the like, it is, for example, about 0.005-50 mg/kg body weight/day, preferably about 0.05-10 mg/kg body weight/day, more preferably about 0.2-4 mg/kg body weight/day, as the compound of the present invention for oral administration to an adult patient with stress urinary incontinence, which can be administered in about 1 to 3 portions.

When the pharmaceutical composition of the present invention is a sustained-release preparation, the dose varies depending on the kind and content of the compound of the present invention, dosage form, duration of drug release, subject animal of administration (e.g., mammal such as human, rat, mouse, cat, dog, rabbit, cow, pig and the like), and administration object. For parenteral administration, for example, about 0.1 to about 100 mg of the compound of the present invention is designed to be released from the administered preparation in one week.

The dose of the combination drug may be set such that it causes no problems of side effects. The daily dose as the combination drug varies depending on severity of symptoms, age, sex, weight and sensitivity of the subject to be administered, time and interval of administration, property, formulation and kinds of pharmaceutical preparation, kinds of active ingredients, etc., and is not particularly limited. In the case of oral administration, a daily dosage in terms of the concomitant drug is generally in the order of about 0.001 to 2000 mg, preferably about 0.01 to 500 mg, and more preferably about 0.1 to 100 mg, per 1 kg body weight of mammals, which may be administered once a day or in two to four divided portions a day.

In administering the combination drug of the present invention, it may be administered at the same time or, the combination drugs may be administered before administering the compound of the present invention, and vice versa. In case of staggered administration, the time interval varies depending on the active ingredients to be administered, a formulation and an administration route. For example, if the combination drugs are administered first, the compound of the present invention may be administered 1 minute to 3 days, preferably 10 min to 1 day, more preferably 15 min to 1 hr. after administering the combination drugs. If the compound of the present invention is administered first, the combination drugs may be administered 1 minute to 1 day, preferably 10 min to 6 hr, more preferably 15 min to 1 hr. after administering the compound of the present invention.

The pharmaceutical composition of the present invention has low toxicity and can be used safely. Particularly, since the Example compounds shown below are superior in the absorbability by oral administration, they can be advantageously used for oral preparation.

EXAMPLES

The present invention is explained in detail in the following by referring to Reference Examples, Examples, Formulation Examples and Experimental Examples. However, the present invention is not limited to the Examples, and may be modified without departing from the scope of the invention.

$^1$H-NMR spectrum was measured using AV-400M (400 MHz), AVANCE 300 (300 MHz) and AVANCE II 300 (300 MHz) manufactured by Bruker and using tetramethylsilane as the internal standard, and all δ values were shown by ppm. Unless otherwise specified, the numerical values shown for mixed solvents are volume mixing ratios of respective solvents. Unless otherwise specified, % means weight %. The room temperature (ambient temperature) in the present specification is a temperature of about 10° C. to about 35° C.

Unless otherwise specified, elution by column chromatography in Reference Examples and Examples was performed under observation by TLC (thin layer chromatography). For TLC observation, 60F254 manufactured by Merck or TLC (NH) manufactured by FUJI SILYSIA was used as a TLC plate, and the solvent used as an elution solvent for column chromatography was used as an eluent. For detection, a UV detector was employed. Silica gel 60 (70-230 mesh) manufactured by Merck was used as silica gel for column chromatography, and silica gel (CHROMATOREX NH) manufactured by FUJI SILYSIA was used as a basic silica gel.

Other abbreviations used in the description mean the following.
s: singlet
d: doublet
t: triplet
q: quartet
dd: double doublet
br: broad
J: coupling constant
Hz: Hertz
CDCl$_3$: deuterated chloroform
$^1$H NMR: proton nuclear magnetic resonance

Reference Example 1

2-cyano-2-(3,4-dichloro-5-oxo-2,5-dihydrofuran-2-yl)acetamide

Mucochloric acid (15.1 g) and 2-cyanoacetamide (7.53 g) were dissolved in methanol (53.6 ml), and 2.5N aqueous sodium hydroxide solution (53.6 ml) was added dropwise with stirring under ice-cooling. The mixture was allowed to warm to room temperature, and further stirred at room temperature for 3 hr. The reaction mixture was poured into 1N hydrochloric acid containing ice water, methanol was evaporated under reduced pressure, and the mixture was extracted with ethyl acetate. The extract was washed with saturated brine, and dried over anhydrous magnesium sulfate. The solvent was evaporated under reduced pressure. The residue was crystallized from ethanol-diisopropyl ether to give the title compound (3.74 g) as pale-brown crystals.

$^1$H NMR (300 MHz, DMSO-$d_6$) δ ppm 4.84 (1H, d, J=3.2 Hz), 5.91 (1H, d, J=4.0 Hz), 7.85 (1H, br. s.), 8.03 (1H, br. s.).

Example 1

5-chloro-1-[5-chloro-2-(methylsulfonyl)benzyl]-2-imino-1,2-dihydropyridine-3-carboxamide hydrochloride (Step 1) To a solution of methyl 5-chloro-2-(methylsulfanyl)benzoate (3.0 g) in ethyl acetate (200 ml) was added m-chloroperbenzoic acid (8.53 g, containing water: Wako Pure Chemical Industries, Ltd.) at 0° C. The mixture was stirred at room temperature for 5 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:3) to give methyl 5-chloro-2-(methylsulfonyl)benzoate (2.67 g).

$^1$H NMR (300 MHz, CDCl$_3$) δ ppm 3.35 (3H, s), 3.99 (3H, s), 7.55-7.77 (2H, m), 8.07 (1H, d, J=8.48 Hz).

(Step 2) To a solution of methyl 5-chloro-2-(methylsulfonyl)benzoate obtained in Step 1 (2.65 g) in tetrahydrofuran-ethanol (50 ml+5 ml) was added lithium borohydride (348 mg) at 0° C. The mixture was stirred at 60° C. for 2 hr, treated with ice, and extracted with ethyl acetate. The extract was washed successively with 1N hydrochloric acid and saturated brine, and dried over magnesium sulfate. The solvent was evaporated under reduced pressure. The residue was purified by silica gel column chromatography (ethyl acetate:hexane=2:1) to give [5-chloro-2-(methylsulfonyl)phenyl]methanol (2.1 g).

$^1$H NMR (300 MHz, CDCl$_3$) δ ppm 2.93 (1H, t, J=6.69 Hz), 3.16 (3H, s), 4.94 (2H, d, J=6.78 Hz), 7.49 (1H, dd, J=8.38, 2.17 Hz), 7.61 (1H, d, J=1.88 Hz), 7.98 (1H, d, J=8.29 Hz).

(Step 3) Triphenylphosphine (1.19 g) was suspended in acetonitrile (50 ml), bromine (0.24 ml) was added, and the mixture was stirred at room temperature for 30 min. A solution of [5-chloro-2-(methylsulfonyl)phenyl]methanol obtained in Step 2 (1 g) in acetonitrile (10 ml) was added to the reaction mixture. The mixture was stirred at 70° C. for 3 hr, treated with water, and extracted with ethyl acetate. The extract was washed successively with aqueous sodium hydrogen carbonate solution and saturated brine, and dried over anhydrous magnesium sulfate. The solvent was evaporated under reduced pressure. The obtained residue was purified by basic silica gel chromatography (ethyl acetate:hexane=1:3) to give 2-(bromomethyl)-4-chloro-1-(methylsulfonyl)benzene (0.46 g).

$^1$H NMR (300 MHz, CDCl$_3$) δ ppm 3.25 (3H, s), 5.02 (2H, s), 7.49 (1H, dd, J=8.52, 2.08 Hz), 7.58 (1H, d, J=2.27 Hz), 8.01 (1H, d, J=8.33 Hz).

(Step 4) A solution of 2-amino-5-chloronicotinamide (210 mg) and 2-(bromomethyl)-4-chloro-1-(methylsulfonyl)benzene obtained in Step 3 (450 mg) in DMF (5 ml) was stirred at 100° C. for 3 hr. The mixture was allowed to cool to room temperature, ethyl acetate was added, and the precipitated crystals were collected by filtration. The obtained crystals were dissolved in aqueous sodium hydrogen carbonate solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=1:1→3:1). The obtained yellow solid was dissolved in methanol, and 2N hydrogen chloride-ethyl acetate solution was added. The solvent was evaporated under reduced pressure, and the residue was crystallized from methanol-ethyl acetate to give the title compound (30 mg).

$^1$H NMR (300 MHz, DMSO-$d_6$) δ ppm 3.42 (3H, s), 5.84 (2H, s), 7.15 (1H, d, J=1.88 Hz), 7.78 (1H, dd, J=8.48, 1.88 Hz), 8.07 (1H, d, J=8.48 Hz), 8.24 (1H, s), 8.63-8.75 (3H, m), 9.67 (2H, s).

Example 1 A 5-chloro-1-[5-chloro-2-(methylsulfonyl)benzyl]-2-imino-1,2-dihydropyridine-3-carboxamide hydrochloride (Step 1) A 3 M aqueous solution of methyl mercaptan sodium salt (15 ml) was added to a solution of 5-chloro-2-fluorobenzonitrile (5.0 g) in DMSO (100 ml). The resulting mixture was stirred at room temperature for 2 hr. To the reaction mixture was added water (200 ml) and the resulting mixture was stirred at room temperature for 30 min. The precipitate was collected by filtration, washed with water, and dried to give 5-chloro-2-(methylsulfanyl)benzonitrile (4.6 g) as a white solid.

$^1$H NMR (300 MHz, DMSO-$d_6$) δ ppm 2.60 (3H, s), 7.43-7.52 (1H, m), 7.75 (1H, dd, J=8.7, 2.4 Hz), 7.99 (1H, d, J=2.4 Hz).

(Step 2) To a solution of 5-chloro-2-(methylsulfanyl)benzonitrile obtained in Step 1 (1.0 g) in acetonitrile (15 ml) was added dropwise a solution of Oxone® (6.98 g) in water (20 ml). The resulting mixture was stirred at room temperature for 5 hr. Oxone® (1.2 g) was added, and the mixture was stirred overnight at room temperature. To the reaction mixture was added water (25 ml), and the resulting mixture was stirred at 0° C. for 3 hr. The precipitate was collected by filtration, washed with water, and dried to give 5-chloro-2-(methylsulfonyl)benzonitrile (0.92 g) as a white solid.

$^1$H NMR (300 MHz, DMSO-$d_6$) δ ppm 3.41 (3H, s), 8.08-8.13 (2H, m), 8.44 (1H, d, J=1.3 Hz).

(Step 3) To a solution of 5-chloro-2-(methylsulfonyl)benzonitrile obtained in Step 2 (3.8 g) in ethanol (25 ml) was added an 8N solution of ammonia in methanol (5 ml) and Raney cobalt (19 g, wet). The resulting mixture was stirred overnight at room temperature under a hydrogen atmosphere. The reaction mixture was filtered through celite, and the filtrate was concentrated under reduced pressure. To the residue were added ethanol (10 ml) and a 2 M hydrogen chloride-methanol solution (10 ml). The resulting mixture was concentrated under reduced pressure, and the residual solid was collected by filtration and washed with ethyl acetate to give 1-[5-chloro-2-(methylsulfonyl)phenyl]methanamine hydrochloride (3.6 g) as a white solid.

$^1$H NMR (300 MHz, DMSO-$d_6$) δ ppm 3.37 (3H, s), 4.44 (2H, S), 7.65-7.89 (1H, m), 7.89-8.27 (2H, m), 8.61 (3H, br. s.).

(Step 4) To a suspension of 2-cyano-2-(3,4-dichloro-5-oxo-2,5-dihydrofuran-2-yl)acetamide (0.28 g) and 1-[5-chloro-2-(methylsulfonyl)phenyl]methanamine hydrochloride obtained in Step 3 (0.26 g) in ethanol (3 ml) was added N,N-diisopropylethylamine (0.44 ml) at room temperature, and the resulting mixture was heated under reflux for 4 hr. The reaction mixture was treated with water and stirred at 70° C. for 1 hr. After cooling to room temperature, the precipitate was collected by filtration and dried. The precipitate was suspended in methanol, and treated with a 2 M hydrogen chloride-methanol solution (0.3 ml). The resulting mixture was stirred at room temperature overnight. The precipitate was collected by filtration and dried to give the title compound (0.22 g) as white crystals.

$^1$H NMR (300 MHz, DMSO-$d_6$) δ ppm 3.43 (3H, s), 5.82 (2H, br. s.), 7.14 (1H, d, J=1.9 Hz), 7.78 (1H, dd, J=8.5, 2.1 Hz), 8.07 (1H, d, J=8.5 Hz), 8.22 (1H, br. s.), 8.66 (3H, br. s.), 9.65 (2H, br. s.).

Example 2

5-chloro-2-imino-1-[3-(methylsulfinyl)benzyl]-1,2-dihydropyridine-3-carboxamide hydrochloride To a suspension of 2-cyano-2-(3,4-dichloro-5-oxo-2,5-dihydrofuran-2-yl)acetamide (1.0 g) in methanol (10 ml) was added a solution of 1-[3-(methylsulfinyl)phenyl]methanamine hydrochloride (1.8 g) and triethylamine (2.4 ml) in methanol (5 ml) at room temperature, and the mixture was stirred overnight at 50° C. The reaction solvent was evaporated under reduced pressure, acetic acid (5 ml) was added, and the mixture was stirred at 50° C. for 2 hr. The solvent was evaporated under reduced pressure, the residue was partitioned with ethyl acetate, 1N aqueous sodium hydroxide solution and aqueous sodium bicarbonate, and the organic layer was dried over sodium sulfate. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (270 mg).

$^1$H NMR (300 MHz, DMSO-$d_6$) δ ppm 2.76 (3H, s), 5.66 (2H, s), 7.40 (1H, d, J=7.7 Hz), 7.52-7.79 (3H, m), 8.21 (1H, br. s.), 8.68 (2H, br. s.), 8.84 (1H, br. s.), 9.52 (2H, br. s.).

Example 3

5-chloro-1-[3-chloro-4-(methylsulfonyl)benzyl]-2-imino-1,2-dihydropyridine-3-carboxamide hydrochloride A solution of 2-amino-5-chloronicotinamide (200 mg) and 4-(bromomethyl)-2-chloro-1-(methylsulfonyl)benzene (430 mg) in DMF (3 ml) was stirred at 100° C. for 4 hr. The mixture was allowed to cool to room temperature, ethyl acetate was added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=9:1→1:0). The obtained yellow solid was dissolved in methanol, 4N hydrogen chloride-ethyl acetate solution was added, and the precipitated crystals were collected by filtration, and recrystallized to give the title compound (65 mg).

$^1$H NMR (300 MHz, DMSO-$d_6$) δ ppm 3.38 (3H, s), 5.68 (2H, s), 7.45 (1H, d), 7.78 (1H, d, J=1.13 Hz), 8.04 (1H, d, J=8.29 Hz), 8.22 (1H, s), 8.58-8.73 (2H, m), 8.82 (1H, d, J=1.32 Hz), 9.55 (2H, s).

Example 4

5-chloro-2-imino-1-[3-(methylsulfamoyl)benzyl]-1,2-dihydropyridine-3-carboxamide hydrochloride (Step 1) To a 40% methylamine methanol solution (5 ml) was added 3-cyanobenzenesulfonyl chloride (0.88 g) at 0° C., and the mixture was stirred at room temperature for 2 hr. The solvent was evaporated under reduced pressure, saturated brine was added, and the mixture was extracted with ethyl acetate. The solvent was evaporated under reduced pressure. 10% Palladium carbon powder (0.46 g) was added to a solution (10 ml) of the residue in ethanol, and the mixture was stirred overnight under a hydrogen atmosphere (1 atm). The solution was filtered through celite. The solvent was evaporated under reduced pressure. The residue was purified by basic silica gel column chromatography (ethyl acetate) to give 3-(aminomethyl)-N-methylbenzenesulfonamide (0.38 g) as a colorless oil.

$^1$H NMR (300 MHz, CDCl$_3$) δ ppm 1.70 (2H, br. s.), 2.68 (3H, d, J=4.9 Hz), 3.86 (2H, s), 4.88 (1H, br. s.), 7.39-7.62 (2H, m), 7.76 (1H, dt, J=7.5, 1.6 Hz), 7.89 (1H, s).

(Step 2) To a suspension of 2-cyano-2-(3,4-dichloro-5-oxo-2,5-dihydrofuran-2-yl)acetamide (0.28 g) and 3-(aminomethyl)-N-methylbenzenesulfonamide obtained in Step 1 (0.36 g) in ethanol (10 ml) was added potassium carbonate (0.25 g) at room temperature, and the mixture was stirred overnight at 70° C. The reaction solution was filtered through celite. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (76 mg).

$^1$H NMR (300 MHz, DMSO-$d_6$) δ ppm 2.42 (3H, d, J=5.3 Hz), 5.68 (2H, br. s.), 7.50 (1H, d, J=7.2 Hz), 7.54-7.71 (2H, m), 7.71-7.85 (2H, m), 8.21 (1H, br. s.), 8.70 (2H, br. s.), 8.86 (1H, br. s.), 9.53 (2H, br. s.).

Example 5

5-chloro-2-imino-1-[3-(dimethylsulfamoyl)benzyl]-1,2-dihydropyridine-3-carboxamide hydrochloride (Step 1) To a 2M dimethylamine methanol solution (3.7 ml) was added 3-cyanobenzenesulfonyl chloride (1.5 g) at 0° C., and the mixture was stirred at room temperature for 2 hr. The solvent was evaporated under reduced pressure, saturated brine was added, and the mixture was extracted with ethyl acetate. The solvent was evaporated under reduced pressure. 10% Palladium carbon powder (0.79 g) was added to a solution (10 ml) of the residue in ethanol, and the mixture was stirred overnight under a hydrogen atmosphere (1 atm). The solution was filtered through celite. The solvent was evaporated under reduced pressure. The residue was purified by basic silica gel column chromatography (ethyl acetate) to give 3-(aminomethyl)-N,N-dimethylbenzenesulfonamide (1.0 g) as a colorless oil.

¹H NMR (300 MHz, CDCl₃) δ ppm 2.32-2.61 (2H, m), 2.73 (6H, s), 4.02 (2H, s), 7.45-7.56 (1H, m), 7.66 (2H, dd, J=9.1, 7.8 Hz), 7.79 (1H, br. s.).

(Step 2) To a suspension of 2-cyano-2-(3,4-dichloro-5-oxo-2,5-dihydrofuran-2-yl)acetamide (0.73 g) and 3-(aminomethyl)-N,N-dimethylbenzenesulfonamide obtained in Step 1 (1.0 g) in ethanol (10 ml) was added potassium carbonate (0.65 g) at room temperature, and the mixture was stirred overnight at 70° C. The reaction solution was filtered through celite. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (306 mg).

¹H NMR (300 MHz, DMSO-d₆) δ ppm 2.61 (6H, s), 5.70 (2H, s), 7.56 (1H, d, J=7.7 Hz), 7.63-7.78 (2H, m), 7.83 (1H, br. s.), 8.21 (1H, br. s.), 8.67 (2H, d, J=2.1 Hz), 8.89 (1H, d, J=2.3 Hz), 9.55 (2H, br. s.).

Example 6

1-[3-bromo-4-(methylsulfonyl)benzyl]-5-chloro-2-imino-1,2-dihydropyridine-3-carboxamide hydrochloride A solution of 2-amino-5-chloronicotinamide (300 mg) and 2-bromo-4-(bromomethyl)-1-(methylsulfonyl)benzene (860 mg) in DMF (5 ml) was stirred at 100° C. for 6 hr. The mixture was allowed to cool to room temperature, ethyl acetate was added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=9:1→ethyl acetate:methanol=9:1). The obtained yellow solid was dissolved in methanol, 4N hydrogen chloride-ethyl acetate solution was added, and the precipitated crystals were collected by filtration, and recrystallized to give the title compound (195 mg).

¹H NMR (300 MHz, DMSO-d₆) δ ppm 3.38 (3H, s), 5.66 (2H, s), 7.47 (1H, d, J=8.33 Hz), 7.95 (1H, s), 8.06 (1H, d, J=8.33 Hz), 8.22 (1H, s), 8.67 (2H, s), 8.82 (1H, s), 9.53 (2H, s).

Example 7

1-[5-chloro-2-(methylsulfonyl)benzyl]-2-imino-5-methyl-1,2-dihydropyridine-3-carboxamide hydrochloride To a solution (3 ml) of 2-amino-5-methylnicotinamide (100 mg) in N,N-dimethylformamide was added 2-(bromomethyl)-4-chloro-1-(methylsulfonyl)benzene (220 mg), and the mixture was stirred at 100° C. for 4 hr. The mixture was allowed to cool to room temperature, ethyl acetate was added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=5:1→ethyl acetate:methanol=10:1). The obtained yellow solid was dissolved in methanol, 4N hydrogen chloride-ethyl acetate solution (1 ml) was added, and the mixture was crystallized from methanol-ethyl acetate to give the title compound (45 mg).

¹H NMR (300 MHz, DMSO-d₆) δ ppm 2.21 (3H, s), 3.42 (3H, s), 5.81 (2H, s), 6.98 (1H, d, J=1.88 Hz), 7.80 (1H, dd, J=8.48, 2.07 Hz), 8.05-8.16 (3H, m), 8.51 (1H, d, J=1.70 Hz), 8.60 (1H, s), 9.32 (2H, s).

Example 8

5-chloro-2-imino-1-[5-methyl-2-(methylsulfonyl)benzyl]-1,2-dihydropyridine-3-carboxamide hydrochloride (Step 1) To a solution of 1-[5-methyl-2-(methylsulfanyl)phenyl]methanamine hydrochloride (8.0 g) and triethylamine (7.95 g) in tetrahydrofuran (200 ml) was added di-t-butyl dicarbonate (12.85 g) at room temperature. The mixture was stirred at the same temperature for 6 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (300 ml), and m-chloroperbenzoic acid (24.2 g, containing water: Wako Pure Chemical Industries, Ltd.) was added at room temperature. The mixture was stirred at the same temperature for 14 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (50 ml), 4N hydrogen chloride-ethyl acetate solution (20 ml) was added, and the mixture was stirred at 60° C. for 1 hr, and concentrated under reduced pressure to give crystals. The obtained crystals were washed with diethyl ether to give 1-[5-methyl-2-(methylsulfonyl)phenyl]methanamine hydrochloride (6.50 g) as a solid.

¹H NMR (300 MHz, DMSO-d₆) δ ppm 2.42 (3H, s), 3.30 (3H, s), 4.38 (2H, s), 7.49 (1H, dd, J=8.10, 0.94 Hz), 7.64 (1H, s), 7.88 (1H, d, J=8.10 Hz), 8.52 (3H, s).

(Step 2) 2-Cyano-2-(3,4-dichloro-5-oxo-2,5-dihydrofuran-2-yl)acetamide (2.49 g), 1-[5-methyl-2-(methylsulfonyl)phenyl]methanamine hydrochloride obtained in Step 1 (3.0 g) and potassium carbonate (4.4 g) were stirred in ethanol (30 ml) at 80° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (5 ml) was added, and the mixture was crystallized from methanol-ethyl acetate. The precipitated crystals were collected by filtration, and recrystallized to give the title compound (1.26 g).

¹H NMR (300 MHz, DMSO-d₆) δ ppm 2.35 (3H, s), 3.37 (3H, s), 5.83 (2H, s), 6.80 (1H, s), 7.49 (1H, d, J=8.10 Hz), 7.95 (1H, d, J=8.10 Hz), 8.24 (1H, s), 8.63 (1H, d, J=1.51 Hz), 8.67-8.79 (2H, m), 9.63 (2H, s).

Example 9

5-chloro-2-imino-1-[2-(methylsulfonyl)-5-(trifluoromethyl)benzyl]-1,2-dihydropyridine-3-carboxamide hydrochloride (Step 1) A mixture of 2-fluoro-5-(trifluoromethyl)benzonitrile (10 g) and sodium methanethiolate (4.08 g) was stirred in N,N-dimethylformamide (30 ml) at 80° C. for 14 hr. The reaction solution was treated with 1N hydrochloric acid, and extracted with ethyl acetate. The extract was washed successively with aqueous sodium hydrogen carbonate solution and saturated brine, and dried over magnesium sulfate. The solvent was evaporated under reduced pressure to give 2-(methylsulfanyl)-5-(trifluoromethyl)benzonitrile (7.71 g) as a solid.

$^1$H NMR (300 MHz, CDCl$_3$) δ ppm 2.61 (3H, s), 7.37 (1H, d, J=8.48 Hz), 7.74 (1H, dd, J=8.48, 1.51 Hz), 7.82 (1H, s).

(Step 2) To a suspension of lithium aluminum hydride (1.61 g) in tetrahydrofuran (250 ml) was added 2-(methylsulfanyl)-5-(trifluoromethyl)benzonitrile obtained in Step 1 (7.7 g) at 0° C. The mixture was stirred at room temperature for 2 hr, and treated with sodium sulfate 10 hydrate, and the inorganic substance was filtered off through celite. The filtrate was concentrated under reduced pressure. The residue was dissolved in methanol, 4N hydrogen chloride-ethyl acetate solution (15 ml) was added, and the mixture was crystallized from methanol-ethyl acetate to give 1-[2-(methylsulfanyl)-5-(trifluoromethyl)phenyl]methanamine hydrochloride (4.28 g).

$^1$H NMR (300 MHz, DMSO-d$_6$) δ ppm 2.61 (3H, s), 4.11 (2H, d, J=4.54 Hz), 7.56 (1H, d, J=8.33 Hz), 7.74 (1H, d, J=8.33 Hz), 7.81 (1H, s), 8.48 (3H, s).

(Step 3) To a solution of 1-[2-(methylsulfanyl)-5-(trifluoromethyl)phenyl]methanamine hydrochloride obtained in Step 2 (4.27 g) and triethylamine (3.35 g) in tetrahydrofuran (150 ml) was added di-t-butyl dicarbonate (5.42 g) at room temperature. The mixture was stirred at the same temperature for 12 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (200 ml), and m-chloroperbenzoic acid (10.2 g, containing water: Wako Pure Chemical Industries, Ltd.) was added at room temperature. The mixture was stirred at the same temperature for 3 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (100 ml), 4N hydrogen chloride-ethyl acetate solution (10 ml) was added, and the mixture was stirred at 60° C. for 30 min, and concentrated under reduced pressure to give crystals. The obtained crystals were washed with ethyl acetate to give 1-[2-(methylsulfonyl)-5-(trifluoromethyl)phenyl]methanamine hydrochloride (2.96 g) as a solid.

$^1$H NMR (300 MHz, DMSO-d$_6$) δ ppm 3.42 (3H, s), 4.53 (2H, s), 8.04-8.15 (1H, m), 8.22 (2H, d, J=9.09 Hz), 8.58 (3H, s).

(Step 4) 2-Cyano-2-(3,4-dichloro-5-oxo-2,5-dihydrofuran-2-yl)acetamide (1.69 g), 1-[2-(methylsulfonyl)-5-(trifluoromethyl)phenyl]methanamine hydrochloride obtained in Step 3 (2.5 g) and potassium carbonate (2.98 g) were stirred in ethanol (30 ml) at 80° C. for 16 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (5 ml) was added, and the mixture was crystallized from methanol-ethyl acetate. The precipitated crystals were collected by filtration, and recrystallized to give the title compound (1.0 g).

$^1$H NMR (300 MHz, DMSO-d$_6$) δ ppm 3.48 (3H, s), 5.92 (2H, s), 7.37 (1H, s), 8.12 (1H, dd, J=8.19, 1.04 Hz), 8.25 (1H, s), 8.31 (1H, d, J=8.10 Hz), 8.63 (1H, d, J=2.26 Hz), 8.72 (2H, d, J=2.26 Hz), 9.69 (2H, s).

Example 10

1-[5-bromo-2-(methylsulfonyl)benzyl]-5-chloro-2-imino-1,2-dihydropyridine-3-carboxamide hydrochloride (Step 1) 5-Bromo-2-fluorobenzaldehyde (15.4 g) and sodium methanethiolate (5.85 g) were stirred in N,N-dimethylformamide (30 ml) at 60° C. for 30 min. The reaction solution was treated with 1N hydrochloric acid, and extracted with ethyl acetate. The extract was washed successively with aqueous sodium hydrogen carbonate solution and saturated brine, and dried over magnesium sulfate. The solvent was evaporated under reduced pressure. The residue was crystallized from ethyl acetate-hexane to give 5-bromo-2-(methylsulfanyl)benzaldehyde (11.1 g).

$^1$H NMR (300 MHz, CDCl$_3$) δ ppm 2.50 (3H, s), 7.22 (1H, d, J=8.67 Hz), 7.63 (1H, dd, J=8.48, 2.26 Hz), 7.92 (1H, d, J=2.26 Hz), 10.22 (1H, s).

(Step 2) 5-Bromo-2-(methylsulfanyl)benzaldehyde obtained in Step 1 (11.0 g) and O-methylhydroxylamine hydrochloride (4.37 g) were stirred in pyridine (30 ml) at room temperature for 14 hr. The reaction solution was treated with water, and extracted with ethyl acetate. The extract was washed successively with 1N hydrochloric acid (twice) and saturated brine, and dried over magnesium sulfate. The solvent was evaporated under reduced pressure to give 5-bromo-2-(methylsulfanyl)benzaldehyde O-methyloxime (11.9 g).

$^1$H NMR (300 MHz, CDCl$_3$) δ ppm 2.43 (3H, s), 4.00 (3H, s), 7.18 (1H, d, J=8.71 Hz), 7.43 (1H, dd, J=8.52, 2.46 Hz), 7.90 (1H, d, J=2.27 Hz), 8.46 (1H, s).

(Step 3) To a solution of 5-bromo-2-(methylsulfanyl)benzaldehyde O-methyloxime obtained in Step 2 (11.8 g) in tetrahydrofuran (200 ml) was added tetrahydrofuran-borane (113.4 ml, 1M tetrahydrofuran solution) at 0° C. The mixture was stirred at 80° C. for 3 hr, and treated with ice, and 1N hydrochloric acid (200 ml) was added. The mixture was stirred at 90° C. for 1 hr, and ethyl acetate was added to the mixture. The separated aqueous layer was basified with 8N sodium hydroxide solution, and extracted with ethyl acetate. The extract was washed with saturated brine, and dried over magnesium sulfate. The solvent was evaporated under reduced pressure. The obtained residue was dissolved in methanol, 4N hydrogen chloride-ethyl acetate solution (15 ml) was added, and the obtained precipitate was collected by filtration, and washed with ethyl acetate to give 1-[5-bromo-2-(methylsulfanyl)phenyl]methanamine hydrochloride (7.25 g).

$^1$H NMR (300 MHz, DMSO-d$_6$) δ ppm 2.52 (3H, s), 4.05 (2H, s), 7.35 (1H, d, J=8.48 Hz), 7.59 (1H, dd, J=8.48, 2.26 Hz), 7.66-7.76 (1H, m), 8.47 (3H, s).

(Step 4) To a solution of 1-[5-bromo-2-(methylsulfanyl)phenyl]methanamine hydrochloride obtained in Step 3 (6.25 g) and triethylamine (4.72 g) in tetrahydrofuran (150 ml) was added di-t-butyl dicarbonate (7.62 g) at room temperature. The mixture was stirred at the same temperature for 14 hr, treated with water, and extracted with ethyl acetate. The extract was washed successively with 1N hydrochloric acid and saturated brine, and dried over magnesium sulfate. The solvent was evaporated under reduced pressure. The obtained residue was dissolved in ethyl acetate (200 ml), and m-chloroperbenzoic acid (14.4 g, containing water: Wako Pure Chemical Industries, Ltd.) was added at room temperature. The mixture was stirred at the same temperature for 4 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=2:1). The obtained residue was dissolved in methanol (100 ml), 4N hydrogen chloride-ethyl acetate solution (15 ml) was added, and the mixture was stirred at 60° C. for 1 hr, and concentrated under reduced pressure to give crystals. The obtained crystals were washed with ethyl acetate to give 1-[5-bromo-2-(methylsulfonyl)phenyl]methanamine hydrochloride (5.85 g) as a solid.

$^1$H NMR (300 MHz, DMSO-$d_6$) δ ppm 3.35 (3H, s), 4.43 (2H, s), 7.91 (2H, s), 8.09 (1H, s), 8.60 (3H, s).

(Step 5) 2-Cyano-2-(3,4-dichloro-5-oxo-2,5-dihydrofuran-2-yl)acetamide (1.95 g), 1-[5-bromo-2-(methylsulfonyl)phenyl]methanamine hydrochloride obtained in Step 4 (3.0 g) and potassium carbonate (3.45 g) were stirred in ethanol (30 ml) at 80° C. for 16 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.9 g).

$^1$H NMR (300 MHz, DMSO-$d_6$) δ ppm 3.41 (3H, s), 5.84 (2H, s), 7.26 (1H, d, J=1.51 Hz), 7.86-8.04 (2H, m), 8.24 (1H, s), 8.56-8.76 (3H, m), 9.65 (2H, s).

Example 11

5-chloro-2-imino-1-[5-methoxy-2-(methylsulfonyl)benzyl]-1,2-dihydropyridine-3-carboxamide hydrochloride (Step 1) A mixture of 2-fluoro-5-methoxybenzonitrile (10 g) and sodium methanethiolate (5.1 g) was stirred in N,N-dimethylformamide (20 ml) at 60° C. for 3 hr. The reaction solution was treated with water, and extracted with ethyl acetate. The extract was washed successively with 1N hydrochloric acid, aqueous sodium hydrogen carbonate solution and saturated brine, and dried over magnesium sulfate. The solvent was evaporated under reduced pressure. The obtained residue was crystallized from ethyl acetate-hexane to give 5-methoxy-2-(methylsulfanyl)benzonitrile (8.3 g).

$^1$H NMR (300 MHz, CDCl$_3$) δ ppm 2.52 (3H, s), 3.82 (3H, s), 7.02-7.11 (1H, m), 7.13 (1H, d, J=3.03 Hz), 7.37 (1H, d, J=8.71 Hz).

(Step 2) To a suspension of lithium aluminum hydride (2.1 g) in tetrahydrofuran (200 ml) was added 5-methoxy-2-(methylsulfanyl)benzonitrile obtained in Step 1 (8.27 g) at 0° C. The mixture was stirred at room temperature for 3 hr, and treated with sodium sulfate 10 hydrate. The mixture was further stirred at room temperature for 30 min, and the inorganic substance was filtered off through celite. The filtrate was concentrated under reduced pressure. The residue was dissolved in methanol, and 4N hydrogen chloride-ethyl acetate solution (15 ml) was added. The mixture was crystallized from methanol-ethyl acetate, and the obtained crystals were washed with ethyl acetate to give 1-[5-methoxy-2-(methylsulfanyl)phenyl]methanamine hydrochloride (8.45 g).

$^1$H NMR (300 MHz, DMSO-$d_6$) δ ppm 2.40 (3H, s), 3.77 (3H, s), 4.12 (2H, s), 6.86-7.03 (1H, m), 7.13-7.27 (1H, m), 7.43 (1 H, d, J=8.67 Hz), 8.51 (3H, s).

(Step 3) To a solution of 1-[5-methoxy-2-(methylsulfanyl)phenyl]methanamine hydrochloride obtained in Step 2 (6.0 g) and triethylamine (5.53 g) in tetrahydrofuran (150 ml) was added di-t-butyl dicarbonate (8.94 g) at room temperature. The mixture was stirred at the same temperature for 4 hr, treated with water, and extracted with ethyl acetate. The extract was washed successively with 1N hydrochloric acid and saturated brine, and dried over magnesium sulfate. The solvent was evaporated under reduced pressure. The obtained residue was dissolved in ethyl acetate (200 ml), and m-chloroperbenzoic acid (16.83 g, containing water: Wako Pure Chemical Industries, Ltd.) was added at room temperature. The mixture was stirred at the same temperature for 20 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (100 ml), and 4N hydrogen chloride-ethyl acetate solution (15 ml) was added. The mixture was stirred at 60° C. for 1 hr, and concentrated under reduced pressure to give crystals. The obtained crystals were washed with ethyl acetate to give 1-[5-methoxy-2-(methylsulfonyl)phenyl]methanamine hydrochloride (5.5 g) as a solid.

$^1$H NMR (300 MHz, DMSO-$d_6$) δ ppm 3.27 (3H, s), 3.90 (3H, s), 4.40 (2H, s), 7.19 (1H, dd, J=8.90, 2.46 Hz), 7.41 (1H, s), 7.92 (1H, d, J=8.71 Hz), 8.56 (3H, s).

(Step 4) 2-Cyano-2-(3,4-dichloro-5-oxo-2,5-dihydrofuran-2-yl)acetamide (2.33 g), 1-[5-methoxy-2-(methylsulfonyl)phenyl]methanamine hydrochloride obtained in Step 3 (3.0 g) and potassium carbonate (4.12 g) were stirred in ethanol (30 ml) at 85° C. for 16 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (4 ml) was added. The mixture was crystallized from methanol-ethyl acetate, and the precipitated crystals were collected by filtration, and recrystallized to give the title compound (1.7 g).

$^1$H NMR (300 MHz, DMSO-$d_6$) δ ppm 3.35 (3H, s), 3.82 (3H, s), 5.80 (2H, s), 6.42 (1H, d, J=2.26 Hz), 7.24 (1H, dd, J=8.85, 2.45 Hz), 8.03 (1H, d, J=8.85 Hz), 8.23 (1H, s), 8.59 (1H, s), 8.69 (2H, s), 9.63 (2H, s).

Example 12

5-chloro-1-[3-chloro-5-(methylsulfonyl)benzyl]-2-imino-1,2-dihydropyridine-3-carboxamide hydrochloride (Step 1) A mixture of 3-bromo-5-chlorobenzonitrile (4.0 g), sodium methanethiolate (1.42 g), Pd$_2$(dba)$_3$ (84 mg), Xantphos (106 mg) and N,N-diisopropylethylamine (4.78 g) was stirred in toluene (100 ml) at 90° C. for 9 hr. The reaction mixture was treated with 1N hydrochloric acid, and extracted with ethyl acetate. The organic layer was washed with saturated brine, and dried over magnesium sulfate. The solvent was evaporated under reduced pressure. The residue was purified by silica gel column chromatography (ethyl acetate:hexane=1:20) to give 3-chloro-5-(methylsulfanyl)benzonitrile (2.6 g) as a solid.

$^1$H NMR (300 MHz, CDCl$_3$) δ ppm 2.51 (3H, s), 7.33-7.35 (1H, m), 7.36 (1H, t, J=1.60 Hz), 7.39 (1H, t, J=1.79 Hz).

(Step 2) To a suspension of lithium aluminum hydride (0.79 g) in tetrahydrofuran (200 ml) was added 3-chloro-5-(methylsulfanyl)benzonitrile obtained in Step 1 (3.2 g) at 0° C. The mixture was stirred at room temperature for 3 hr, and treated with sodium sulfate 10 hydrate. The mixture was stirred at room temperature for 30 min, and the inorganic substance was filtered off through celite. The filtrate was concentrated under reduced pressure. The residue was dissolved in methanol, and 4N hydrogen chloride-ethyl acetate solution (5 ml) was added. The mixture was crystallized from methanol-ethyl acetate, and the obtained crystals were washed with ethyl acetate to give 1-[3-chloro-5-(methylsulfanyl)phenyl]methanamine hydrochloride (2.8 g).

$^1$H NMR (300 MHz, DMSO-d$_6$) δ ppm 2.52 (3H, s), 4.00 (2H, s), 7.31 (1H, t, J=1.79 Hz), 7.36 (1H, s), 7.41 (1H, s), 8.51 (3H, s).

(Step 3) To a solution of 1-[3-chloro-5-(methylsulfanyl)phenyl]methanamine hydrochloride obtained in Step 2 (2.6 g) and triethylamine (2.35 g) in tetrahydrofuran (100 ml) was added di-t-butyl dicarbonate (3.8 g) at room temperature. The mixture was stirred at the same temperature for 4 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (100 ml), and m-chloroperbenzoic acid (7.15 g, containing water: Wako Pure Chemical Industries, Ltd.) was added at room temperature. The mixture was stirred at the same temperature for 2 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (70 ml), and 4N hydrogen chloride-ethyl acetate solution (10 ml) was added. The mixture was stirred at 60° C. for 30 min, and concentrated under reduced pressure to give crystals. The obtained crystals were washed with ethyl acetate to give 1-[3-chloro-5-(methylsulfonyl)phenyl]methanamine hydrochloride (2.41 g) as a solid.

$^1$H NMR (300 MHz, DMSO-d$_6$) δ ppm 3.30 (3H, s), 4.17 (2H, s), 8.01 (2H, d, J=1.51 Hz), 8.09 (1H, d, J=1.32 Hz), 8.55 (3H, s).

(Step 4) 2-Cyano-2-(3,4-dichloro-5-oxo-2,5-dihydrofuran-2-yl)acetamide (1.68 g), 1-[3-chloro-5-(methylsulfonyl)phenyl]methanamine hydrochloride obtained in Step 3 (2.2 g) and potassium carbonate (2.97 g) were stirred in ethanol (30 ml) at 85° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (3 ml) was added. The mixture was crystallized from methanol-ethyl acetate, and the precipitated crystals were collected by filtration, and recrystallized to give the title compound (0.63 g).

$^1$H NMR (300 MHz, DMSO-d$_6$) δ ppm 3.31 (3H, s), 5.65 (2H, s), 7.78 (1H, t, J=1.70 Hz), 7.92 (1H, t, J=1.51 Hz), 8.03 (1H, t, J=1.70 Hz), 8.21 (1H, s), 8.65 (1H, s), 8.67 (1H, d, J=2.07 Hz), 8.83 (1H, d, J=2.07 Hz), 9.56 (2H, s).

Example 13

5-chloro-1-[3-fluoro-5-(methylsulfonyl)benzyl]-2-imino-1,2-dihydropyridine-3-carboxamide hydrochloride (Step 1) A mixture of 3-bromo-5-fluorobenzonitrile (10.0 g), sodium methanethiolate (3.85 g), Pd$_2$(dba)$_3$ (229 mg), Xantphos (289 mg) and N,N-diisopropylethylamine (12.9 g) was stirred in toluene (100 ml) at 90° C. for 9 hr. The reaction mixture was treated with 1N hydrochloric acid, and extracted with ethyl acetate. The organic layer was washed with saturated brine, and dried over magnesium sulfate. The solvent was evaporated under reduced pressure. The residue was purified by silica gel column chromatography (ethyl acetate:hexane=1:19) to give 3-fluoro-5-(methylsulfanyl)benzonitrile (6.2 g) as a solid.

$^1$H NMR (300 MHz, CDCl$_3$) δ ppm 2.51 (3H, s), 7.04-7.19 (2H, m), 7.23-7.28 (1H, m).

(Step 2) To a suspension of lithium aluminum hydride (1.41 g) in tetrahydrofuran (300 ml) was added 3-fluoro-5-(methylsulfanyl)benzonitrile obtained in Step 1 (6.2 g) at 0° C. The mixture was stirred at room temperature for 3 hr, and treated with sodium sulfate 10 hydrate. The mixture was stirred at room temperature for 30 min, and the inorganic substance was filtered off through celite. The filtrate was concentrated under reduced pressure. The residue was dissolved in methanol, and 4N hydrogen chloride-ethyl acetate solution (15 ml) was added. The mixture was crystallized from methanol-ethyl acetate to give 1-[3-fluoro-5-(methylsulfanyl)phenyl]methanamine hydrochloride (4.96 g).

$^1$H NMR (300 MHz, DMSO-d$_6$) δ ppm 2.52 (3H, s), 4.01 (2H, 5), 7.12 (1H, s), 7.15 (1H, s), 7.28 (1H, s), 8.51 (3H, s).

(Step 3) To a solution of 1-[3-fluoro-5-(methylsulfanyl)phenyl]methanamine hydrochloride obtained in Step 2 (4.58 g) and triethylamine (4.46 g) in tetrahydrofuran (150 ml) was added di-t-butyl dicarbonate (7.22 g) at room temperature. The mixture was stirred at the same temperature for 4 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (200 ml), and m-chloroperbenzoic acid (13.6 g, containing water: Wako Pure Chemical Industries, Ltd.) was added at room temperature. The mixture was stirred at the same temperature for 2 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (70 ml), and 4N hydrogen chloride-ethyl acetate solution (15 ml) was added. The mixture was stirred at 60° C. for 1 hr, and concentrated under reduced pressure to give 1-[3-fluoro-5-(methylsulfonyl)phenyl]methanamine hydrochloride (3.76 g) as a solid.

$^1$H NMR (300 MHz, DMSO-d$_6$) δ ppm 3.29 (3H, s), 4.18 (2H, s), 7.80 (1H, d, J=1.32 Hz), 7.83 (1H, d, J=1.51 Hz), 8.00 (1H, s), 8.62 (3H, s).

(Step 4) A mixture of 2-cyano-2-(3,4-dichloro-5-oxo-2,5-dihydrofuran-2-yl)acetamide (2.04 g), 1-[3-fluoro-5-(methylsulfonyl)phenyl]methanamine hydrochloride obtained in Step 3 (2.5 g) and potassium carbonate (3.6 g) was stirred in ethanol (50 ml) at 85° C. for 20 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (3 ml) was added. The mixture was crystallized from methanol-ethyl acetate, and the precipitated crystals were collected by filtration, and recrystallized to give the title compound (0.7 g).

$^1$H NMR (300 MHz, DMSO-$d_6$) δ ppm 3.30 (3H, s), 5.68 (2H, s), 7.58 (1H, d, J=9.80 Hz), 7.79-7.89 (2H, m), 8.21 (1H, s), 8.66 (1H, s), 8.68 (1H, s), 8.82 (1H, s), 9.57 (2H, s).

Example 14

5-chloro-1-[5-chloro-2-(methylsulfinyl)benzyl]-2-imino-1,2-dihydropyridine-3-carboxamide hydrochloride (Step 1) A mixture of 5-chloro-2-fluorobenzonitrile (5.0 g) and sodium methanethiolate (2.48 g) was stirred in N,N-dimethylformamide (20 ml) at 60° C. for 1 hr. The reaction solution was treated with 1N hydrochloric acid, and extracted with ethyl acetate. The extract was washed with saturated brine, and dried over magnesium sulfate. The solvent was evaporated under reduced pressure to give 5-chloro-2-(methylsulfanyl)benzonitrile (5.7 g).

$^1$H NMR (300 MHz, CDCl$_3$) δ ppm 1.55 (3H, s), 7.20-7.28 (1H, m), 7.49 (1H, dd, J=8.33, 2.27 Hz), 7.57 (1H, d, J=2.27 Hz).

(Step 2) To a suspension of lithium aluminum hydride (1.41 g) in tetrahydrofuran (300 ml) was added 5-chloro-2-(methylsulfanyl)benzonitrile obtained in Step 1 (5.7 g) at 0° C. The mixture was stirred at room temperature for 3 hr, and treated with sodium sulfate 10 hydrate. The mixture was further stirred at room temperature for 1 hr, and the inorganic substance was filtered off through celite. The filtrate was concentrated under reduced pressure. The residue was dissolved in methanol, and 4N hydrogen chloride-ethyl acetate solution (10 ml) was added. The mixture was crystallized from methanol-ethyl acetate to give 1-[5-chloro-2-(methylsulfanyl)phenyl]methanamine hydrochloride (5.11 g).

$^1$H NMR (300 MHz, DMSO-$d_6$) δ ppm 2.52 (3H, s), 4.06 (2H, s), 7.38-7.50 (2H, m), 7.58 (1H, d, J=2.27 Hz), 8.49 (3H, s).

(Step 3) To a solution of 1-[5-chloro-2-(methylsulfanyl)phenyl]methanamine hydrochloride obtained in Step 2 (5.11 g) and triethylamine (4.61 g) in tetrahydrofuran (150 ml) was added di-t-butyl dicarbonate (6.47 g) at room temperature. The mixture was stirred at the same temperature for 2 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (200 ml), and m-chloroperbenzoic acid (5.62 g, containing water: Wako Pure Chemical Industries, Ltd.) was added at 0° C. The mixture was stirred at the same temperature for 2 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=2:1). The obtained residue was dissolved in methanol (100 ml), and 4N hydrogen chloride-ethyl acetate solution (10 ml) was added. The mixture was stirred at 60° C. for 30 min, and concentrated under reduced pressure to give 1-[5-chloro-2-(methylsulfinyl)phenyl]methanamine hydrochloride (3.81 g) as a solid.

$^1$H NMR (300 MHz, DMSO-$d_6$) δ ppm 2.78 (3H, s), 4.15 (2H, s), 7.74 (1H, dd, J=8.48, 2.07 Hz), 7.83 (1H, s), 7.90 (1H, d, J=8.48 Hz), 8.62 (3H, s).

(Step 4) 2-Cyano-2-(3,4-dichloro-5-oxo-2,5-dihydrofuran-2-yl)acetamide (2.04 g), 1-[5-chloro-2-(methylsulfinyl)phenyl]methanamine hydrochloride obtained in Step 3 (2.5 g) and potassium carbonate (3.59 g) were stirred in ethanol (40 ml) at 85° C. for 14 hr. The reaction mixture was treated with 1N sodium hydroxide solution, and extracted with a mixed solvent of ethyl acetate-tetrahydrofuran. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (3 ml) was added. The mixture was crystallized from methanol-ethyl acetate, and the precipitated crystals were collected by filtration, and recrystallized to give the title compound (0.4 g).

$^1$H NMR (300 MHz, DMSO-$d_6$) δ ppm 2.85 (3H, s), 5.56-5.76 (2H, m), 6.99 (1H, d, J=1.88 Hz), 7.73 (1H, dd, J=8.38, 1.98 Hz), 8.00 (1H, d, J=8.48 Hz), 8.22 (1H, s), 8.64-8.72 (2H, m), 8.74 (1H, s), 9.63 (2H, s).

Example 15

5-chloro-1-[4-chloro-3-(methylsulfonyl)benzyl]-2-imino-1,2-dihydropyridine-3-carboxamide hydrochloride (Step 1) Triphenylphosphine (2.38 g) was suspended in acetonitrile (30 ml), bromine (0.47 ml) was added, and the mixture was stirred for 30 min. [4-Chloro-3-(methylsulfonyl)phenyl]methanol (2.0 g) was added to the reaction mixture, and the mixture was stirred at 85° C. for 8 hr, treated with aqueous sodium hydrogen carbonate solution, and extracted with ethyl acetate. The extract was washed with saturated brine, and dried over anhydrous magnesium sulfate. The solvent was evaporated under reduced pressure. The obtained residue was purified by basic silica gel chromatography (ethyl acetate:hexane=1:1) to give 4-(bromomethyl)-1-chloro-2-(methylsulfonyl)benzene (1.23 g).

$^1$H NMR (300 MHz, CDCl$_3$) δ ppm 3.29 (3H, s), 4.49 (2H, s), 7.43-7.72 (2H, m), 8.17 (1H, d, J=2.07 Hz).

(Step 2) A solution of 2-amino-5-chloronicotinamide (484 mg) and 4-(bromomethyl)-1-chloro-2-(methylsulfonyl)benzene obtained in Step 1 (1.2 g) in DMF (10 ml) was stirred at 90° C. for 20 hr. The mixture was allowed to cool to room temperature, ethyl acetate was added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate). The obtained yellow solid was dissolved in methanol, 4N hydrogen chloride-ethyl acetate solution (2 ml) was added, and the precipitated crystals were collected by filtration, and recrystallized to give the title compound (160 mg).

$^1$H NMR (300 MHz, DMSO-$d_6$) δ ppm 3.39 (3H, s), 5.63 (2H, s), 7.60 (1H, dd, J=8.29, 2.26 Hz), 7.79 (1H, d, J=8.29 Hz), 8.12 (1H, d, J=2.26 Hz), 8.20 (1H, s), 8.61 (1H, s), 8.63 (1H, d, J=2.26 Hz), 8.83 (1H, d, J=2.26 Hz), 9.49 (2H, s).

Example 16

5-chloro-1-[4-fluoro-2-(methylsulfonyl)benzyl]-2-imino-1,2-dihydropyridine-3-carboxamide hydrochloride A mixture of 2-cyano-2-(3,4-dichloro-5-oxo-2,5-dihydrofuran-2-yl)acetamide (3.0 g), 1-[4-fluoro-2-(methylsulfonyl)phenyl]methanamine hydrochloride (3.67 g) and potassium carbonate (5.29 g) was stirred in ethanol (50 ml) at 85° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained yellow solid was dissolved in methanol, and 4N hydrogen chloride-ethyl acetate solution (4 ml) was added. The mixture was crystallized from methanol-ethyl acetate, and the precipitated crystals were collected by filtration, and recrystallized to give the title compound (1.22 g).

$^1$H NMR (300 MHz, DMSO-$d_6$) δ ppm 3.47 (3H, s), 5.82 (2H, s), 7.10 (1H, dd, J=8.71, 4.92 Hz), 7.51-7.63 (1H, m), 7.91 (1H, dd, J=8.33, 2.65 Hz), 8.24 (1H, s), 8.63 (1H, d, J=1.89 Hz), 8.71 (2H, d, J=1.89 Hz), 9.64 (2H, s).

Example 17

5-chloro-1-[5-chloro-2-(ethylsulfonyl)benzyl]-2-imino-1,2-dihydropyridine-3-carboxamide hydrochloride (Step 1) A mixture of 5-chloro-2-fluorobenzonitrile (5.83 g) and sodium ethanethiolate (3.47 g) was stirred in N,N-dimethylformamide (50 ml) at room temperature for 14 hr. The reaction solution was treated with 1N hydrochloric acid, and extracted with ethyl acetate. The extract was washed with saturated brine, and dried over magnesium sulfate. The solvent was evaporated under reduced pressure to give 5-chloro-2-(ethylsulfanyl)benzonitrile (7.4 g).

$^1$H NMR (300 MHz, CDCl$_3$) δ ppm 1.36 (3H, t, J=7.44 Hz), 3.04 (2H, q, J=7.41 Hz), 7.32-7.38 (1H, m), 7.44-7.50 (1H, m), 7.59 (1H, d, J=2.26 Hz).

(Step 2) To a suspension of lithium aluminum hydride (1.7 g) in tetrahydrofuran (300 ml) was added a solution of 5-chloro-2-(ethylsulfanyl)benzonitrile obtained in Step 1 (7.4 g) in tetrahydrofuran (20 ml) at 0° C. The mixture was stirred at room temperature for 3 hr, and treated with sodium sulfate 10 hydrate. The mixture was further stirred at room temperature for 30 min, and the inorganic substance was filtered off through celite. The filtrate was concentrated under reduced pressure. The residue was dissolved in methanol, and 4N hydrogen chloride-ethyl acetate solution (15 ml) was added. The mixture was crystallized from methanol-ethyl acetate to give 1-[5-chloro-2-(ethylsulfanyl)phenyl]methanamine hydrochloride (5.89 g).

$^1$H NMR (300 MHz, DMSO-$d_6$) δ ppm 1.22 (3H, t, J=7.19 Hz), 3.00 (2H, q, J=7.19 Hz), 4.10 (2H, s), 7.39-7.56 (2H, m), 7.62 (1H, d, J=1.89 Hz), 8.50 (3H, s).

(Step 3) To a solution of 1-[5-chloro-2-(ethylsulfanyl)phenyl]methanamine hydrochloride obtained in Step 2 (5.0 g) and triethylamine (4.25 g) in tetrahydrofuran (150 ml) was added di-t-butyl dicarbonate (5.5 g) at room temperature. The mixture was stirred at the same temperature for 14 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (200 ml), and m-chloroperbenzoic acid (12.9 g, containing water: Wako Pure Chemical Industries, Ltd.) was added at room temperature. The mixture was stirred at the same temperature for 2 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (100 ml), and 4N hydrogen chloride-ethyl acetate solution (15 ml) was added. The mixture was stirred at 60° C. for 1 hr, and concentrated under reduced pressure to give 1-[5-chloro-2-(ethylsulfonyl)phenyl]methanamine hydrochloride (3.81 g) as a solid.

$^1$H NMR (300 MHz, DMSO-$d_6$) δ ppm 1.14 (3H, t, J=7.19 Hz), 3.43 (2H, q, J=7.19 Hz), 4.41 (2H, s), 7.78 (1H, d, J=8.71 Hz), 7.95 (2H, d, J=8.71 Hz), 8.58 (3H, s).

(Step 4) 2-Cyano-2-(3,4-dichloro-5-oxo-2,5-dihydrofuran-2-yl)acetamide (1.81 g), 1-[5-chloro-2-(ethylsulfonyl)phenyl]methanamine hydrochloride obtained in Step 3 (2.5 g) and potassium carbonate (3.19 g) were stirred in ethanol (30 ml) at 85° C. for 24 hr. The reaction mixture was treated with 1N sodium hydroxide solution, and extracted with a mixed solvent of ethyl acetate-tetrahydrofuran. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (4 ml) was added. The mixture was crystallized from methanol-ethyl acetate, and the precipitated crystals were collected by filtration, and recrystallized to give the title compound (1.3 g).

$^1$H NMR (300 MHz, DMSO-$d_6$) δ ppm 1.21 (3H, t, J=7.25 Hz), 3.51 (2H, q, J=7.35 Hz), 5.80 (2H, s), 7.19 (1H, d, J=1.88 Hz), 7.78 (1H, dd, J=8.48, 1.88 Hz), 8.01 (1H, d, J=8.48 Hz), 8.23 (1H, s), 8.64 (1H, d, J=2.07 Hz), 8.65-8.72 (2H, m), 9.64 (2H, s).

Example 18

5-chloro-1-[5-fluoro-2-(methylsulfonyl)benzyl]-2-imino-1,2-dihydropyridine-3-carboxamide hydrochloride 2-Cyano-2-(3,4-dichloro-5-oxo-2,5-dihydrofuran-2-yl)acetamide (3.0 g), 1-[5-fluoro-2-(methylsulfonyl)phenyl]methanamine hydrochloride (3.67 g) and potassium carbonate (5.29 g) were stirred in ethanol (50 ml) at 85° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained yellow solid was dissolved in methanol, and 4N hydrogen chloride-ethyl acetate solution (5 ml) was added. The mixture was crystallized from methanol-ethyl acetate, and the precipitated crystals were collected by filtration, and recrystallized to give the title compound (1.14 g).

$^1$H NMR (300 MHz, DMSO-$d_6$) δ ppm 3.42 (3H, s), 5.86 (2H, s) 6.99 (1H, dd, J=9.98, 2.45 Hz), 7.46-7.62 (1H, m), 8.14 (1H, dd, J=8.85, 5.65 Hz), 8.24 (1H, s), 8.71 (3H, s), 9.68 (2H, s).

Example 19

1-[4-bromo-3-(methylsulfonyl)benzyl]-5-chloro-2-imino-1,2-dihydropyridine-3-carboxamide hydrochloride A solution of 2-amino-5-chloronicotinamide (373 mg) and 1-bromo-4-(bromomethyl)-2-(methylsulfonyl)benzene (1.07 g) in DMF (5 ml) was stirred at 90° C. for 24 hr. The mixture was allowed to cool to room temperature, ethyl acetate was added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained yellow solid was dissolved in methanol, 4N hydrogen chloride-ethyl acetate solution (2 ml) was added, and the precipitated crystals were collected by filtration, and recrystallized to give the title compound (310 mg).

$^1$H NMR (300 MHz, DMSO-$d_6$) δ ppm 3.40 (3H, s), 5.62 (2H, s), 7.49 (1H, dd, J=8.29, 2.26 Hz), 7.95 (1H, d, J=8.10 Hz), 8.14 (1H, d, J=2.26 Hz), 8.21 (1H, s) 8.57-8.71 (2H, m), 8.84 (1H, d, J=2.07 Hz), 9.52 (2H, s).

Example 20

5-chloro-1-[4-fluoro-3-(methylsulfonyl)benzyl]-2-imino-1,2-dihydropyridine-3-carboxamide hydrochloride (Step 1) Triphenylphosphine (3.21 g) was suspended in acetonitrile (50 ml), bromine (0.64 ml) was added, and the mixture was stirred for 30 min. [4-Fluoro-3-(methylsulfonyl)phenyl]methanol (2.5 g) was added to the reaction mixture, and the mixture was stirred at 85° C. for 20 hr, treated with aqueous sodium hydrogen carbonate solution, and extracted with ethyl acetate. The extract was washed with saturated brine, and dried over anhydrous magnesium sulfate. The solvent was evaporated under reduced pressure. The obtained residue was purified by basic silica gel chromatography (ethyl acetate:hexane=1:1) to give 4-(bromomethyl)-1-fluoro-2-(methylsulfonyl)benzene (1.64 g).

$^1$H NMR (300 MHz, CDCl$_3$) δ ppm 3.24 (3H, s), 4.49 (2H, s), 7.19-7.31 (1H, m), 7.62-7.74 (1H, m), 7.99 (1H, dd, J=6.50, 2.35 Hz).

(Step 2) A solution of 2-amino-5-chloronicotinamide (685 mg) and 4-(bromomethyl)-1-fluoro-2-(methylsulfonyl)benzene obtained in Step 1 (1.6 g) in DMF (10 ml) was stirred at 90° C. for 24 hr. The mixture was allowed to cool to room temperature, methanol and ethyl acetate were added, and the precipitated crystals were collected by filtration. The obtained crystals were dissolved in 1N sodium hydroxide solution, and the solution was extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained yellow solid was dissolved in methanol, 4N hydrogen chloride-ethyl acetate solution (2 ml) was added, and the precipitated crystals were collected by filtration, and recrystallized to give the title compound (510 mg).

$^1$H NMR (300 MHz, DMSO-$d_6$) δ ppm 3.36 (3H, s), 5.62 (2H, s), 7.51-7.65 (1H, m), 7.67-7.78 (1H, m), 7.98 (1H, dd, J=6.44, 2.27 Hz), 8.21 (1H, s), 8.64 (2H, d, J=2.27 Hz), 8.85 (1H, d, J=2.27 Hz), 9.53 (2H, s).

Example 21

5-chloro-1-{5-chloro-2-[(1-methylethyl)sulfonyl]benzyl}-2-imino-1,2-dihydropyridine-3-carboxamide hydrochloride (Step 1) A mixture of 5-chloro-2-fluorobenzonitrile (6.0 g) and sodium propane-2-thiolate (4.16 g) was stirred in N,N-dimethylformamide (30 ml) at room temperature for 18 hr. The reaction solution was treated with 1N hydrochloric acid, and extracted with ethyl acetate. The extract was washed successively with aqueous sodium hydrogen carbonate solution and saturated brine, and dried over magnesium sulfate. The solvent was evaporated under reduced pressure to give 5-chloro-2-[(1-methylethyl)sulfanyl]benzonitrile (7.26 g).

$^1$H NMR (300 MHz, CDCl$_3$) δ ppm 1.34 (6H, d, J=6.82 Hz), 3.48-3.60 (1H, m), 7.40-7.51 (2H, m), 7.62 (1H, d, J=2.27 Hz).

(Step 2) To a suspension of lithium aluminum hydride (1.56 g) in tetrahydrofuran (250 ml) was added a solution of 5-chloro-2-[(1-methylethyl)sulfanyl]benzonitrile obtained in Step 1 (7.25 g) in tetrahydrofuran (50 ml) at 0° C. The mixture was stirred at room temperature for 3 hr, and treated with sodium sulfate 10 hydrate. The mixture was further stirred at room temperature for 30 min, and the inorganic substance was filtered off through celite. The filtrate was concentrated under reduced pressure. The residue was dissolved in methanol, 4N hydrogen chloride-ethyl acetate solution (15 ml) was added, and the solvent was evaporated under reduced pressure. The obtained solid was washed with a mixed solvent of diisopropyl ether-ethyl acetate to give 1-{5-chloro-2-[(1-methylethyl)sulfanyl]phenyl}methanamine hydrochloride (6.57 g).

$^1$H NMR (300 MHz, DMSO-$d_6$) δ ppm 1.23 (6H, d, J=6.59 Hz), 3.38-3.52 (1H, m), 4.16 (2H, s), 7.42-7.50 (1H, m), 7.54-7.60 (1 H, m), 7.68-7.75 (1H, m), 8.62 (3H, s).

(Step 3) To a solution of 1-{5-chloro-2-[(1-methylethyl)sulfanyl]phenyl}methanamine hydrochloride obtained in Step 2 (6.3 g) and triethylamine (5.06 g) in tetrahydrofuran (200 ml) was added di-t-butyl dicarbonate (7.09 g) at room temperature. The mixture was stirred at the same temperature for 3 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (250 ml), and m-chloroperbenzoic acid (14.2 g, containing water: Wako Pure Chemical Industries, Ltd.) was added at room temperature. The mixture was stirred at the same temperature for 14 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=2:3). The obtained residue was dissolved in methanol (50 ml), and 4N hydrogen chloride-ethyl acetate solution (15 ml) was added. The mixture was stirred at 60° C. for 1 hr, and concentrated under reduced pressure. The residue was crystallized from methanol-diisopropyl ether to give 1-{5-chloro-2-[(1-methylethyl)sulfonyl]phenyl}methanamine hydrochloride (5.0 g).

$^1$H NMR (300 MHz, DMSO-$d_6$) δ ppm 1.19 (6H, d, J=6.78 Hz), 3.51-3.63 (1H, m), 4.40 (2H, s), 7.78 (1H, dd, J=8.57, 2.17 Hz), 7.93 (1H, d, J=8.67 Hz), 7.97-8.02 (1H, m), 8.59 (3H, s).

(Step 4) 2-Cyano-2-(3,4-dichloro-5-oxo-2,5-dihydrofuran-2-yl)acetamide (2.07 g), 1-{5-chloro-2-[(1-methylethyl)sulfonyl]phenyl}methanamine hydrochloride obtained in Step 3 (3.0 g) and potassium carbonate (3.65 g) were stirred in ethanol (50 ml) at 85° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained residue was dissolved in methanol, and 4N hydrogen chloride-ethyl acetate solution (3 ml) was added. The mixture was crystallized from methanol-ethyl acetate, and the precipitated crystals were collected by filtration, and recrystallized to give the title compound (1.56 g).

$^1$H NMR (300 MHz, DMSO-$d_6$) δ ppm 1.23 (6H, d, J=6.82 Hz), 3.63-3.93 (1H, m), 5.78 (2H, s), 7.25 (1H, d, J=1.89 Hz), 7.78 (1H, dd, J=8.52, 2.08 Hz), 7.98 (1H, d, J=8.33 Hz), 8.25 (1 H, s), 8.60 (1H, s), 8.72 (2H, s), 9.67 (2H, s).

Example 22

5-chloro-1-[2-(ethylsulfonyl)-5-methylbenzyl]-2-imino-1,2-dihydropyridine-3-carboxamide hydrochloride (Step 1) A mixture of 2-fluoro-5-methylbenzonitrile (7.5 g) and sodium ethanethiolate (4.9 g) was stirred in N,N-dimethylformamide (30 ml) at room temperature for 3 hr. The reaction solution was treated with 1N hydrochloric acid, and extracted with ethyl acetate. The extract was washed with saturated brine, and dried over magnesium sulfate. The solvent was evaporated under reduced pressure to give 2-(ethylsulfanyl)-5-methylbenzonitrile (8.57 g).

$^1$H NMR (300 MHz, CDCl$_3$) δ ppm 1.32 (3H, t, J=7.35 Hz), 2.35 (3 H, s), 3.01 (2H, q, J=7.41 Hz), 7.28-7.38 (2H, m), 7.42-7.47 (1H, m).

(Step 2) To a suspension of lithium aluminum hydride (2.2 g) in tetrahydrofuran (300 ml) was added a solution of 2-(ethylsulfanyl)-5-methylbenzonitrile obtained in Step 1 (8.56 g) in tetrahydrofuran (30 ml) at 0° C. The mixture was stirred at room temperature for 3 hr, and treated with sodium sulfate 10 hydrate. The mixture was further stirred at room temperature for 30 min, and the inorganic substance was filtered off through celite. The filtrate was concentrated under reduced pressure. The residue was dissolved in methanol, and 4N hydrogen chloride-ethyl acetate solution (15 ml) was added. The mixture was crystallized from methanol-ethyl acetate, and recrystallized from ethanol-diisopropyl ether to give 1-[2-(ethylsulfanyl)-5-methylphenyl]methanamine hydrochloride (8.02 g).

$^1$H NMR (300 MHz, DMSO-$d_6$) δ ppm 1.19 (3H, t, J=7.35 Hz), 2.31 (3H, s), 2.91 (2H, q, J=7.28 Hz), 4.10 (2H, s), 7.21 (1H, dd, J=7.91, 1.32 Hz), 7.37 (1H, s), 7.41 (1H, d, J=7.91 Hz), 8.47 (3H, s).

(Step 3) To a solution of 1-[2-(ethylsulfanyl)-5-methylphenyl]methanamine hydrochloride obtained in Step 2 (6.0 g) and triethylamine (5.58 g) in tetrahydrofuran (150 ml) was added di-t-butyl dicarbonate (7.82 g) at room temperature. The mixture was stirred at the same temperature for 13 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (250 ml), and m-chloroperbenzoic acid (15.6 g, containing water: Wako Pure Chemical Industries, Ltd.) was added at room temperature. The mixture was stirred at the same temperature for 3 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (70 ml), and 4N hydrogen chloride-ethyl acetate solution (15 ml) was added. The mixture was stirred at 60° C. for 1 hr, and concentrated under reduced pressure to give crystals. The obtained crystals were washed with ethyl acetate to give 1-[2-(ethylsulfonyl)-5-methylphenyl]methanamine hydrochloride (4.65 g).

$^1$H NMR (300 MHz, DMSO-$d_6$) δ ppm 1.12 (3H, t, J=7.35 Hz), 2.43 (3H, s), 3.30-3.41 (2H, m), 4.35 (2H, s), 7.50 (1H, d, J=8.10 Hz), 7.64 (1H, s), 7.84 (1H, d, J=8.10 Hz), 8.43 (3H, s).

(Step 4) 2-Cyano-2-(3,4-dichloro-5-oxo-2,5-dihydrofuran-2-yl)acetamide (2.35 g), 1-[2-(ethylsulfonyl)-5-methylphenyl]methanamine hydrochloride obtained in Step 3 (3.0 g) and potassium carbonate (4.15 g) were stirred in ethanol (30 ml) at 85° C. for 20 hr. The reaction mixture was treated with 1N sodium hydroxide solution, and extracted with a mixed solvent of ethyl acetate-tetrahydrofuran. The organic layer was washed with saturated brine, and dried over magnesium sulfate. The solvent was evaporated under reduced pressure. The residue was purified by basic silica gel column chromatography (ethyl acetate:hexane=7:3). The obtained residue was dissolved in methanol, and 4N hydrogen chloride-ethyl acetate solution (4 ml) was added. The mixture was crystallized from methanol-ethyl acetate, and the precipitated crystals were collected by filtration, and recrystallized to give the title compound (0.55 g).

$^1$H NMR (300 MHz, DMSO-$d_6$) δ ppm 1.19 (3H, t, J=7.25 Hz), 2.36 (3H, s), 3.46 (2H, q, J=7.22 Hz), 5.78 (2H, s), 6.84 (1H, s), 7.49 (1H, d, J=8.10 Hz), 7.89 (1H, d, J=7.91 Hz), 8.25 (1H, s), 8.59 (1H, d, J=2.07 Hz), 8.70 (1H, s), 8.72 (1H, s), 9.61 (2H, s).

Example 23

5-chloro-2-imino-1-[2-(methylsulfonyl)-5-(trifluoromethoxy)benzyl]-1,2-dihydropyridine-3-carboxamide hydrochloride (Step 1) A mixture of 2-fluoro-5-(trifluoromethoxy)benzonitrile (6.55 g) and sodium methanethiolate (2.46 g) was stirred in N,N-dimethylformamide (50 ml) at room temperature for 3 hr. The reaction solution was treated with 1N hydrochloric acid, and extracted with ethyl acetate. The extract was washed with saturated brine, and dried over magnesium sulfate. The solvent was evaporated under reduced pressure. A solution of the obtained residue in tetrahydrofuran (20 ml) was added at 0° C. to a suspension of lithium aluminum hydride (1.45 g) in tetrahydrofuran (250 ml). The mixture was stirred at room temperature for 2 hr, and treated with sodium sulfate 10 hydrate. The mixture was further stirred at room temperature for 30 min, and the inorganic substance was filtered off through celite. The filtrate was concentrated under reduced pressure. The residue was dissolved in methanol, and 4N hydrogen chloride-ethyl acetate solution (10 ml) was added. The mixture was crystallized from methanol-ethyl acetate to give 1-[2-(methylsulfanyl)-5-(trifluoromethoxy)phenyl]methanamine hydrochloride (4.3 g).

$^1$H NMR (300 MHz, DMSO-$d_6$) δ ppm 2.55 (3H, s), 4.10 (2H, s), 7.34-7.46 (1H, m), 7.48-7.57 (2H, m), 8.50 (3H, s).

(Step 2) To a solution of 1-[2-(methylsulfanyl)-5-(trifluoromethoxy)phenyl]methanamine hydrochloride obtained in Step 1 (3.94 g) and triethylamine (2.91 g) in tetrahydrofuran (150 ml) was added di-t-butyl dicarbonate (4.08 g) at room temperature. The mixture was stirred at the same temperature for 3 hr, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (150 ml), and m-chloroperbenzoic acid (8.88 g, containing water: Wako Pure Chemical Industries, Ltd.) was added at room temperature. The mixture was stirred at the same temperature for 1 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=1:1). The obtained residue was dissolved in methanol (80 ml), and 4N hydrogen chloride-ethyl acetate solution (10 ml) was added. The mixture was stirred at 60° C. for 1 hr, and concentrated under reduced pressure to give 1-[2-(methylsulfonyl)-5-(trifluoromethoxy)phenyl]methanamine hydrochloride (2.96 g) as a solid.

$^1$H NMR (300 MHz, DMSO-$d_6$) δ ppm 3.39 (3H, s), 4.48 (2H, s), 7.71 (1H, d, J=9.09 Hz), 7.85 (1H, s), 8.14 (1H, d, J=8.71 Hz), 8.58 (3H, s).

(Step 3) 2-Cyano-2-(3,4-dichloro-5-oxo-2,5-dihydrofuran-2-yl)acetamide (1.6 g), 1-[2-(methylsulfonyl)-5-(trifluoromethoxy)phenyl]methanamine hydrochloride obtained in Step 2 (2.5 g) and potassium carbonate (2.83 g) were stirred in ethanol (30 ml) at 85° C. for 24 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate:hexane=4:1). The obtained residue was dissolved in methanol, and 4N hydrogen chloride-ethyl acetate solution (4 ml) was added. The mixture was crystallized from methanol-ethyl acetate, and the precipitated crystals were collected by filtration, and recrystallized to give the title compound (1.36 g).

$^1$H NMR (300 MHz, DMSO-$d_6$) δ ppm 3.44 (3H, s), 5.86 (2H, s), 7.06 (1H, d, J=2.07 Hz), 7.70 (1H, d, J=9.42 Hz), 8.21 (1H, d, J=8.67 Hz), 8.24 (1H, s), 8.69 (3H, s), 9.68 (2H, s).

Example 24

5-chloro-1-[2-(ethylsulfonyl)-5-fluorobenzyl]-2-imino-1,2-dihydropyridine-3-carboxamide hydrochloride (Step 1) A mixture of 2-bromo-5-fluorobenzonitrile (5.0 g), sodium ethanethiolate (2.31 g), Pd$_2$(dba)$_3$ (114 mg), Xantphos (145 mg) and N,N-diisopropylethylamine (6.46 g) was stirred in toluene (100 ml) at 90° C. for 9 hr under a nitrogen atmosphere. The reaction mixture was treated with 1N hydrochloric acid, and extracted with ethyl acetate. The organic layer was washed with saturated brine, and dried over magnesium sulfate. The solvent was evaporated under reduced pressure. The residue was purified by silica gel column chromatography (ethyl acetate:hexane=1:19) to give 2-(ethylsulfanyl)-5-fluorobenzonitrile (1.81 g) as a solid.

$^1$H NMR (300 MHz, CDCl$_3$) δ ppm 1.33 (3H, t, J=7.19 Hz), 3.01 (2 H, q, J=7.19 Hz), 7.16-7.29 (1H, m), 7.31-7.42 (1H, m), 7.43-7.70 (1H, m).

(Step 2) To a suspension of lithium aluminum hydride (0.45 g) in tetrahydrofuran (100 ml) was added 2-(ethylsulfanyl)-5-fluorobenzonitrile obtained in Step 1 (1.8 g) at 0° C. The mixture was stirred at room temperature for 3 hr, and treated with sodium sulfate 10 hydrate. The mixture was stirred at room temperature for 30 min, and the inorganic substance was filtered off through celite. The filtrate was concentrated under reduced pressure. The residue was dissolved in methanol, 4N hydrogen chloride-ethyl acetate solution (3 ml) was added, and the solvent was concentrated under reduced pressure. The residue was crystallized from ethanol-diisopropyl ether to give 1-[2-(ethylsulfanyl)-5-fluorophenyl]methanamine hydrochloride (0.93 g).

$^1$H NMR (300 MHz, DMSO-$d_6$) δ ppm 1.18 (3H, t, J=7.38 Hz), 2.93 (2H, q, J=7.45 Hz), 4.16 (2H, s), 7.22-7.31 (1H, m), 7.48 (1H, dd, J=10.03, 2.84 Hz), 7.58 (1H, dd, J=8.71, 5.68 Hz), 8.56 (3H, s).

(Step 3) To a solution of 1-[2-(ethylsulfanyl)-5-fluorophenyl]methanamine hydrochloride obtained in Step 2 (0.92 g) and triethylamine (0.84 g) in tetrahydrofuran (50 ml) was added di-t-butyl dicarbonate (1.18 g) at room temperature. The mixture was stirred at the same temperature for 3 days, treated with 1N hydrochloric acid, and extracted with ethyl acetate. The extract was washed with saturated brine, and dried over magnesium sulfate. The solvent was evaporated under reduced pressure. The obtained residue was dissolved in ethyl acetate (100 ml), and m-chloroperbenzoic acid (2.35 g, containing water: Wako Pure Chemical Industries, Ltd.) was added at room temperature. The mixture was stirred at the same temperature for 4 hr, and treated with aqueous sodium hydrogen carbonate solution. The organic layer was washed with saturated brine, and dried over magnesium sulfate. The solvent was evaporated under reduced pressure. The residue was purified by basic silica gel column chromatography (ethyl acetate:hexane=2:3). The obtained residue was dissolved in methanol (10 ml), and 4N hydrogen chloride-ethyl acetate solution (3 ml) was added. The mixture was stirred at 60° C. for 1 hr, and concentrated under reduced pressure to give 1-[2-(ethylsulfonyl)-5-fluorophenyl]methanamine hydrochloride (0.63 g) as a solid.

$^1$H NMR (300 MHz, DMSO-$d_6$) δ ppm 1.13 (3H, t, J=7.25 Hz), 3.42 (2H, q, J=7.35 Hz), 4.43 (2H, s), 7.47-7.63 (1H, m), 7.77 (1H, d, J=10.17 Hz), 8.02 (1H, dd, J=8.85, 5.65 Hz), 8.61 (3 H, s).

(Step 4) 2-Cyano-2-(3,4-dichloro-5-oxo-2,5-dihydrofuran-2-yl)acetamide (0.43 g), 1-[2-(ethylsulfonyl)-5-fluorophenyl]methanamine hydrochloride obtained in Step 3 (0.55 g) and potassium carbonate (0.75 g) were stirred in ethanol (15 ml) at 85° C. for 16 hr. The reaction mixture was treated with 1N sodium hydroxide solution, and extracted with ethyl acetate. The organic layer was washed with saturated brine, and dried over magnesium sulfate. The solvent was evaporated under reduced pressure. The residue was purified by basic silica gel column chromatography (ethyl acetate). The obtained residue was dissolved in methanol, and 4N hydrogen chloride-ethyl acetate solution (1 ml) was added. The mixture was crystallized from methanol-ethyl acetate, and the precipitated crystals were collected by filtration, and recrystallized to give the title compound (0.19 g).

$^1$H NMR (300 MHz, DMSO-$d_6$) δ ppm 1.21 (3H, t, J=7.35 Hz), 3.44-3.61 (2H, m), 5.82 (2H, s), 7.03 (1H, dd, J=9.89, 2.54 Hz), 7.44-7.64 (1H, m), 8.07 (1H, dd, J=8.85, 5.65 Hz), 8.23 (1H, s), 8.68 (3H, d, J=1.88 Hz), 9.67 (2H, s).

Example 25

5-chloro-1-[5-chloro-2-(dimethylsulfamoyl)benzyl]-2-imino-1,2-dihydropyridine-3-carboxamide hydrochloride (Step 1) To a solution of 2N dimethylamine methanol solution (7.51 ml) in methanol (15 ml) was added dropwise a suspension of 2-[(acetylamino)methyl]-4-chlorobenzenesulfonyl chloride (2.12 g) in tetrahydrofuran (5 ml) under ice-cooling. The mixture was allowed to warm to room temperature, and stirred for 3 hr. The reaction mixture was quenched with water, and extracted with ethyl acetate. The extract was washed with saturated brine, and dried over magnesium sulfate. The solvent was evaporated under reduced pressure. The residue was purified by silica gel column chromatography (ethyl acetate) to give N-[5-chloro-2-(dimethylsulfamoyl)benzyl]acetamide (1.77 g) as a white solid.

$^1$H NMR (300 MHz, CDCl$_3$) δ ppm 1.98 (3H, s), 2.82 (6H, s), 4.66 (2H, d, J=6.4 Hz), 6.45 (1H, br. s.), 7.40 (1H, dd, J=8.3, 2.3 Hz), 7.66 (1H, d, J=2.3 Hz), 7.77 (1H, d, J=8.7 Hz).

(Step 2) To a solution of N-[5-chloro-2-(dimethylsulfamoyl)benzyl]acetamide obtained in Step 1 (1.77 g) in ethanol (20 ml) was added 6N hydrochloric acid (20 ml) at room temperature. The mixture was stirred with heating under reflux for 3 hr, and then stirred overnight at 80° C. The solvent was evaporated under reduced pressure. The residue was collected by filtration, and washed with diethyl ether to give 2-(aminomethyl)-4-chloro-N,N-dimethylbenzenesulfonamide hydrochloride (1.61 g) as a white solid.

$^1$H NMR (300 MHz, DMSO-d$_6$) δ ppm 2.75 (6H, s), 4.36 (2H, br. s.), 7.72 (1H, dd, J=8.6, 2.0 Hz), 7.82-7.90 (1H, m), 7.91-8.05 (1H, m), 8.67 (3H, br. s.).

(Step 3) To a suspension of 2-cyano-2-(3,4-dichloro-5-oxo-2,5-dihydrofuran-2-yl)acetamide (0.50 g) in methanol (10 ml) was added a solution of 2-(aminomethyl)-4-chloro-N,N-dimethylbenzenesulfonamide hydrochloride obtained in Step 2 (0.85 g) and triethylamine (0.58 ml) in methanol (5 ml) at room temperature, and the mixture was stirred overnight at 50° C. The reaction solvent was evaporated under reduced pressure, acetic acid (5 ml) was added, and the mixture was stirred at 50° C. for 2 hr. The solvent was evaporated under reduced pressure, the residue was extracted with 1N hydrochloric acid, and the extract was washed with ethyl acetate. The aqueous layer was basified with 1N aqueous sodium hydroxide solution, and the mixture was extracted with ethyl acetate. The organic layer was dried over sodium sulfate. The solvent was evaporated under reduced pressure. The residue was purified by basic silica gel column chromatography (ethyl acetate:hexane=7:3→1:0). The obtained residue was dissolved in methanol, and 4N hydrogen chloride-ethyl acetate solution (1 ml) was added. The mixture was crystallized from methanol-ethyl acetate. The precipitated crystals were collected by filtration, and recrystallized from methanol-ethyl acetate to give the title compound (0.43 g).

$^1$H NMR (300 MHz, DMSO-d$_6$) δ ppm 2.80 (6H, s), 5.70 (2H, s), 7.34 (1H, d, J=2.3 Hz), 7.75 (1H, dd, J=8.5, 2.1 Hz), 7.92 (1H, d, J=8.7 Hz), 8.23 (1H, br. s.), 8.47 (1H, d), 8.68-8.90 (2H, m), 9.59 (2H, br. s.).

Example 26

5-chloro-1-[5-chloro-2-(methylsulfamoyl)benzyl]-2-imino-1,2-dihydropyridine-3-carboxamide hydrochloride (Step 1) According to the method of Example 25, Steps 1 and 2, 2-(aminomethyl)-4-chloro-N-methylbenzenesulfonamide hydrochloride was obtained from 2-[(acetylamino)methyl]-4-chlorobenzenesulfonyl chloride, a solution of methylamine in tetrahydrofuran, and 6N hydrochloric acid.

$^1$H NMR (300 MHz, DMSO-d$_6$) δ ppm 2.47 (3H, d, J=4.9 Hz), 4.40 (2H, br. s.), 7.71 (1H, dd, J=8.5, 2.1 Hz), 7.87 (2H, d, J=8.5 Hz), 8.07 (1H, br. s.), 8.32-8.68 (3H, m).

(Step 2) 2-Cyano-2-(3,4-dichloro-5-oxo-2,5-dihydrofuran-2-yl)acetamide (0.50 g), 2-(aminomethyl)-4-chloro-N-methylbenzenesulfonamide hydrochloride obtained in Step 1 (0.81 g) and potassium carbonate (0.88 g) were stirred in ethanol (10 ml) overnight at 70° C. The reaction solution was filtered through celite. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (10 mg).

$^1$H NMR (300 MHz, DMSO-d$_6$) δ ppm 2.49 (3H, d, J=1.9 Hz), 5.91 (2H, s), 7.14 (1H, d, J=1.5 Hz), 7.72 (1H, dd, J=8.5, 2.1 Hz), 7.93 (1H, d, J=8.7 Hz), 8.24 (1H, br. s.), 8.31 (2H, br. s.), 8.67 (1H, d, J=1.9 Hz), 8.73 (2H, d, J=1.9 Hz), 9.68 (2H, br. s.).

Example 27

5-chloro-1-[2-(cyclopentylsulfonyl) benzyl]-2-imino-1,2-dihydropyridine-3-carboxamide hydrochloride (Step 1) A solution of methyl 2-sulfanylbenzoate (7.0 g), iodocyclopentane (10.6 g) and potassium carbonate (7.48 g) in tetrahydrofuran-N,N-dimethylformamide (100 ml+10 ml) was stirred at 70° C. for 3 hr. The reaction mixture was poured into water, and the mixture was extracted with ethyl acetate. The reaction mixture was washed successively with 1N hydrochloric acid and saturated brine, dried over magnesium sulfate, and filtered. The solvent was evaporated under reduced pressure. The obtained residue was purified by basic silica gel chromatography (ethyl acetate:hexane=1:4) to give methyl 2-(cyclopentylsulfanyl)benzoate (9.5 g) as an oil. The obtained methyl 2-(cyclopentylsulfanyl)benzoate (5.0 g) was dissolved in ethyl acetate (150 ml), and m-chloroperbenzoic acid (11.5 g, containing water: Wako Pure Chemical Industries, Ltd.) was added at 0° C. The mixture was stirred at room temperature for 0.5 hr, and quenched with aqueous sodium thiosulfate solution. The organic layer was washed with aqueous sodium hydrogen carbonate solution and saturated brine, dried over magnesium sulfate, and filtered. The solvent was evaporated under reduced pressure. The residue was purified by basic silica gel column chromatography (ethyl acetate:hexane=1:4) to give methyl 2-(cyclopentylsulfonyl)benzoate (4.11 g).

$^1$H NMR (300 MHz, CDCl$_3$) δ ppm 1.58-1.71 (2H, m) 1.79-1.97 (4H, m) 2.06-2.21 (2H, m) 3.97 (3H, s) 4.10-4.30 (1H, m) 7.57-7.72 (3H, m) 7.99-8.12 (1H, m).

(Step 2) To a solution of methyl 2-(cyclopentylsulfonyl)benzoate obtained in Step 1 (4.1 g) in tetrahydrofuran-ethanol (100 ml+10 ml) was added lithium borohydride (500 mg) at 0° C. The mixture was stirred at 60° C. for 3 hr, quenched with 1N hydrochloric acid, and extracted with ethyl acetate. The extract was washed with saturated brine, dried over magnesium sulfate, and filtered. The solvent was evaporated under reduced pressure to give [2-(cyclopentylsulfonyl)phenyl]methanol (3.1 g).

¹H NMR (300 MHz, CDCl₃) δ ppm 1.57-1.72 (2H, m) 1.75-1.96 (4H, m) 1.98-2.18 (2H, m) 3.20 (1H, s) 3.52-3.76 (1H, m) 4.90 (2H, s) 7.44-7.69 (3H, m) 7.98 (1H, dd, J=7.82, 1.22 Hz).

(Step 3) Triphenylphosphine (1.19 g) was suspended in acetonitrile (50 ml), bromine (0.24 ml) was added, and the mixture was stirred at room temperature for 30 min. A solution of [2-(cyclopentylsulfonyl)phenyl]methanol obtained in Step 2 (3.1 g) in acetonitrile (10 ml) was added to the reaction mixture. The mixture was stirred at 80° C. for 16 hr, poured into aqueous sodium hydrogen carbonate solution, and extracted with ethyl acetate. The extract was washed with saturated brine, dried over anhydrous magnesium sulfate, and filtered. The solvent was evaporated under reduced pressure. The obtained residue was purified by basic silica gel chromatography (ethyl acetate:hexane=1:5) to give 2-(bromomethyl)-2-(cyclopentylsulfonyl)benzene (0.95 g) as an oil.

¹H NMR (300 MHz, CDCl₃) δ ppm 1.59-1.73 (2H, m) 1.77-1.97 (4H, m) 1.99-2.17 (2H, m) 3.84-4.02 (1H, m) 5.07 (2H, s) 7.40-7.54 (1H, m) 7.56-7.67 (2H, m) 8.01 (1H, d, J=7.72 Hz).

(Step 4) A solution of 2-amino-5-chloronicotinamide (200 mg) and 1-(bromomethyl)-2-(cyclopentylsulfonyl)benzene obtained in Step 3 (530 mg) in DMF (5 ml) was stirred at 90° C. for 20 hr. The mixture was allowed to cool to room temperature, ethyl acetate was added, and the precipitated crystals were collected by filtration. The obtained crystals were dissolved in aqueous sodium hydrogen carbonate solution, and the solution was extracted with a mixed solvent of ethyl acetate-tetrahydrofuran. The organic layer was washed with saturated brine, dried over magnesium sulfate, and filtered. The solvent was evaporated under reduced pressure. The residue was purified by basic silica gel column chromatography (ethyl acetate:hexane=3:1). The obtained residue was dissolved in methanol, and 4N hydrogen chloride-ethyl acetate solution (0.5 ml) was added. The mixture was crystallized from methanol-ethyl acetate, and the precipitated crystals were collected by filtration, and recrystallized to give the title compound (70 mg).

¹H NMR (300 MHz, DMSO-d₆) δ ppm 1.46-2.05 (8H, m) 3.98-4.20 (1H, m) 5.84 (2H, s) 6.98-7.08 (1H, m) 7.61-7.76 (2H, m) 7.95-8.08 (1H, m) 8.25 (1H, s) 8.63 (1H, d, J=1.88 Hz) 8.65-8.75 (2H, m) 9.60 (2H, s).

Example 28

5-chloro-1-(5-chloro-2-sulfamoylbenzyl)-2-imino-1,2-dihydropyridine-3-carboxamide hydrochloride 2-Cyano-2-(3,4-dichloro-5-oxo-2,5-dihydrofuran-2-yl)acetamide (0.29 g), 2-(aminomethyl)-4-chlorobenzenesulfonamide hydrochloride (0.42 g) and potassium carbonate (0.52 g) were stirred in ethanol (10 ml) at 70° C. overnight. The reaction solution was filtered through celite. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (30 mg).

¹H NMR (300 MHz, DMSO-d₆) δ ppm 5.81 (2H, s), 7.07-7.34 (1H, m), 7.66-7.79 (1H, m), 7.81-7.94 (1H, m), 7.95-8.06 (1H, m), 8.17-8.35 (1H, m), 8.37-8.54 (1H, m), 8.58-8.73 (2H, m), 9.55 (2H, br. s.).

Example 29

5-chloro-1-(5-fluoro-2-sulfamoylbenzyl)-2-imino-1,2-dihydropyridine-3-carboxamide hydrochloride (Step 1) To chlorosulfonic acid (50 ml) was added N-(3-fluorobenzyl)acetamide (11.8 g) by small portions under ice-cooling. The mixture was allowed to warm to room temperature, and stirred at 70° C. for 3 hr. The reaction mixture was poured into ice water to quench the reaction, and extracted with ethyl acetate. The extract was washed with saturated brine, dried over anhydrous magnesium sulfate, and filtered. The solvent was evaporated under reduced pressure to give 2-[(acetylamino)methyl]-4-fluorobenzenesulfonyl chloride (14.1 g) as a white solid.

¹H NMR (300 MHz, CDCl₃) δ ppm 2.03 (3H, s), 4.83 (2H, d, J=6.4 Hz), 6.28 (1H, br. s.), 7.19 (1H, ddd, J=9.3, 7.0, 2.7 Hz), 7.49 (1H, dd, J=9.1, 2.7 Hz), 8.12 (1H, dd, J=8.7, 5.3 Hz).

(Step 2) To a solution of 8N ammonia methanol solution (2 ml) in methanol (15 ml) was added dropwise a suspension of 2-[(acetylamino)methyl]-4-fluorobenzenesulfonyl chloride obtained in Step 1 (1.34 g) in tetrahydrofuran (5 ml) under ice-cooling, and the mixture was allowed to warm to room temperature, and stirred for 1 hr. The reaction mixture was quenched with water, and extracted with ethyl acetate. The extract was washed with saturated brine, and dried over magnesium sulfate. The solvent was evaporated under reduced pressure. The residue was purified by silica gel column chromatography (ethyl acetate) to give N-(5-fluoro-2-sulfamoylbenzyl)acetamide (1.34 g) as a white solid.

¹H NMR (300 MHz, DMSO-d₆) δ ppm 1.96 (3H, s), 4.68 (2H, d, J=6.2 Hz), 7.17 (1H, dd, J=10.2, 2.6 Hz), 7.28 (1H, td, J=8.5, 2.8 Hz), 7.52-7.63 (2H, m), 7.92 (1H, dd, J=8.8, 5.7 Hz), 8.45 (1H, t, J=6.1 Hz).

(Step 3) To a solution of N-(5-fluoro-2-sulfamoylbenzyl)acetamide obtained in Step 2 (2.7 g) in ethanol (20 ml) was added hydrochloric acid (10 ml) at room temperature, and the mixture was stirred with heating under reflux for 3 hr, and then overnight at 80° C. The solvent was evaporated under reduced pressure. The residue was collected by filtration, and washed with diethyl ether to give 2-(aminomethyl)-4-fluorobenzenesulfonamide hydrochloride (1.49 g) as a white solid.

¹H NMR (300 MHz, DMSO-d₆) δ ppm 4.43 (2H, d, J=3.8 Hz), 7.46 (1H, td, J=8.5, 2.7 Hz), 7.59 (1H, d, J=9.8 Hz), 7.70-7.88 (2H, m), 7.99 (1H, dd, J=8.7, 5.7 Hz), 8.55 (3H, br. s.).

(Step 4) 2-Cyano-2-(3,4-dichloro-5-oxo-2,5-dihydrofuran-2-yl)acetamide (1.0 g), 2-(aminomethyl)-4-fluorobenzenesulfonamide hydrochloride obtained in Step 3 (1.23 g) and potassium carbonate (1.76 g) were stirred in ethanol (20 ml) overnight at 70° C. The reaction solution was filtered through celite. The solvent was evaporated under reduced pressure. The residue was purified by basic silica gel column chromatography (ethyl acetate:hexane=7:3→1:0). 4N Hydrochloride-ethyl acetate solution (1 ml) was added to the obtained yellow oil, and the precipitated crystals were collected by filtration, and recrystallized to give the title compound (68 mg).

¹H NMR (300 MHz, DMSO-d₆) δ ppm 5.91 (2H, br. s.), 6.96 (1H, d, J=9.8 Hz), 7.49 (1H, td, J=8.5, 2.6 Hz), 7.87 (2H, br. s.), 8.05 (1H, dd, J=8.9, 5.7 Hz), 8.23 (1H, s), 8.49-8.65 (1H, m), 8.72 (2H, br. s.), 9.64 (2H, br. s.).

Example 30

5-chloro-1-[5-fluoro-2-(methylsulfamoyl)benzyl]-2-imino-1,2-dihydropyridine-3-carboxamide hydrochloride (Step 1) According to the method of Example 29, Steps 2 and 3, 2-(aminomethyl)-4-fluoro-N-methylbenzenesulfonamide hydrochloride was synthesized using 2-[(acetylamino)methyl]-4-fluorobenzenesulfonyl chloride, a solution of methylamine in tetrahydrofuran, and hydrochloric acid.

$^1$H NMR (300 MHz, DMSO-$d_6$) δ ppm 2.46 (3H, d, J=4.9 Hz), 4.41 (2H, q, J=5.7 Hz), 7.48 (1H, td, J=8.3, 2.7 Hz), 7.58-7.68 (1H, m), 7.90-8.04 (2H, m), 8.51 (3H, br. s.).

(Step 2) To a suspension of 2-cyano-2-(3,4-dichloro-5-oxo-2,5-dihydrofuran-2-yl)acetamide (0.90 g) in methanol (10 ml) was added a solution of 2-(aminomethyl)-4-fluoro-N-methylbenzenesulfonamide hydrochloride obtained in Step 1 (1.17 g) and triethylamine (1.6 ml) in methanol (5 ml) at room temperature, and the mixture was stirred overnight at 50° C. The reaction solvent was evaporated under reduced pressure, acetic acid (5 ml) was added, and the mixture was stirred at 50° C. for 2 hr. The solvent was evaporated under reduced pressure, the residue was extracted with 1N hydrochloric acid, and the extract was washed with ethyl acetate. The aqueous layer was basified with 1N aqueous sodium hydroxide solution, the mixture was partitioned with ethyl acetate, and the organic layer was dried over sodium sulfate. The solvent was evaporated under reduced pressure. The residue was purified by basic silica gel column chromatography (ethyl acetate:hexane=7:3→1:0). The obtained residue was dissolved in methanol, and 4N hydrogen chloride-ethyl acetate solution (1 ml) was added. The mixture was crystallized from methanol-ethyl acetate. The precipitated crystals were collected by filtration, and recrystallized from methanol-ethyl acetate to give the title compound (0.74 g).

$^1$H NMR (300 MHz, DMSO-$d_6$) δ ppm 2.47 (3H, d), 5.92 (2H, s), 6.98 (1H, dd, J=9.9, 2.4 Hz), 7.47 (1H, td, J=8.4, 2.5 Hz), 7.99 (1H, dd, J=8.7, 5.7 Hz), 8.09-8.35 (2H, m), 8.55-8.88 (3H, m), 9.68 (2H, br. s.).

Example 31

5-chloro-1-[2-(dimethylsulfamoyl)-5-fluorobenzyl]-2-imino-1,2-dihydropyridine-3-carboxamide hydrochloride (Step 1) According to the method of Example 29, Steps 2 and 3, 2-(aminomethyl)-4-fluoro-N,N-dimethylbenzenesulfonamide hydrochloride was synthesized using 2-[(acetylamino)methyl]-4-fluorobenzenesulfonyl chloride, a solution of dimethylamine in tetrahydrofuran, and hydrochloric acid.

$^1$H NMR (300 MHz, DMSO-$d_6$) δ ppm 2.74 (6H, s), 4.37 (2H, d, J=4.9 Hz), 7.50 (1H, td, J=8.3, 2.7 Hz), 7.76 (1H, dd, J=10.2, 2.7 Hz), 7.93 (1H, dd, J=9.1, 5.7 Hz), 8.69 (3H, br. s.).

(Step 2) To a suspension of 2-cyano-2-(3,4-dichloro-5-oxo-2,5-dihydrofuran-2-yl)acetamide (1.0 g) in methanol (10 ml) was added a solution of 2-(aminomethyl)-4-fluoro-N,N-dimethylbenzenesulfonamide hydrochloride obtained in Step 1 (1.37 g) and triethylamine (1.6 ml) in methanol (5 ml) at room temperature, and the mixture was stirred overnight at 50° C. The reaction solvent was evaporated under reduced pressure, acetic acid (5 ml) was added, and the mixture was stirred at 50° C. for 2 hr. The solvent was evaporated under reduced pressure, the residue was extracted with 1N hydrochloric acid, and the extract was washed with ethyl acetate. The aqueous layer was basified with 1N aqueous sodium hydroxide solution, the mixture was partitioned with ethyl acetate, and the organic layer was dried over sodium sulfate. The solvent was evaporated under reduced pressure. The residue was purified by basic silica gel column chromatography (ethyl acetate:hexane=7:3→1:0). The obtained residue was dissolved in methanol, and 4N hydrogen chloride-ethyl acetate solution (1 ml) was added. The mixture was crystallized from methanol-ethyl acetate. The precipitated crystals were collected by filtration, and recrystallized from methanol-ethyl acetate to give the title compound (0.11 g).

$^1$H NMR (300 MHz, DMSO-$d_6$) δ ppm 2.79 (6H, s), 5.70 (2H, s), 7.14 (1H, dd, J=10.0, 2.4 Hz), 7.51 (1H, td, J=8.4, 2.6 Hz), 7.99 (1H, dd, J=8.9, 5.7 Hz), 8.23 (1H, s), 8.51 (1H, d, J=2.1 Hz), 8.71 (2H, s), 9.54 (2H, br. s.).

Example 32 methyl 2-[(3-carbamoyl-5-chloro-2-iminopyridin-1 (2H)-yl)methyl]-4-chlorobenzoate hydrobromide (Step 1) To a solution of 4-chloro-2-methylbenzoic acid (5.0 g) in methanol (40 ml) was added concentrated sulfuric acid at room temperature. The mixture was stirred at 70° C. for 3 hr, neutralized with 1N sodium hydroxide, and extracted with ethyl acetate. The organic layer was washed with saturated brine, dried over magnesium sulfate, and filtered. The solvent was evaporated under reduced pressure. The residue was purified by silica gel chromatography (ethyl acetate:hexane=1:19→3:7) to give methyl 4-chloro-2-methylbenzoate (5.05 g) as an oil.

$^1$H NMR (300 MHz, CDCl$_3$) δ ppm 2.58 (3H, s) 3.88 (3H, s) 7.14-7.30 (2H, m) 7.83-7.92 (1H, m).

(Step 2) A solution of N-bromosuccinimide (6.33 g), 2,2'-azobis(isobutyronitrile) (0.27 g) and methyl 4-chloro-2-methylbenzoate obtained in Step 1 (5.05 g) in t-butyl acetate (80 ml) was stirred overnight at 90° C. The mixture was allowed to cool to room temperature, poured into aqueous sodium hydrogen carbonate solution, and extracted with ethyl acetate. The organic layer was washed with saturated brine, dried over magnesium sulfate, and filtered. The solvent was evaporated under reduced pressure. The residue was purified by silica gel chromatography (ethyl acetate:hexane=0:1-3:17) to give methyl 4-chloro-2-bromomethylbenzoate (6.05 g) as a white solid.

$^1$H NMR (300 MHz, CDCl$_3$) δ ppm 3.94 (3H, s) 4.91 (2H, s) 7.35 (1H, dd, J=8.4, 2.2 Hz) 7.47 (1H, d, J=2.1 Hz), 7.93 (1H, d, J=8.3 Hz).

(Step 3) A solution of 2-amino-5-chloronicotinamide (202 mg) and methyl 4-chloro-2-bromomethylbenzoate obtained in Step 2 (470 mg) in DMF (5 ml) was stirred overnight at 90° C. The mixture was allowed to cool to room temperature, ethyl acetate was added, and the precipitated crystals were collected by filtration. The obtained crystals were recrystallized from ethanol and ethyl acetate to give the title compound (78 mg).

$^1$H NMR (300 MHz, DMSO-$d_6$) δ ppm 3.90 (3H, s) 5.79 (2H, s) 6.92 (1H, d, J=1.9 Hz) 7.63 (1H, dd, J=1.9, 8.5 Hz) 8.08 (1H, d, J=8.5 Hz) 8.21 (1H, s) 8.52-8.72 (3H, m) 9.12-9.78 (2H, m).

Example 33

5-chloro-1-[5-fluoro-2-(morpholin-4-ylsulfonyl)benzyl]-2-imino-1,2-dihydropyridine-3-carboxamide hydrochloride (Step 1) To a solution of morpholine (0.36 ml) and triethylamine (0.58 ml) in methanol (15 ml) was added dropwise a suspension of 2-[(acetylamino)methyl]-4-fluorobenzenesulfonyl chloride (1.00 g) in tetrahydrofuran (5 ml) under ice-cooling, and the mixture was allowed to warm to room temperature, and stirred for 1 hr. The reaction mixture was quenched with saturated brine, and extracted with ethyl acetate. The extract was washed with saturated brine, and dried over magnesium sulfate. The solvent was evaporated under reduced pressure. The residue was purified by silica gel chromatography (ethyl acetate). The obtained oil was dissolved in ethanol (20 ml), hydrochloric acid (10 ml) was added, and the mixture was stirred with heating under reflux for 9 hr. The solvent was evaporated under reduced pressure, and the residue was collected by filtration, and washed with ethyl acetate to give 1-[5-fluoro-2-(morpholin-4-ylsulfonyl)phenyl]methanamine hydrochloride (0.58 g) as a white solid.

$^1$H NMR (300 MHz, DMSO-$d_6$) δ ppm 3.02 (1H, t), 3.07 (3H, t), 3.66 (3H, t), 3.78 (1H, t, J=1.7 Hz), 4.34 (0.6H, s), 4.37 (1.4H, s), 7.18-7.30 (0.3H, m), 7.34 (0.3H, dd, J=9.7, 2.7 Hz), 7.53 (0.7H, td, J=8.5, 2.6 Hz), 7.75 (0.7H, dd, J=10.2, 2.6 Hz), 7.83 (0.3H, dd, J=8.6, 6.1 Hz), 7.96 (0.7H, dd, J=8.9, 5.7 Hz), 8.57 (3H, br. s.).

(Step 2) To a suspension of 2-cyano-2-(3,4-dichloro-5-oxo-2,5-dihydrofuran-2-yl)acetamide (0.36 g) in methanol (10 ml) was added a solution of 1-[5-fluoro-2-(morpholin-4-ylsulfonyl)phenyl]methanamine hydrochloride obtained in Step 1 (0.58 g) and triethylamine (0.65 ml) in methanol (5 ml) at room temperature, and the mixture was stirred overnight at 50° C. The reaction solvent was evaporated under reduced pressure, acetic acid (5 ml) was added, and the mixture was stirred at 50° C. for 2 hr. The solvent was evaporated under reduced pressure, the residue was extracted with 1N hydrochloric acid, and the extract was washed with ethyl acetate. The aqueous layer was basified with 1N aqueous sodium hydroxide solution, the mixture was partitioned with ethyl acetate, and the organic layer was dried over sodium sulfate. The solvent was evaporated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.17 g).

$^1$H NMR (300 MHz, DMSO-$d_6$) δ ppm 3.01-3.20 (2H, m), 3.12 (2H, d, J=4.7 Hz), 3.69 (2H, br. s.), 3.67 (2H, d, J=5.1 Hz), 5.70 (2H, s), 7.13 (1H, dd, J=10.0, 2.4 Hz), 7.53 (1H, td, J=8.4, 2.4 Hz), 8.00 (1H, dd, J=8.9, 5.7 Hz), 8.23 (1H, br. s.), 8.53 (1H, d, J=2.1 Hz), 8.72 (2H, br. s.), 9.55 (2H, br. s.).

Example 34

5-chloro-1-[5-chloro-2-(2-oxoimidazolidin-1-yl)benzyl]-2-imino-1,2-dihydropyridine-3-carboxamide hydrochloride (Step 1) Using 2-bromo-5-chlorobenzonitrile and imidazolidin-2-one, and in the same manner as in the Example 35, Steps 1 to 3, 1-[2-(aminomethyl)-4-chlorophenyl]imidazolidin-2-one hydrochloride was obtained.

$^1$H NMR (400 MHz, CDCl$_3$) δ ppm 3.44 (2H, t, J=7.8 Hz) 3.86 (2H, t, J=7.8 Hz) 3.91 (2H, q, J=5.8 Hz) 7.18 (1H, br.s.) 7.41 (1H, d, J=8.4 Hz) 7.47 (1H, dd, J=2.4, 8.8 Hz) 7.70 (1H, d, J=2.4 Hz) 8.38 (3H, br.s.).

(Step 2) Using 1-[2-(aminomethyl)-4-chlorophenyl]imidazolidin-2-one hydrochloride obtained in Step 1, and in the same manner as in Example 33, Step 2, the title compound was obtained.

$^1$H NMR (300 MHz, DMSO-$d_6$) δ ppm 3.39-3.57 (2H, m) 3.82-3.98 (2H, m) 5.46 (2H, s) 7.17 (1H, s) 7.31 (1H, s) 7.47-7.60 (2H, m) 8.19 (1H, s) 8.58-8.75 (3H, m) 9.25-9.66 (2H, m).

Example 35

5-chloro-1-[5-chloro-2-(2-oxopyrrolidin-1-yl)benzyl]-2-imino-1,2-dihydropyridine-3-carboxamide hydrochloride (Step 1) To a solution (139 ml) of 2-bromo-5-chlorobenzonitrile (15.0 g), pyrrolidin-2-one (7.90 ml) and cesium carbonate (45.2 g) in 1,4-dioxane were added tris(dibenzylideneacetone)dipalladium (1.59 g) and 4,5-bis(biphenylphosphino)-9,9-dimethylxanthine (2.0 g) at room temperature under a nitrogen atmosphere, and the mixture was heated under reflux for 3 hr. The mixture was allowed to cool to room temperature, and extracted with ethyl acetate and water. The organic layer was filtered through celite, and washed with ethyl acetate. The filtrate was dried over sodium sulfate, and filtered. The solvent was evaporated under reduced pressure. The obtained residue was purified by column chromatography (ethyl acetate:hexane=1:10→1:1) to give 5-chloro-2-(2-oxopyrrolidin-1-yl)benzonitrile (12.5 g) as yellow crystals.

$^1$H NMR (400 MHz, CD$_3$OD) δ ppm 2.24-2.31 (2H, m) 2.62 (2H, t, J=8.0 Hz), 3.94 (2H, t, J=6.8 Hz) 7.39 (1H, d, J=9.2 Hz) 7.60 (1H, dd, J=2.4, 8.8 Hz) 7.67 (1H, d, J=2.4 Hz).

(Step 2) To a solution (227 ml) of 5-chloro-2-(2-oxopyrrolidin-1-yl)benzonitrile obtained in Step 1 (5.0 g) and nickel chloride 6 hydrate (0.54 g) in methanol was gradually added sodium tetrahydroborate (4.29 g) at 0° C., and the mixture was stirred for 10 min. Water (50 ml) was slowly added to quench the reaction. The solvent was evaporated under reduced pressure. The residue was extracted with ethyl acetate and water, and the aqueous layer was extracted with ethyl acetate three times. The organic layers were combined, washed with saturated brine, dried over sodium sulfate, and filtered. The solvent was evaporated under reduced pressure. The residue was dissolved in methylene chloride (150 ml), a solution of di-t-butyl dicarbonate (5.15 ml) in methylene chloride (40 ml) was added to this solution, and triethylamine (7.82 ml) was added at room temperature. The reaction mixture was stirred at room temperature for 2 hr, and quenched with 5% hydrochloric acid (10 ml) and water (50 ml). The organic layer was washed with water and saturated brine, dried over sodium sulfate, and filtered. The solvent was evaporated under reduced pressure. The residue was purified by silica gel column chromatography (ethyl acetate:hexane=1:10→1:5) to give t-butyl [5-chloro-2-(2-oxopyrrolidin-1-yl)benzyl]carbamate (2.70 g).

$^1$H NMR (400 MHz, DMSO-$d_6$) δ ppm 1.36 (9H, s) 2.11-2.14 (2H, m) 2.44-2.48 (2H, m) 3.63-3.66 (2H, m) 4.03-4.08 (2H, m) 5.54 (1H, br.s.) 6.98-7.01 (1H, m) 7.15-7.18 (1H, m) 7.34-7.35 (1H, m).

(Step 3) To a solution (83 ml) of t-butyl [5-chloro-2-(2-oxopyrrolidin-1-yl)benzyl]carbamate obtained in Step 2 (2.70 g) in ethyl acetate was added 4N hydrogen chloride-dioxane solution (7.27 ml) at 0° C., and the mixture was stirred overnight at room temperature. The purified white crystals were collected by filtration, and washed with ethyl acetate to give 1-[2-(aminomethyl)-4-chlorophenyl]pyrrolidin-2-one hydrochloride (1.20 g).

$^1$H NMR (400 MHz, CDCl$_3$) δ ppm 2.14 (2H, quintet, J=3.6 Hz) 2.48 (2H, t, J=7.8 Hz) 3.81 (2H, t, J=7.0 Hz) 3.87

(2H, q, J=5.8 Hz) 7.43 (1H, d, J=8.4 Hz) 7.53 (1H, dd, J=2.4, 8.4 Hz) 7.77 (1H, d, J=2.4 Hz) 8.41 (3H, br.s.).

(Step 4) Using 1-[2-(aminomethyl)-4-chlorophenyl]pyrrolidin-2-one hydrochloride obtained in Step 3, and in the same manner as in Example 33, Step 2, the title compound was obtained.

$^1$H NMR (300 MHz, DMSO-$d_6$) δ ppm 2.06-2.21 (2H, m) 2.38-2.52 (2H, m) 3.81 (2H, t, J=6.8 Hz) 5.35 (2H, s) 7.29 (1H, d, J=2.3 Hz) 7.46-7.61 (2H, m) 8.20 (1H, s) 8.48-8.67 (3H, m) 9.18-9.51 (2H, m).

Example 36

5-chloro-1-[5-fluoro-2-(piperidin-1-ylsulfonyl)benzyl]-2-imino-1,2-dihydropyridine-3-carboxamide hydrochloride (Step 1) According to the method of Example 29, Steps 2 and 3, 1-[5-fluoro-2-(piperidin-1-ylsulfonyl)phenyl]methanamine hydrochloride was synthesized using 2-[(acetylamino)methyl]-4-fluorobenzenesulfonyl chloride, piperidine and hydrochloric acid.

$^1$H NMR (300 MHz, DMSO-$d_6$) δ ppm 1.32-1.90 (6H, m), 2.88-3.13 (4H, m), 4.36 (2H, br. s.), 7.49 (1H, td, J=8.3, 2.7 Hz), 7.73 (1H, dd, J=10.2, 2.7 Hz), 7.95 (1H, dd, J=8.7, 5.7 Hz), 8.62 (3H, br. s.).

(Step 2) A suspension of 2-cyano-2-(3,4-dichloro-5-oxo-2,5-dihydrofuran-2-yl)acetamide (1.0 g), 1-[5-fluoro-2-(piperidin-1-ylsulfonyl)phenyl]methanamine hydrochloride obtained in Step 1 (1.58 g) and potassium carbonate (1.76 g) in ethanol (10 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.75 g).

$^1$H NMR (300 MHz, DMSO-$d_6$) δ ppm 1.49 (2H, br. s.), 1.59 (4H, br. s.), 3.12 (4H, t, J=5.0 Hz), 5.71 (2H, s), 7.15 (1H, dd, J=9.8, 2.4 Hz), 7.51 (1H, td, J=8.4, 2.4 Hz), 7.98 (1H, dd, J=8.9, 5.7 Hz), 8.24 (1H, s), 8.48 (1H, d, J=2.1 Hz), 8.68-8.85 (2H, m), 9.55 (2H, br. s.).

Example 37

5-chloro-1-[5-fluoro-2-(phenylsulfamoyl)benzyl]-2-imino-1,2-dihydropyridine-3-carboxamide hydrochloride (Step 1) According to the method of Example 33, Step 1, 2-(aminomethyl)-4-fluoro-N-phenylbenzenesulfonamide hydrochloride was synthesized using 2-[(acetylamino)methyl]-4-fluorobenzenesulfonyl chloride, aniline, triethylamine and hydrochloric acid.

$^1$H NMR (300 MHz, DMSO-$d_6$) δ ppm 4.23 (2H, s), 6.09-6.72 (2H, m), 6.83 (1H, t, J=7.4 Hz), 6.90-7.03 (2H, m), 7.11 (2H, t, J=8.0 Hz), 7.23 (1H, td, J=8.5, 2.7 Hz), 7.47 (1H, dd, J=10.2, 2.7 Hz), 7.87 (1H, dd, J=8.7, 6.1 Hz).

(Step 2) A suspension of 2-cyano-2-(3,4-dichloro-5-oxo-2,5-dihydrofuran-2-yl)acetamide (0.26 g), 2-(aminomethyl)-4-fluoro-N-phenylbenzenesulfonamide hydrochloride obtained in Step 1 (0.37 g) and potassium carbonate (0.45 g) in ethanol (20 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.12 g).

$^1$H NMR (300 MHz, DMSO-$d_6$) δ ppm 6.03 (2H, br. s.), 7.02 (1H, d, J=9.1 Hz), 7.07-7.16 (1H, m), 7.16-7.24 (2H, m), 7.24-7.40 (3H, m), 7.69 (1H, d, J=7.6 Hz), 8.24 (1H, s), 8.50 (1H, br. s.), 8.70 (2H, br. s.), 9.69 (2H, br. s.), 10.84 (1H, br. s.).

Example 38

5-chloro-1-[5-fluoro-2-(pyrrolidin-1-ylsulfonyl)benzyl]-2-imino-1,2-dihydropyridine-3-carboxamide hydrochloride (Step 1) According to the method of Example 29, Steps 2 and 3, 1-[5-fluoro-2-(pyrrolidin-1-ylsulfonyl)phenyl]methanamine hydrochloride was synthesized using 2-[(acetylamino)methyl]-4-fluorobenzenesulfonyl chloride, pyrrolidine and hydrochloric acid.

$^1$H NMR (300 MHz, DMSO-$d_6$) δ ppm 1.83 (4H, dt, J=6.6, 3.4 Hz), 3.20 (4H, dd, J=9.2, 4.3 Hz), 4.38 (2H, s), 7.49 (1H, td, J=8.5, 2.6 Hz), 7.72 (1H, d, J=10.0 Hz), 7.96 (1H, dd, J=8.9, 5.8 Hz), 8.61 (3H, br. s.).

(Step 2) A suspension of 2-cyano-2-(3,4-dichloro-5-oxo-2,5-dihydrofuran-2-yl)acetamide (0.87 g), 1-[5-fluoro-2-(pyrrolidin-1-ylsulfonyl)phenyl]methanamine hydrochloride obtained in Step 1 (1.15 g) and potassium carbonate (1.54 g) in ethanol (10 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.20 g).

$^1$H NMR (300 MHz, DMSO-$d_6$) δ ppm 1.74-1.93 (4H, m), 3.22-3.30 (4H, m), 5.70 (2H, s), 7.17 (1H, dd, J=9.7, 2.5 Hz), 7.50 (1H, td, J=8.4, 2.5 Hz), 8.03 (1H, dd, J=8.9, 5.7 Hz), 8.23 (1H, s), 8.48 (1H, d, J=2.1 Hz), 8.69 (2H, d, J=2.1 Hz), 9.50 (2H, br. s.).

Example 39

5-chloro-1-[2-(cyclopropylsulfamoyl)-5-fluorobenzyl]-2-imino-1,2-dihydropyridine-3-carboxamide hydrochloride (Step 1) A solution of 2-[(acetylamino)methyl]-4-fluorobenzenesulfonyl chloride (1.5 g), cyclopropylamine (0.43 ml) and triethylamine (0.87 ml) in tetrahydrofuran (15 ml) was stirred at room temperature for 2 hr. The reaction mixture was quenched with saturated brine, and extracted with ethyl acetate. The extract was washed with saturated brine, and dried over magnesium sulfate. The solvent was evaporated under reduced pressure. The residue was crystallized from methanol-water to give N-[2-(cyclopropylsulfamoyl)-5-fluorobenzyl]acetamide (1.06 g) as a white solid.

$^1$H NMR (300 MHz, CHLOROFORM-d) δ ppm 0.45-0.64 (4H, m), 2.00 (3H, s), 2.26-2.36 (1H, m), 4.70 (2H, d, J=6.6

Hz), 5.47-5.67 (1H, m), 6.32-6.54 (1H, m), 6.96-7.23 (1H, m), 7.27-7.33 (1H, m), 7.98-8.19 (1H, m).

(Step 2) To a solution of N-[2-(cyclopropylsulfamoyl)-5-fluorobenzyl]acetamide obtained in Step 1 (2.22 g) in ethanol (20 ml) was added hydrochloric acid (10 ml) at room temperature, and the mixture was stirred overnight at 80° C. The reaction solvent was evaporated under reduced pressure, saturated aqueous sodium hydrogen carbonate solution was added, and the mixture was extracted with ethyl acetate. The extract was washed with saturated brine, and dried over sodium sulfate. The solvent was evaporated under reduced pressure to give 2-(aminomethyl)-N-cyclopropyl-4-fluorobenzenesulfonamide (0.60 g) as a white solid.

$^1$H NMR (300 MHz, CDCl$_3$) δ ppm 0.42-0.60 (4H, m), 1.64 (3H, br. s.), 2.06-2.17 (1H, m), 4.28 (2H, s), 7.04-7.19 (2H, m), 8.09 (1H, dd, J=9.3, 5.5 Hz).

(Step 3) A suspension of 2-cyano-2-(3,4-dichloro-5-oxo-2,5-dihydrofuran-2-yl)acetamide (0.48 g), 2-(aminomethyl)-N-cyclopropyl-4-fluorobenzenesulfonamide obtained in Step 2 (0.60 g) and potassium carbonate (0.85 g) in ethanol (20 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.06 g).

$^1$H NMR (300 MHz, DMSO-d$_6$) δ ppm 0.46 (2H, d, J=2.7 Hz), 0.50-0.61 (2H, m), 2.24 (1H, td, J=6.5, 2.8 Hz), 5.83 (2H, s), 7.06 (1H, dd, J=9.7, 2.5 Hz), 7.51 (1H, td, J=8.5, 2.7 Hz), 8.06 (1H, dd, J=8.7, 5.7 Hz), 8.23 (1H, br. s.), 8.39 (1H, d, J=2.3 Hz), 8.46 (1H, d, J=1.9 Hz), 8.67 (2H, d, J=1.9 Hz), 9.59 (2H, br. s.).

Example 40

5-chloro-1-[2-(ethylsulfamoyl)-5-fluorobenzyl]-2-imino-1,2-dihydropyridine-3-carboxamide hydrochloride (Step 1) According to the method of Example 29, Steps 1 and 2, 2-(aminomethyl)-N-ethyl-4-fluorobenzenesulfonamide was synthesized using 2-[(acetylamino)methyl]-4-fluorobenzenesulfonyl chloride, ethylamine and hydrochloric acid.

$^1$H NMR (300 MHz, CDCl$_3$) δ ppm 1.06 (3H, t, J=7.3 Hz), 2.87 (2H, q), 4.30 (2H, s), 6.97-7.17 (2H, m), 7.39-7.64 (1H, m), 8.02 (1H, dd, J=8.4, 6.3 Hz).

(Step 2) A suspension of 2-cyano-2-(3,4-dichloro-5-oxo-2,5-dihydrofuran-2-yl)acetamide (0.19 g), 2-(aminomethyl)-N-ethyl-4-fluorobenzenesulfonamide obtained in Step 1 (0.23 g) and potassium carbonate (0.34 g) in ethanol (10 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.04 g).

$^1$H NMR (300 MHz, DMSO-d$_6$) δ ppm 1.05 (3H, t, J=7.2 Hz), 2.88 (2H, d, J=1.3 Hz), 5.80 (2H, s), 7.05 (1H, dd, J=9.9, 2.2 Hz), 7.48 (1H, td, J=8.5, 2.6 Hz), 8.01 (1H, dd, J=8.9, 5.7 Hz), 8.04-8.14 (1H, m), 8.22 (1H, br. s.), 8.48 (1H, s), 8.65 (2H, br. s.), 9.55 (2H, br. s.).

Example 41

5-chloro-2-imino-1-[2-(methylsulfonyl)benzyl]-1,2-dihydropyridine-3-carboxamide hydrochloride 2-Cyano-2-(3,4-dichloro-5-oxo-2,5-dihydrofuran-2-yl)acetamide (1.8 g), 1-[2-(methylsulfonyl)phenyl]methanamine hydrochloride (1.5 g) and potassium carbonate (1.8 g) were stirred in ethanol (30 ml) at 80° C. for 16 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate). The obtained residue was dissolved in methanol, 4N hydrogen chloride-ethyl acetate solution (2 ml) was added, and the mixture was crystallized from methanol-ethyl acetate. The precipitated crystals were collected by filtration, and recrystallized to give the title compound (0.29 g).

$^1$H NMR (300 MHz, DMSO-d$_6$) δ ppm 3.41 (3H, s) 5.89 (2H, s) 6.82-7.06 (1H, m) 7.62-7.76 (2H, m) 8.00-8.14 (1H, m) 8.25 (1H, s) 8.63-8.78 (3H, m) 9.63 (2H, s).

Example 42

5-chloro-1-{5-fluoro-2-[(2-methoxyethyl)sulfamoyl]benzyl}-2-imino-1,2-dihydropyridine-3-carboxamide hydrochloride (Step 1) According to the method of Example 39, Steps 1 and 2, 2-(aminomethyl)-4-fluoro-N-(2-methoxyethyl)benzenesulfonamide was synthesized using 2-[(acetylamino)methyl]-4-fluorobenzenesulfonyl chloride, 2-methoxyethanamine, triethylamine and hydrochloric acid.

$^1$H NMR (300 MHz, CDCl$_3$) δ ppm 3.01 (2H, t, J=5.3 Hz), 3.21 (3H, s), 3.31-3.45 (2H, m), 4.28 (2H, s), 7.10 (2H, d, J=8.3 Hz), 8.01 (1H, dd, J=8.7, 5.7 Hz).

(Step 2) A suspension of 2-cyano-2-(3,4-dichloro-5-oxo-2,5-dihydrofuran-2-yl)acetamide (0.4 g), 2-(aminomethyl)-4-fluoro-N-(2-methoxyethyl)benzenesulfonamide obtained in Step 1 (0.61 g) and potassium carbonate (0.71 g) in ethanol (10 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.29 g).

$^1$H NMR (300 MHz, DMSO-d$_6$) δ ppm 2.96-3.09 (2H, m), 3.14 (3H, s), 3.33-3.42 (2H, m), 5.84 (2H, s), 7.03 (1H, dd, J=9.9, 2.4 Hz), 7.47 (1H, td, J=8.4, 2.5 Hz), 8.03 (1H, dd, J=8.8, 5.7 Hz), 8.23 (1H, br. s.), 8.27-8.39 (1H, m), 8.48 (1H, s), 8.69 (2H, br. s.), 9.58 (2H, br. s.).

Example 43 methyl{2-[(3-carbamoyl-5-chloro-2-iminopyridin-1(2H)-yl)methyl]-4-chlorophenyl}carbamate hydrochloride (Step 1) To a solution of 2-amino-5-chlorobenzonitrile (1.95 g) and dimethylaminopyridine (20.3 mg) in N,N-dimethylacetamide (15 ml) was added dropwise methyl chlorocarbonate (3.5 ml) at room temperature, and the mixture was stirred at 90° C. for 5 hr. The mixture was allowed to cool to room temperature, poured into water, and extracted with ethyl acetate. The organic layer was washed with saturated brine, dried over magnesium sulfate, and filtered. The solvent was evaporated under reduced pressure. The residue was purified by silica gel column chromatography (ethyl acetate:hexane=3:20-1:4) to give methyl (4-chloro-2-cyanophenyl)carbamate (1.21 g) as a white solid.

$^1$H NMR (300 MHz, CDCl$_3$) δ ppm 3.83 (3H, s) 7.06-7.21 (1H, m) 7.49-7.58 (2H, m) 8.28 (1H, d, J=9.4 Hz).

(Step 2) To a solution of nickel chloride (0.74 g), di-t-butyl dicarbonate (2.6 ml) and methyl (4-chloro-2-cyanophenyl)carbamate obtained in Step 1 (1.21 g) in methanol (50 ml) was added sodium borohydride (1.52 g) by small portions at 0° C., and the solution was stirred overnight at room temperature. The solvent was evaporated under reduced pressure, the residue was dissolved in ethyl acetate and saturated sodium hydrogen carbonate, and the insoluble substance was filtered off through celite. The filtrate was extracted with ethyl acetate, and the organic layer was washed with saturated brine, dried over sodium sulfate, and filtered. The solvent was evaporated under reduced pressure. The residue was purified by silica gel column chromatography (ethyl acetate:hexane=1:9-2:3) to give methyl (2-{[(t-butoxycarbonyl)amino]methyl}-4-chlorophenyl)carbamate (1.25 g) as a white solid.

$^1$H NMR (300 MHz, CDCl$_3$) δ ppm 1.41-1.49 (9H, m) 3.78 (3H, s) 4.21 (2H, d, J=6.8 Hz) 4.92-5.09 (1H, m) 7.12 (1H, d, J=2.4 Hz) 7.23-7.29 (1H, m) 7.94 (1H, d, J=8.7 Hz) 8.59-8.78 (1H, m).

(Step 3) To a solution (2 ml) of methyl (2-{[(t-butoxycarbonyl)amino]methyl}-4-chlorophenyl)carbamate obtained in Step 2 (1.25 g) in ethanol was added 4N hydrogen chloride-ethyl acetate solution (2 ml) at room temperature, and the mixture was stirred overnight. The resulting crystals were collected by filtration, and recrystallized from ethanol and ethyl acetate to give methyl [2-(aminomethyl)-4-chlorophenyl]carbamate hydrochloride (0.85 g) as a white solid.

$^1$H NMR (300 MHz, DMSO-d$_6$) δ ppm 3.68 (3H, s) 4.00 (2H, s) 7.38-7.54 (2H, m) 7.60 (1H, br.s.) 8.19-8.56 (3H, m) 9.38 (1H, br.s.).

(Step 4) 2-Cyano-2-(3,4-dichloro-5-oxo-2,5-dihydrofuran-2-yl)acetamide (1.0 g), methyl [2-(aminomethyl)-4-chlorophenyl]carbamate hydrochloride obtained in Step 3 (2.12 g) and potassium carbonate (1.18 g) were stirred in ethanol (10 ml) overnight at 80° C. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=7:3→1:0). The obtained residue was dissolved in ethanol, 4N hydrogen chloride-ethyl acetate solution (2 ml) was added, and the mixture was crystallized from ethanol-ethyl acetate. The precipitated crystals were collected by filtration, and recrystallized to give the title compound (42 mg).

$^1$H NMR (300 MHz, DMSO-d$_6$) δ ppm 3.68 (3H, s) 5.36-5.52 (2H, m) 7.12 (1H, d, J=1.7 Hz) 7.43-7.59 (2H, m) 8.16-8.27 (1H, m) 8.32-8.44 (1H, m) 8.63 (2H, br.s.) 9.20-9.60 (3H, m).

Example 44

5-chloro-1-[5-chloro-2-(2-oxo-1,3-oxazolidin-3-yl)benzyl]-2-imino-1,2-dihydropyridine-3-carboxamide hydrochloride (Step 1) To a solution (of 2-oxazolidone (1.23 g) in N,N-dimethylformamide (20 ml) was added sodium hydride (0.62 g) under ice-cooling, and the mixture was stirred for 5 min. 5-Chloro-2-fluorobenzonitrile (2.0 g) was added, and the mixture was stirred at room temperature for 2 hr. Saturated brine was added to the reaction solution, and the mixture was extracted with ethyl acetate. The organic layer was washed with saturated brine, dried over magnesium sulfate, and filtered. The solvent was evaporated under reduced pressure. The residue was crystallized from ethyl acetate-hexane to give 5-chloro-2-(2-oxo-1,3-oxazolidin-3-yl)benzonitrile (1.8 g) as a white solid.

$^1$H NMR (300 MHz, CDCl$_3$) δ ppm 4.21 (2H, t, J=7.8 Hz), 4.57 (2H, t, J=7.8 Hz), 7.50-7.84 (3H, m).

(Step 2) To a solution of nickel chloride (1.0 g), di-t-butyl dicarbonate (3.75 ml) and 5-chloro-2-(2-oxo-1,3-oxazolidin-3-yl)benzonitrile obtained in Step 1 (1.8 g) in methanol (30 ml) was added sodium borohydride (2.14 g) by small portions at 0° C., and the mixture was stirred overnight at room temperature. The solvent was evaporated under reduced pressure, the residue was dissolved in ethyl acetate and saturated sodium hydrogen carbonate, and the insoluble substance was filtered off through celite. The filtrate was extracted with ethyl acetate, and the organic layer was washed with saturated brine, dried over magnesium sulfate, and filtered. The solvent was evaporated under reduced pressure. The residue was purified by silica gel column chromatography (ethyl acetate-hexane) to give tert-butyl [5-chloro-2-(2-oxo-1,3-oxazolidin-3-yl)benzyl]carbamate (2.21 g) as a white solid.

$^1$H NMR (300 MHz, CDCl$_3$) δ ppm 1.45 (9H, s), 3.89-4.05 (2H, m), 4.28 (2H, d, J=6.2 Hz), 4.45-4.71 (2H, m), 5.24 (1H, br. s.), 7.12-7.20 (1H, m), 7.27-7.36 (1H, m), 7.45 (1H, d, J=2.4 Hz).

(Step 3) To a solution of tert-butyl [5-chloro-2-(2-oxo-1,3-oxazolidin-3-yl)benzyl]carbamate obtained in Step 2 (2.21 g) in methanol (27 ml) was added 2N hydrogen chloride-methanol solution (10 ml) at room temperature, and the mixture was stirred for 3 hr. The reaction solution was concentrated under reduced pressure. The resulting crystals were collected by filtration, and washed with ethyl acetate to give 3-[2-(aminomethyl)-4-chlorophenyl]-1,3-oxazolidin-2-one hydrochloride (1.30 g) as a white solid.

$^1$H NMR (300 MHz, DMSO-d$_6$) δ ppm 2.88 (2H, s), 3.48-3.64 (4H, m), 4.05 (2H, t, J=7.8 Hz), 7.09 (2H, d, J=1.1 Hz), 7.29 (1H, s), 7.93 (2H, br. s.).

(Step 4) A suspension of 2-cyano-2-(3,4-dichloro-5-oxo-2,5-dihydrofuran-2-yl)acetamide (0.50 g), 3-[2-(aminomethyl)-4-chlorophenyl]-1,3-oxazolidin-2-one hydrochloride obtained in Step 3 (0.67 g) and potassium carbonate (0.88 g) in ethanol (15 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.29 g).

$^1$H NMR (300 MHz, DMSO-d$_6$) δ ppm 4.07 (2H, t, J=7.8 Hz), 4.50 (2H, t, J=7.8 Hz), 5.51 (2H, s), 7.36 (1H, d, J=1.9 Hz), 7.52-7.71 (2H, m), 8.22 (1H, s), 8.59 (1H, d, J=2.1 Hz), 8.62-8.72 (2H, m), 9.50 (2H, br. s.).

Example 45

5-chloro-2-imino-1-{2-[(1-methylethyl)sulfonyl]benzyl}-1,2-dihydropyridine-3-carboxamide hydrochloride 2-Cyano-2-(3,4-dichloro-5-oxo-2,5-dihydrofuran-2-yl)acetamide (2 g), 1-{2-[(1-methylethyl)sulfonyl]phenyl}methanamine hydrochloride (2.55 g) and potassium carbonate (2.94 g) were stirred in ethanol (50 ml) at 90° C. for 16 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4: 1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.46 g).

$^1$H NMR (300 MHz, DMSO-$d_6$) δ ppm 1.24 (6H, d, J=6.78 Hz) 3.74 (1H, quin, J=6.69 Hz) 5.81 (2H, s) 7.06 (1H, dd, J=7.44, 1.22 Hz) 7.71 (2H, m) 7.99 (1H, dd, J=7.44, 1.79 Hz) 8.24 (1H, br. s.) 8.60 (1H, d, J=2.07 Hz) 8.63-8.76 (2H, m) 9.60 (2H, br. s.).

Example 46

5-chloro-1-{5-fluoro-2-[(methylsulfonyl)amino] benzyl}-2-imino-1,2-dihydropyridine-3-carboxamide hydrochloride (Step 1) A suspension of 2,5-difluorobenzonitrile (12.4 g), methanesulfonamide (9.3 g) and potassium carbonate (13.6 g) in DMSO (360 ml) was stirred overnight at 120° C. The reaction solution was poured into 1N hydrochloric acid, and extracted with ethyl acetate. The organic layer was washed with saturated brine, dried over magnesium sulfate, and filtered. The solvent was evaporated under reduced pressure. The residue was crystallized from ethyl acetate-hexane to give N-(2-cyano-4-fluorophenyl]methanesulfonamide (6.57 g) as a white solid.

$^1$H NMR (300 MHz, DMSO-$d_6$) δ ppm 3.09 (3H, s), 7.49-7.57 (1H, m), 7.58-7.68 (1H, m), 10.02 (1H, s).

(Step 2) According to the method of Example 44, Steps 2 and 3, N-[2-(aminomethyl)-4-fluorophenyl]methanesulfonamide hydrochloride (1.92 g) was obtained as a white solid, using nickel chloride, sodium borohydride, di-t-butyl dicarbonate, 2N hydrogen chloride-methanol solution and N-(2-cyano-4-fluorophenyl]methanesulfonamide obtained in Step 1.

$^1$H NMR (300 MHz, DMSO-$d_6$) δ ppm 3.02 (3H, s), 3.57 (3H, s), 4.13 (2H, s), 7.31 (1H, dd, J=8.3, 3.0 Hz), 7.43 (1H, dd, J=8.9, 5.5 Hz), 7.50 (1H, dd, J=9.8, 1.7 Hz), 8.38 (2H, br. s.).

(Step 3) A suspension of 2-cyano-2-(3,4-dichloro-5-oxo-2,5-dihydrofuran-2-yl)acetamide (0.77 g), N-[2-(aminomethyl)-4-fluorophenyl]methanesulfonamide hydrochloride obtained in Step 2 (1.0 g) and potassium carbonate (1.36 g) in ethanol (15 ml) was stirred overnight at 70° C. The reaction solution was filtered through celite, and concentrated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.04 g).

$^1$H NMR (300 MHz, DMSO-$d_6$) δ ppm 3.11 (3H, s), 5.55 (2H, s), 7.06 (1H, dd, J=9.3, 2.7 Hz), 7.34 (1H, td, J=8.5, 2.8 Hz), 7.51 (1H, dd, J=8.8, 5.4 Hz), 8.22 (1H, s), 8.42 (1H, d, J=1.9 Hz), 8.64 (2H, br. s.), 9.45 (3H, m).

Example 47

5-chloro-1-{5-chloro-2-[(dimethylcarbamoyl)amino] benzyl}-2-imino-1,2-dihydropyridine-3-carboxamide hydrochloride (Step 1) To a solution of 2-amino-5-chlorobenzonitrile (5.0 g) and dimethylaminopyridine (0.12 g) in dimethylacetamide (25 ml) was added dropwise phenyl chlorocarbonate (6.2 ml) at room temperature, and the mixture was stirred overnight. The reaction mixture was poured into water, and extracted twice with ethyl acetate. The organic layer was washed with saturated brine, dried over magnesium sulfate, and filtered. The solvent was evaporated under reduced pressure. The residue was purified by silica gel column chromatography (ethyl acetate:hexane=1:5→3:7) to give phenyl (4-chloro-2-cyanophenyl)carbamate (7.04 g).

$^1$H NMR (300 MHz, CDCl$_3$) δ ppm 7.17-7.33 (3H, m) 7.37-7.49 (3H, m) 7.54-7.63 (2H, m) 8.21-8.30 (1H, m).

(Step 2) To a solution of phenyl (4-chloro-2-cyanophenyl) carbamate obtained in Step 1 (3.0 g) in tetrahydrofuran (30 ml) was added 2N dimethylamine tetrahydrofuran solution at room temperature, and the mixture was stirred overnight. The reaction mixture was poured into saturated sodium hydrogen carbonate solution, and extracted twice with ethyl acetate. The organic layer was washed with saturated brine, dried over magnesium sulfate, and filtered. The solvent was evaporated under reduced pressure. The residue was purified by silica gel column chromatography (ethyl acetate:hexane=1:4→2:3) to give 3-(4-chloro-2-cyanophenyl)-1,1-dimethylurea (2.33 g).

$^1$H NMR (300 MHz, CDCl$_3$) δ ppm 3.09 (6H, s) 6.92-7.03 (1H, m) 7.45-7.54 (2H, m) 8.27-8.34 (1H, m).

(Step 3) Using 3-(4-chloro-2-cyanophenyl)-1,1-dimethylurea obtained in Step 2 (2.33 g), and in the same manner as in Example 43, Step 2, tert-butyl {5-chloro-2-[(dimethylcarbamoyl)amino]benzyl}carbamate (1.77 g) was obtained.

$^1$H NMR (300 MHz, CDCl$_3$) δ ppm 1.41 (9H, s) 3.07 (6H, s) 4.17 (2H, d, J=6.6 Hz) 4.96-5.13 (1H, m) 7.11 (1H, d, J=2.5 Hz) 7.23 (1H, dd, J=8.9, 2.5 Hz) 7.70 (1H, d, J=8.9 Hz) 8.17-8.32 (1H, m).

(Step 4) Using tert-butyl {5-chloro-2-[(dimethylcarbamoyl)amino]benzyl}carbamate obtained in Step 3 (1.77 g), and in the same manner as in Example 43, Step 3, 3-[2-(aminomethyl)-4-chlorophenyl]-1,1-dimethylurea hydrochloride (1.18 g) was obtained.

$^1$H NMR (300 MHz, DMSO-$d_6$) δ ppm 2.96 (6H, s) 3.88 (2H, q, J=5.3 Hz) 7.25 (1H, d, J=8.5 Hz) 7.42 (1H, dd, J=2.5, 8.5 Hz) 7.59 (1H, d, J=2.5 Hz) 8.10-8.32 (3H, m) 8.42 (1H, s).

(Step 5) 2-Cyano-2-(3,4-dichloro-5-oxo-2,5-dihydrofuran-2-yl)acetamide (0.5 g) and 3-[2-(aminomethyl)-4-chlorophenyl]-1,1-dimethylurea hydrochloride obtained in Step 4 (1.12 g) were stirred in ethanol (5 ml) overnight at 90° C. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=7: 3→1:0). The obtained residue was dissolved in ethanol, 4N hydrogen chloride-ethyl acetate solution (1 ml) was added, and the mixture was crystallized from ethanol-ethyl acetate. The precipitated crystals were collected by filtration, and recrystallized to give the title compound (46 mg).

¹H NMR (300 MHz, DMSO-d₆) δ ppm 2.95 (6H, s) 5.41 (2H, s) 7.06 (1H, d, J=2.5 Hz) 7.26 (1H, d, J=8.5 Hz) 7.45 (1H, dd, J=2.5, 8.5 Hz) 8.19 (1H, s) 8.47-8.77 (4H, m) 9.23-9.77 (2H, m).

Example 48

5-chloro-2-imino-1-{2-[(2-methylpropyl)sulfonyl]benzyl}-1,2-dihydropyridine-3-carboxamide hydrochloride 2-Cyano-2-(3,4-dichloro-5-oxo-2,5-dihydrofuran-2-yl)acetamide (2.0 g), 1-{2-[(2-methylpropyl)sulfonyl]phenyl}methanamine hydrochloride (2.69 g) and potassium carbonate (2.94 g) were stirred in ethanol (30 ml) at 90° C. for 5 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (1.02 g).

¹H NMR (300 MHz, DMSO-d₆) δ ppm 1.08 (6H, d, J=6.78 Hz) 2.25 (1H, dt, J=13.38, 6.69 Hz) 3.39 (2H, d, J=6.59 Hz) 5.84 (2H, br. s.) 6.86-7.07 (1H, m) 7.57-7.80 (2H, m) 7.92-8.11 (1H, m) 8.24 (1H, br. s.) 8.50-8.80 (3H, m) 9.60 (2H, br. s.).

Example 49

5-chloro-2-imino-1-{2-[(2-methoxyethyl)sulfonyl]benzyl}-1,2-dihydropyridine-3-carboxamide hydrochloride (Step 1) To a suspension of 2-[(2-methoxyethyl)sulfanyl]benzamide (12.0 g) in tetrahydrofuran (122 ml) was added lithium aluminum hydride (13.4 g) at 0° C. under a nitrogen atmosphere. The reaction mixture was heated under reflux for 5 hr, cooled to 0° C., and quenched successively with water (15 ml) and 15% aqueous sodium hydroxide solution (15 ml). The mixture was filtered through celite, and washed with dichloromethane. The filtrate was washed with saturated brine, and the organic layer was dried over sodium sulfate, and filtered. The solvent was evaporated under reduced pressure to give 1-{2-[(2-methoxyethyl)sulfanyl]phenyl}methanamine (16.0 g) as an oil.

¹H NMR (400 MHz, CDCl₃) δ ppm 3.12 (2H, t, J=6.8 Hz), 3.36 (3H, s), 3.57 (2H, t, J=6.4 Hz), 3.95 (2H, s), 7.21 (2H, td, J=7.1, 2.0 Hz), 7.30-7.33 (1H, m), 7.37 (1H, d, J=7.4, 1.4 Hz).

(Step 2) To a solution of 1-{2-[(2-methoxyethyl)sulfanyl]phenyl}methanamine obtained in Step 1 (12.0 g) in dichloromethane (122 ml) were added triethylamine (8.55 ml) and di-t-butyl dicarbonate (26.5 g) at 0° C. The reaction mixture was stirred at room temperature for 12 hr, and concentrated under reduced pressure, and the residue was dissolved in water (15 ml) and dichloromethane (150 ml). The aqueous layer was separated, and further extracted twice with dichloromethane. The obtained organic layers were combined, dried over sodium sulfate, and filtered. The solvent was evaporated under reduced pressure. The residue was purified by silica gel column chromatography (ethyl acetate:hexane=1:5) to give tert-butyl {2-[(2-methoxyethyl)sulfanyl]benzyl}carbamate (16.0 g) as a white solid.

¹H NMR (400 MHz, CDCl₃) δ ppm 1.44 (9H, s), 3.10 (2H, t, J=6.4 Hz), 3.36 (3H, s), 3.54 (2H, t, J=6.4 Hz), 4.43 (2H, d, J=6 Hz), 5.27 (1H, brs), 7.40 (1H, td, J=7.8, 1.4 Hz), 7.24 (1H, td, J=7.5, 2.0 Hz), 7.35 (1H, d, J=7.2 Hz), 7.40 (1H, d, J=7.8, 1.4 Hz).

(Step 3) tert-Butyl {2-[(2-methoxyethyl)sulfanyl]benzyl}carbamate obtained in Step 2 (16.0 g) was dissolved in ethyl acetate (108 ml), and m-chloroperbenzoic acid (27.9 g, 70-75 w %) was added at room temperature. The mixture was stirred at the same temperature for 18 hr, and washed twice with 2N aqueous sodium hydroxide solution. The organic layer was dried over sodium sulfate, and filtered. The solvent was evaporated under reduced pressure to give tert-butyl {2-[(2-methoxyethyl)sulfonyl]benzyl}carbamate (15.0 g) as a white solid.

¹H NMR (400 MHz, CDCl₃) δ ppm 1.42 (9H, s), 3.21 (3H, s), 3.47 (2H, t, J=6.0 Hz), 3.76 (2H, t, J=6.0 Hz), 4.60 (2H, d, J=6.8 Hz), 5.25 (1H, brs), 7.45-7.49 (1H, m), 7.59-7.65 (2H, m), 7.97 (1H, d, J=7.6 Hz).

(Step 4) tert-Butyl {2-[(2-methoxyethyl)sulfonyl]benzyl}carbamate obtained in Step 3 (15.0 g) was dissolved in ethyl acetate (91 ml), and 4N hydrogen chloride-1,4-dioxane solution (34.2 ml) was added at 0° C. The mixture was stirred at room temperature for 12 hr, and the precipitated crystals were collected by filtration, and washed with ethyl acetate to give 1-{2-[(2-methoxyethyl)sulfonyl]phenyl}methanamine hydrochloride (10.0 g).

¹H NMR (400 MHz, DMSO-d₆) δ ppm 3.08 (3H, s), 3.61-3.64 (2H, m), 3.68-3.71 (2H, m), 4.38 (2H, s), 7.64-7.68 (1H, m), 7.75-7.82 (2H, m), 7.95 (1H, dd, J=7.6, 1.2 Hz), 8.48 (3H, brs).

(Step 5) 2-Cyano-2-(3,4-dichloro-5-oxo-2,5-dihydrofuran-2-yl)acetamide (2.0 g), 1-{2-[(2-methoxyethyl)sulfonyl]phenyl}methanamine hydrochloride obtained in Step 4 (2.71 g) and potassium carbonate (2.94 g) were stirred in ethanol (30 ml) at 90° C. for 16 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.38 g).

¹H NMR (300 MHz, DMSO-d₆) δ ppm 3.14 (3H, s) 3.69-3.76 (2H, m) 3.79-3.91 (2H, m) 5.86 (2H, br. s.) 6.87-7.15 (1H, m) 7.56-7.79 (2H, m) 7.98-8.09 (1H, m) 8.25 (1H, s) 8.61 (1H, s) 8.67-8.87 (2H, m) 9.59 (2H, br. s.).

Example 50

5-chloro-1-[2-(dimethylsulfamoyl)benzyl]-2-imino-1,2-dihydropyridine-3-carboxamide hydrochloride (Step 1) To a mixture of dimethylamine (49.6 ml, 2M tetrahydrofuran solution) and triethylamine (3.46 ml) was added a solution of 2-cyanobenzene-1-sulfonyl chloride (5.0 g) in tetrahydrofuran (20 ml) at room temperature. The mixture was stirred at the same temperature for 2 hr, and concentrated under reduced pressure. The residue was suspended in water, and filtered. The filtered solid was dissolved in dichloromethane, the solution was washed with water, and the organic layer was dried over sodium sulfate, and filtered. The solvent was evaporated under reduced pressure. The residue was purified by silica gel column chromatography (ethyl acetate:hexane=1:2) to give 2-cyano-N,N-dimethylbenzenesulfonamide (5.1 g).

$^1$H NMR (400 MHz, CDCl$_3$) δ ppm 2.89 (6H, s), 7.71 (1H, td, J=7.6, 1.6 Hz), 7.77 (1H, td, J=7.8, 1.6 Hz), 7.89-7.91 (1H, m), 8.06 (1H, dd, J=8.0, 1.2 Hz).

(Step 2) A solution of 2-cyano-N,N-dimethylbenzenesulfonamide obtained in Step 1 (9.25 g) and Raney-nickel (0.52 g) in methanol (220 ml) was stirred at room temperature for 17 hr under a hydrogen atmosphere (50 psi). The reaction mixture was filtered through celite, and concentrated under reduced pressure. The residue was purified by silica gel column chromatography (ethyl acetate→ethyl acetate:methanol=5:1). The obtained residue was dissolved in ethyl acetate (67 ml), and 4N hydrogen chloride-1,4-dioxane solution (33.6 ml) was added at 0° C. The mixture was stirred at room temperature for 1 hr, and the precipitated crystals were collected by filtration, and washed with ethyl acetate to give 2-(aminomethyl)-N,N-dimethylbenzenesulfonamide hydrochloride (7.3 g).

$^1$H NMR (400 MHz, DMSO-d$_6$) δ ppm 2.75 (6H, s), 4.36 (2H, s), 7.64 (1H, td, J=7.6, 1.6 Hz), 7.78 (1H, td, J=7.5, 1.2 Hz), 7.85 (2H, dd, J=8.0, 1.2 Hz), 8.66 (3H, brs).

(Step 3) 2-Cyano-2-(3,4-dichloro-5-oxo-2,5-dihydrofuran-2-yl)acetamide (1.56 g), 2-(aminomethyl)-N,N-dimethylbenzenesulfonamide hydrochloride obtained in Step 2 (2 g) and potassium carbonate (2.3 g) were stirred in ethanol (20 ml) at 80° C. for 16 hr. The reaction mixture was poured into 1N aqueous sodium hydroxide solution, and extracted with a mixed solvent of ethyl acetate-tetrahydrofuran. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.13 g).

$^1$H NMR (300 MHz, DMSO-d$_6$) δ ppm 2.80 (6H, s) 5.73 (2H, s) 6.97-7.29 (1H, m) 7.56-7.77 (2H, m) 7.83-7.99 (1H, m) 8.24 (1H, s) 8.47 (1H, d, J=2.26 Hz) 8.70 (2H, d, J=2.07 Hz) 9.45 (2H, br. s.).

Example 51

5-chloro-2-imino-1-[2-(pyrrolidin-1-ylsulfonyl)benzyl]-1,2-dihydropyridine-3-carboxamide hydrochloride (Step 1) To a mixture of pyrrolidine (4.92 ml) and triethylamine (6.91 ml) was added a solution of 2-cyanobenzene-1-sulfonyl chloride (10.0 g) in tetrahydrofuran (40 ml) at 0° C. The mixture was stirred at room temperature for 2 hr, and concentrated under reduced pressure. The residue was suspended in water, and the suspension was filtered. The filtered solid was dissolved in dichloromethane, and the solution was washed with water. The organic layer was dried over sodium sulfate, and filtered. The solvent was evaporated under reduced pressure. The residue was purified by silica gel column chromatography (ethyl acetate:hexane=1:2) to give 2-pyrrolidin-1-ylsulfonyl)benzonitrile (11.3 g).

$^1$H NMR (400 MHz, CDCl$_3$) δ ppm 1.90-1.93 (4H, m), 3.42-3.45 (4H, m), 7.69 (1H, td, J=7.5, 1.6 Hz), 7.76 (1H, td, J=7.8, 1.6 Hz), 7.87-7.89 (1H, m), 8.09 (1H, dd, J=7.8, 1.6 Hz).

(Step 2) A solution of 2-(pyrrolidin-1-ylsulfonyl)benzonitrile obtained in Step 1 (0.1 g) and Raney-nickel (5 mg) in methanol (2.2 ml) was stirred at room temperature for 19 hr under a hydrogen atmosphere (50 psi). The reaction mixture was filtered through celite, and concentrated under reduced pressure. The residue was purified by silica gel column chromatography (ethyl acetate→ethyl acetate:methanol=5:1) to give 1-[2-(pyrrolidin-1-ylsulfonyl)phenyl]methanamine (70 mg).

$^1$H NMR (400 MHz, CDCl$_3$) δ ppm 1.86 (2H, brs), 1.88-1.93 (4H, m), 3.30-3.34 (4H, m), 4.16 (2H, s), 7.37-7.41 (1H, m), 7.55-7.57 (2H, m), 7.89 (1H, d, J=8.4 Hz).

(Step 3) 1-[2-(Pyrrolidin-1-ylsulfonyl)phenyl]methanamine obtained in Step 2 (3.88 g) was dissolved in ethyl acetate (32 ml), and 4N hydrogen chloride-1,4-dioxane solution (16 ml) was added at 0° C. The mixture was stirred at room temperature for 1 hr, and the precipitated crystals were collected by filtration, and washed with ethyl acetate to give 1-[2-(pyrrolidin-1-ylsulfonyl)phenyl]methanamine hydrochloride (4.07 g).

$^1$H NMR (400 MHz, DMSO-d$_6$) δ ppm 1.80-1.99 (4H, m), 3.20-3.38 (4H, m), 4.37 (2H, s), 7.64 (1H, td, J=7.5, 1.2 Hz), 7.77 (1H, td, J=7.5, 1.6 Hz), 7.82 (1H, dd, J=7.6, 1.2 Hz), 7.88 (1H, dd, J=8.0, 1.2 Hz), 8.63 (3H, brs).

(Step 4) 2-Cyano-2-(3,4-dichloro-5-oxo-2,5-dihydrofuran-2-yl)acetamide (1.42 g), 1-[2-(pyrrolidin-1-ylsulfonyl)phenyl]methanamine hydrochloride obtained in Step 3 (2.0 g) and potassium carbonate (2.08 g) were stirred in ethanol (20 ml) at 90° C. for 8 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.88 g).

$^1$H NMR (300 MHz, DMSO-d$_6$) δ ppm 1.85 (4H, dt, J=6.55, 3.41 Hz) 3.22-3.31 (4H, m) 5.74 (2H, s) 7.12-7.28 (1H, m) 7.60-7.78 (2H, m) 7.89-8.01 (1H, m) 8.24 (1H, s) 8.42 (1H, d, J=2.07 Hz) 8.65-8.84 (2H, m) 9.48 (2H, br. s.).

Example 52

5-chloro-2-imino-1-[2-(morpholin-4-ylsulfonyl)benzyl]-1,2-dihydropyridine-3-carboxamide hydrochloride 2-Cyano-2-(3,4-dichloro-5-oxo-2,5-dihydrofuran-2-yl) acetamide (1.34 g), 1-[2-(morpholin-4-ylsulfonyl)phenyl] methanamine hydrochloride (2.0 g) and potassium carbonate (1.97 g) were stirred in ethanol (20 ml) at 90° C. for 16 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.82 g).

$^1$H NMR (300 MHz, DMSO-d$_6$) δ ppm 3.01-3.19 (4H, m) 3.56-3.78 (4H, m) 5.73 (2H, s) 7.11 (1H, d, J=8.29 Hz) 7.59-7.79 (2H, m) 7.88-7.99 (1H, m) 8.24 (1H, s) 8.51 (1H, d, J=2.26 Hz) 8.70 (2H, br. s.) 9.49 (2H, br. s.).

Example 53

5-chloro-2-imino-1-[2-(phenylsulfamoyl)benzyl]-1,2-dihydropyridine-3-carboxamide hydrochloride 2-Cyano-2-(3,4-dichloro-5-oxo-2,5-dihydrofuran-2-yl) acetamide (1.31 g), 2-(aminomethyl)-N-phenylbenzenesulfonamide hydrochloride (2.0 g) and potassium carbonate (1.93 g) were stirred in ethanol (20 ml) at 90° C. for 20 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate→ethyl acetate:methanol=9:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.90 g).

$^1$H NMR (300 MHz, DMSO-d$_6$) δ ppm 6.03 (2H, s) 6.97-7.14 (2H, m) 7.15-7.33 (4H, m) 7.43-7.53 (1H, m) 7.56-7.64 (1H, m) 7.69 (1H, d, J=7.57 Hz) 8.25 (1H, br. s.) 8.38 (1H, s) 8.72 (2H, s) 9.67 (2H, br. s.) 10.83 (1H, br. s.).

Example 54

5-chloro-2-imino-1-[2-(phenylsulfonyl)benzyl]-1,2-dihydropyridine-3-carboxamide hydrochloride 2-Cyano-2-(3,4-dichloro-5-oxo-2,5-dihydrofuran-2-yl) acetamide (1.38 g), 1-[2-(phenylsulfonyl)phenyl]methanamine hydrochloride (2.0 g) and potassium carbonate (2.03 g) were stirred in ethanol (20 ml) at 90° C. for 20 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=4:1). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (0.64 g).

$^1$H NMR (300 MHz, DMSO-d$_6$) δ ppm 5.82 (2H, s) 7.08-7.20 (1H, m) 7.59-7.80 (5H, m) 8.01 (2H, d, J=7.16 Hz) 8.09-8.17 (1H, m) 8.24 (2H, d, J=1.88 Hz) 8.47-8.76 (2H, m) 9.56 (2H, br. s.).

Example 55

5-chloro-1-[5-chloro-2-(methylsulfonyl)benzyl]-2-imino-1,2-dihydropyridine-3-carboxamide 5-Chloro-1-[5-chloro-2-(methylsulfonyl)benzyl]-2-imino-1,2-dihydropyridine-3-carboxamide hydrochloride obtained in Example 1 (0.30 g) was dissolved in 1N aqueous sodium hydroxide solution, and the solution was extracted with ethyl acetate. The organic layer was washed with saturated brine, dried over magnesium sulfate, and filtered. The solvent was evaporated under reduced pressure. The precipitated crystals were collected by filtration to give the title compound (0.23 g).

$^1$H NMR (300 MHz, DMSO-d$_6$) δ ppm 3.49 (3H, s), 5.34 (2H, br. s.), 7.02 (1H, d, J=2.3 Hz), 7.41 (1H, br. s.), 7.50-7.76 (2H, m), 7.84-8.01 (3H, m), 8.06 (1H, d, J=1.5 Hz), 8.24 (1H, br. s.).

Example 56

5-chloro-1-[2-(cyclopropylsulfamoyl)benzyl]-2-imino-1,2-dihydropyridine-3-carboxamide hydrochloride 2-Cyano-2-(3,4-dichloro-5-oxo-2,5-dihydrofuran-2-yl) acetamide (1.49 g), 2-(aminomethyl)-N-cyclopropylbenzenesulfonamide hydrochloride (2.0 g) and potassium carbonate (2.19 g) were stirred in ethanol (30 ml) at 90° C. for 16 hr. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate). The obtained residue was dissolved in methanol, 4N hydrogen chloride-ethyl acetate solution (3 ml) was added, and the mixture was crystallized from methanol-ethyl acetate. The precipitated crystals were collected by filtration, and recrystallized to give the title compound (1.29 g).

$^1$H NMR (300 MHz, DMSO-d$_6$) δ ppm 0.24-0.65 (4H, m) 2.22 (1H, dt, J=6.72, 3.27 Hz) 5.87 (2H, d, J=7.57 Hz) 7.07 (1H, d, J=2.65 Hz) 7.53-7.75 (2H, m) 7.89-8.09 (1H, m) 8.24 (1H, br. s.) 8.42 (2H, br. s.) 8.70 (2H, br. s.) 9.56 (2H, br. s.).

Example 57

5-chloro-1-{5-chloro-2-[(methylcarbamoyl)amino]benzyl}-2-imino-1,2-dihydropyridine-3-carboxamide hydrochloride (Step 1) Using phenyl (4-chloro-2-cyanophenyl)carbamate obtained in Example 47, Steps 1 and 2N methylamine tetrahydrofuran solution, and in the same manner as in Example 47, Step 2, 1-(4-chloro-2-cyanophenyl)-3-methylurea was obtained.

$^1$H NMR (300 MHz, CDCl$_3$) δ ppm 2.90 (3H, d, J=4.9 Hz) 4.77-4.92 (1H, m) 6.75-6.85 (1H, m) 7.45-7.54 (2H, m) 8.27-8.37 (1H, m).

(Step 2) Using 1-(4-chloro-2-cyanophenyl)-3-methylurea obtained in Step 1, and in the same manner as in Example 43, Steps 2 and 3, 1-[2-(aminomethyl)-4-chlorophenyl]-3-methylurea hydrochloride was obtained.

$^1$H NMR (300 MHz, DMSO-d$_6$) δ ppm 2.66 (3H, s) 3.86-4.22 (2H, m) 6.61-6.90 (1H, m) 7.36 (1H, dd, J=2.6, 8.9 Hz) 7.51 (1H, d, J=2.6 Hz) 7.70 (1H, d, J=8.9 Hz) 8.28 (3H, br.s.) 8.74 (1H, s).

(Step 3) 2-Cyano-2-(3,4-dichloro-5-oxo-2,5-dihydrofuran-2-yl)acetamide (2.3 g), 1-[2-(aminomethyl)-4-chlorophenyl]-3-methylurea hydrochloride obtained in Step 2 (2.45 g) and diisopropylethylamine (5 ml) were stirred in ethanol (15 ml) overnight at 70° C. The reaction mixture was poured into 1N aqueous sodium hydroxide solution, and extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=7:3→1:0). The obtained residue was dissolved in ethanol, 4N hydrogen chloride-ethyl acetate solution (3 ml) was added, and the mixture was crystallized from ethanol-ethyl acetate. The precipitated crystals were collected by filtration, and recrystallized to give the title compound (0.52 g).

$^1$H NMR (300 MHz, DMSO-$d_6$) δ ppm 2.67 (3H, d, J=4.5 Hz) 5.36 (2H, s) 6.61-6.77 (1H, m) 6.87-7.02 (1H, m) 7.41 (1H, dd, J=2.3, 8.7 Hz) 7.57 (1H, d, J=9.0 Hz) 8.21 (1H, br.s.) 8.38-8.71 (4H, m) 9.27-9.78 (2H, m).

Example 58

5-chloro-1-[5-chloro-2-(propanoylamino)benzyl]-2-imino-1,2-dihydropyridine-3-carboxamide hydrochloride (Step 1) To a solution of 2-amino-5-chlorobenzonitrile (5.0 g) and dimethylaminopyridine (0.12 g) in dimethylacetamide (25 ml) was added propionyl chloride (3.4 ml) at room temperature, and the mixture was stirred overnight. The reaction mixture was poured into water, and extracted twice with ethyl acetate. The organic layer was washed with saturated brine, dried over magnesium sulfate, and filtered. The solvent was evaporated under reduced pressure. The residue was recrystallized from ethanol and diisopropyl ether to give N-(4-chloro-2-cyanophenyl)propanamide (5.7 g).

$^1$H NMR (300 MHz, DMSO-$d_6$) δ ppm 1.28 (3H, t, J=7.5 Hz) 2.50 (2H, q, J=7.5 Hz) 7.47-7.62 (3H, m).

(Step 2) Using N-(4-chloro-2-cyanophenyl)propanamide obtained in Step 1, and in the same manner as in Example 43, Steps 2 and 3, N-[2-(aminomethyl)-4-chlorophenyl]propanamide hydrochloride was obtained.

$^1$H NMR (300 MHz, DMSO-$d_6$) δ ppm 1.10 (2H, t, J=7.6 Hz) 2.40 (2H, q, J=7.6 Hz) 3.90-4.01 (2H, m) 7.40-7.48 (2H, m) 7.62 (1H, s) 8.33 (3H, br.s.) 9.90 (1H, s).

(Step 3) A solution of 2-cyano-2-(3,4-dichloro-5-oxo-2,5-dihydrofuran-2-yl)acetamide (1.88 g), N-[2-(aminomethyl)-4-chlorophenyl]propanamide hydrochloride obtained in Step 2 (1.99 g) and diisopropylethylamine (4.1 ml) in ethanol (15 ml) was stirred overnight at 70° C. The reaction solvent was evaporated under reduced pressure, the residue was dissolved in ethyl acetate and 1N sodium hydroxide, and the solution was extracted with ethyl acetate. The organic layer was washed with saturated brine, dried over magnesium sulfate, and filtered. The solvent was evaporated under reduced pressure. The residue was purified by basic silica gel column chromatography (ethyl acetate:hexane=7:3→1:0). The obtained residue was further purified by HPLC. The obtained residue was extracted with ethyl acetate and saturated sodium hydrogen carbonate. The organic layer was washed with saturated brine, dried over magnesium sulfate, and filtered. The solvent was evaporated under reduced pressure. The residue was dissolved in ethanol, and 4N hydrogen chloride-ethyl acetate solution was added. The precipitated crystals were collected by filtration, and recrystallized from ethanol and ethyl acetate to give the title compound (100 mg).

$^1$H NMR (300 MHz, DMSO-$d_6$) δ ppm 1.09 (3H, t, J=7.5 Hz) 2.39 (2H, q, J=7.3 Hz) 5.43 (2H, s) 7.12 (1H, d, J=2.3 Hz) 7.38-7.45 (1H, m) 7.46-7.53 (1H, m) 8.21 (1H, s) 8.54 (1H, br.s.) 8.59-8.72 (2H, m) 9.15-9.71 (2H, m) 9.94-10.13 (1H, m).

(Conditions of Preparative HPLC)
Purification by preparative HPLC was performed under the following conditions.
instrument: Gilson, Inc. high throughput purification system
column: YMC CombiPrep Hydrosphere C18 HS-340-CC, S-5 μM, 20×50 mm
solvent: SOLUTION A; 0.1% trifluoroacetic acid containing water, SOLUTION B; 0.1% trifluoroacetic acid containing acetonitrile
gradient cycle: 0.00 min (SOLUTION A/SOLUTION B=95/5), 1.10 min (SOLUTION A/SOLUTION B=95/5), 5.00 min (SOLUTION A/SOLUTION B=0/100), 6.40 min (SOLUTION A/SOLUTION B=0/100), 6.50 min (SOLUTION A/SOLUTION B=95/5)
flow rate: 20 ml/min
detection method: UV 220 nm Example 59

1-[3-(acetylamino)benzyl]-5-chloro-2-imino-1,2-dihydropyridine-3-carboxamide hydrochloride To a suspension of 2-cyano-2-(3,4-dichloro-5-oxo-2,5-dihydrofuran-2-yl)acetamide (0.70 g) and N-[3-(aminomethyl)phenyl]acetamide hydrochloride (1.20 g) in methanol (10 ml) was added triethylamine (1.66 ml) at room temperature, and the mixture was stirred overnight at 50° C. The reaction solvent was evaporated under reduced pressure, acetic acid (10 ml) was added, and the mixture was stirred at 50° C. for 2 hr. The solvent was evaporated under reduced pressure, ethyl acetate and saturated aqueous sodium hydrogen carbonate were added, and the aqueous layer was basified with 1N aqueous sodium hydroxide solution. The mixture was extracted with ethyl acetate, and the organic layer was dried over sodium sulfate. The solvent was evaporated under reduced pressure. The residue was purified by basic silica gel column chromatography (ethyl acetate:hexane=7:3→1:0). The obtained residue was dissolved in methanol, 4N hydrogen chloride-ethyl acetate solution (1 ml) was added, and the mixture was crystallized from methanol-ethyl acetate. The precipitated crystals were collected by filtration, and recrystallized from methanol-ethyl acetate to give the title compound (0.30 g).

$^1$H NMR (300 MHz, DMSO-$d_6$) δ ppm 2.03 (3H, s), 5.54 (2H, s), 6.92 (1H, d, J=7.6 Hz), 7.33 (1H, t, J=8.0 Hz), 7.44-7.50 (1H, m), 7.54 (1H, d, J=8.3 Hz), 8.21 (1H, s), 8.57-8.71 (2H, m), 8.76 (1H, d, J=2.3 Hz), 9.43 (2H, br. s.), 10.09 (1H, s).

The structural formulas of the compounds of Examples are shown in Tables 1 to 3.

TABLE 1

Example 1

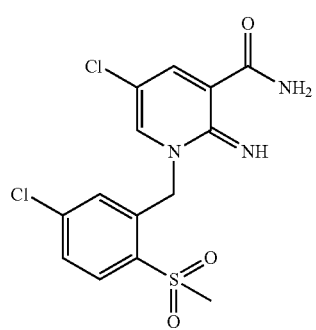

HCl
Example 2

TABLE 1-continued
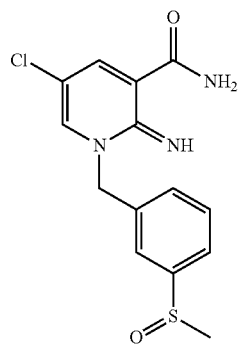
HCl
Example 3
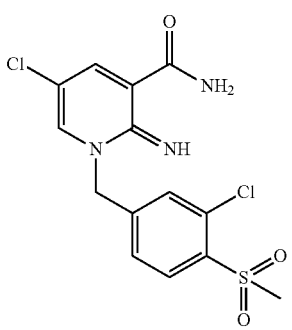
HCl
Example 4
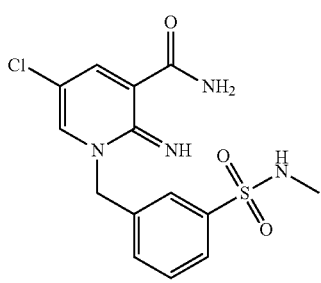
HCl
Example 5
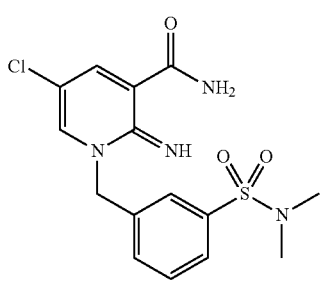
HCl
Example 6
TABLE 1-continued
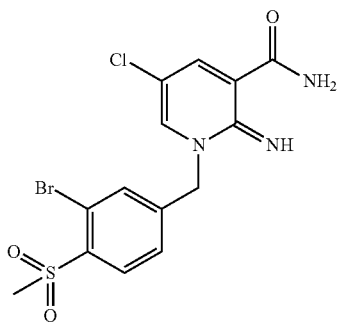
HCl
Example 7
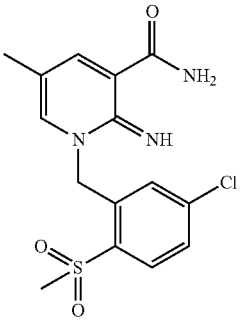
HCl
Example 8
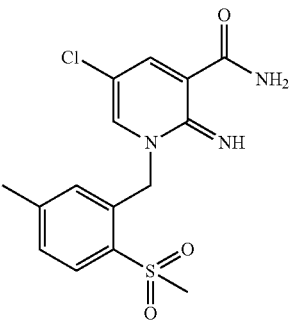
HCl
Example 9
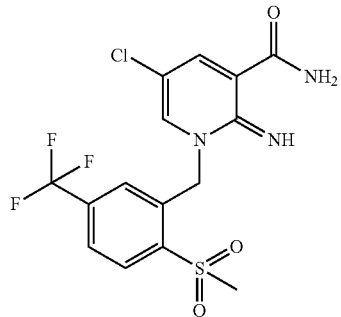
HCl
Example 10

TABLE 1-continued
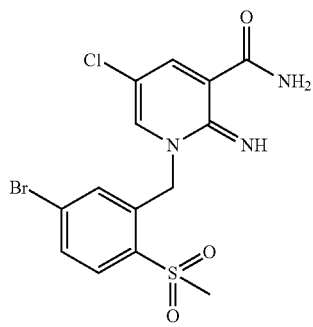
HCl
Example 11
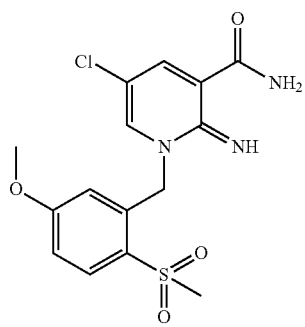
HCl
Example 12
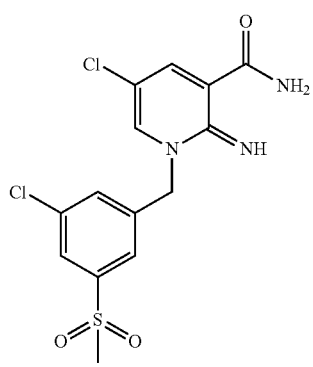
HCl
Example 13
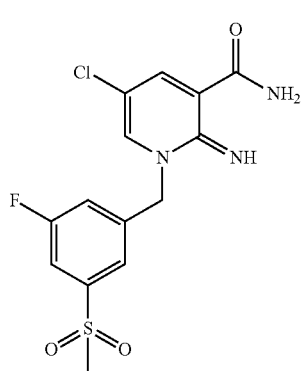
HCl
Example 14
TABLE 1-continued
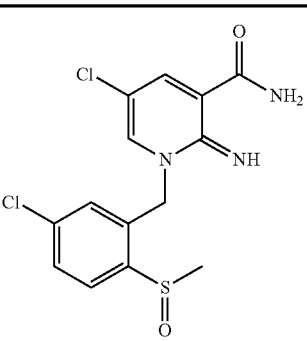
HCl
Example 15
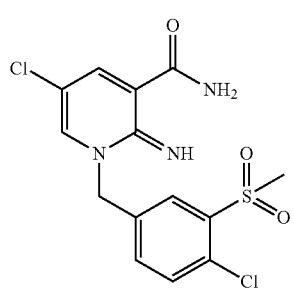
HCl
Example 16
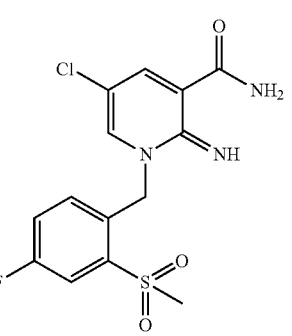
HCl
Example 17
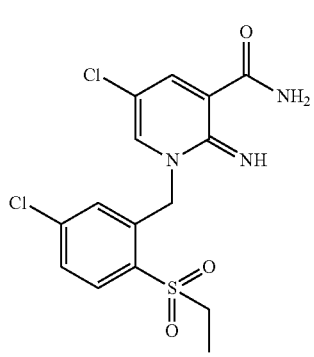
HCl
Example 18

TABLE 1-continued
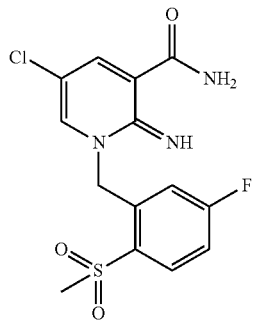
HCl
Example 19
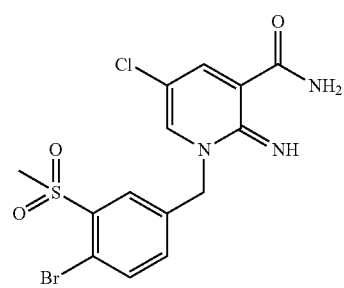
HCl
Example 20
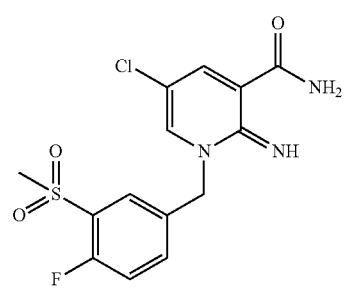
HCl
TABLE 2
Example 21
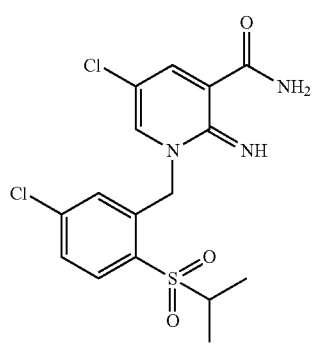
HCl
Example 22
TABLE 2-continued
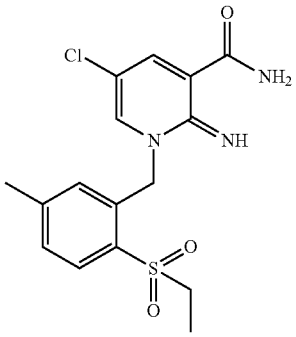
HCl
Example 23
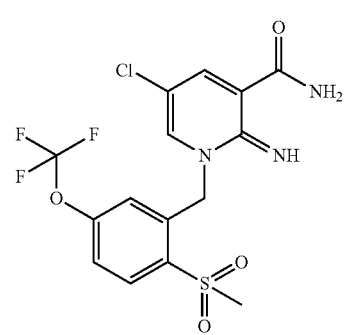
HCl
Example 24
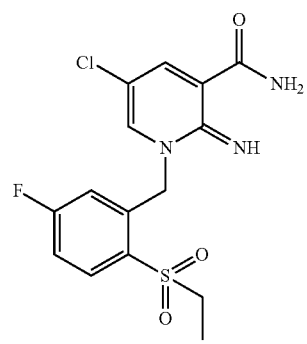
HCl
Example 25
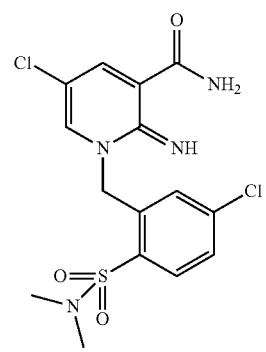
HCl
Example 26

TABLE 2-continued
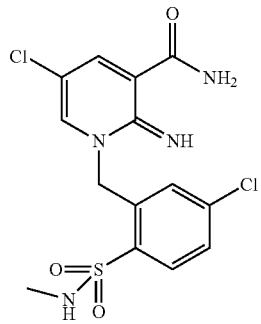
HCl
Example 27
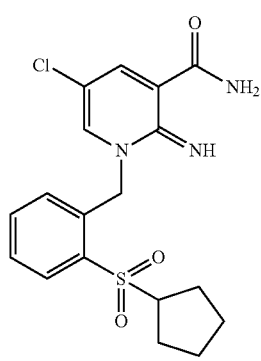
HCl
Example 28
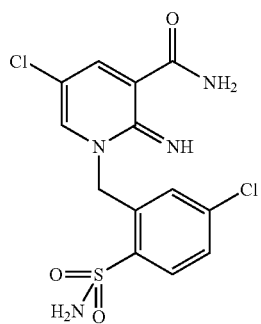
HCl
Example 29
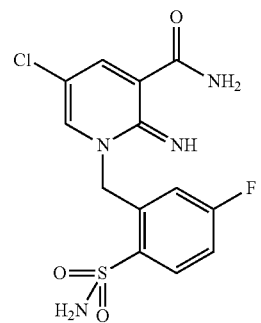
HCl
Example 30
TABLE 2-continued
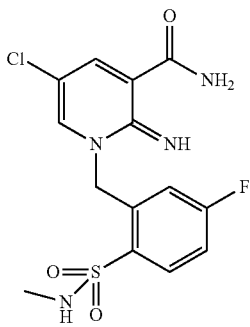
HCl
Example 31
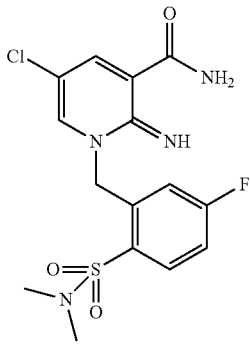
HCl
Example 32
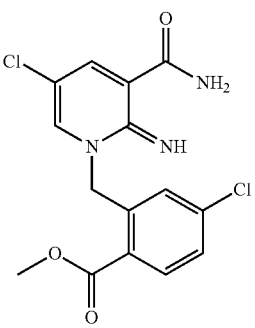
HBr
Example 33
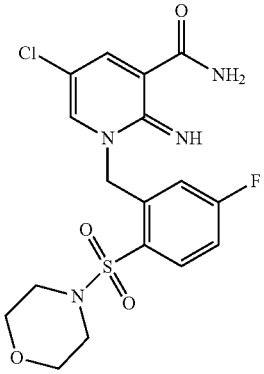
HCl
Example 34

TABLE 2-continued
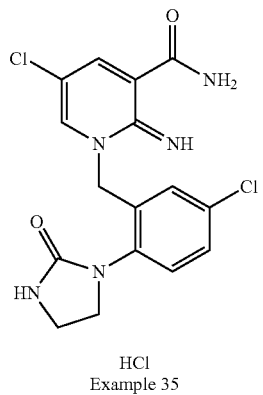
HCl
Example 35
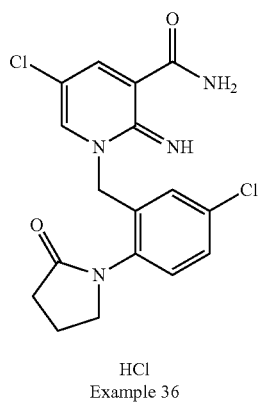
HCl
Example 36
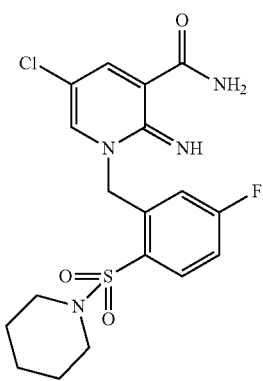
HCl
Example 37
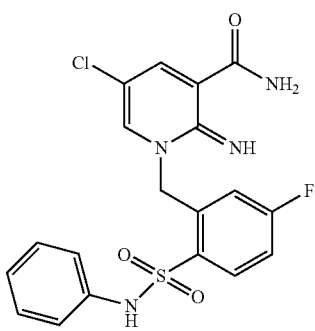
HCl
Example 38
TABLE 2-continued
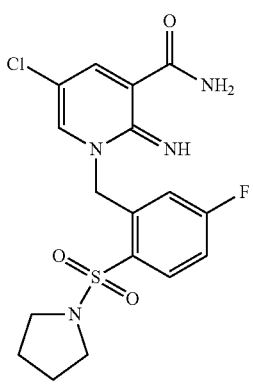
HCl
Example 39
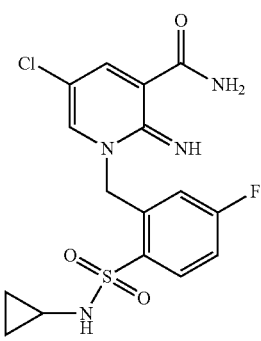
HCl
Example 40
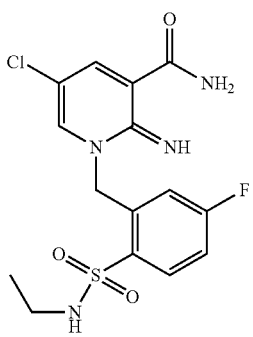
HCl TABLE 3
Example 41
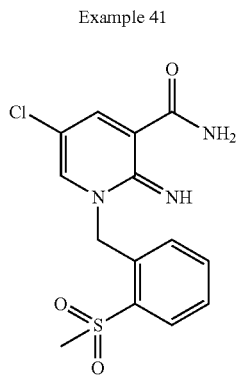
HCl
Example 42
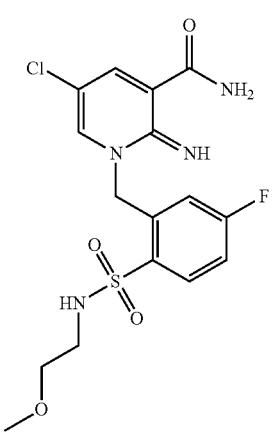
HCl
Example 43
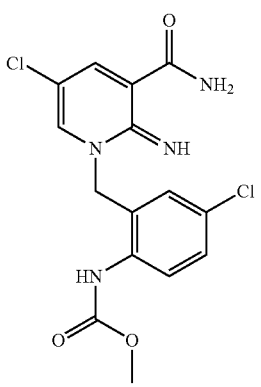
HCl
Example 44
TABLE 3-continued
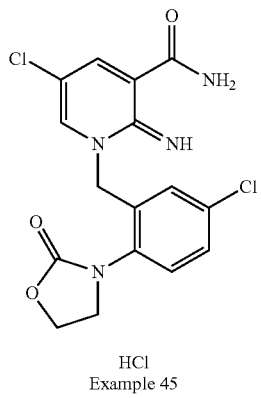
HCl
Example 45
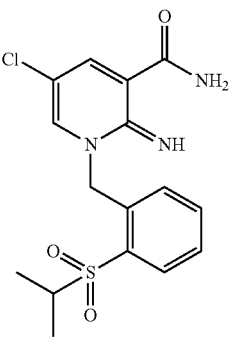
HCl
Example 46
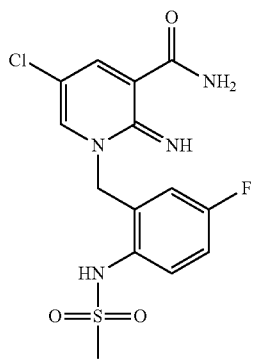
409.26 HCl
Example 47
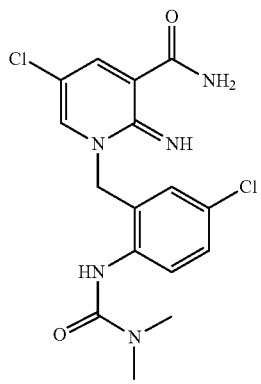
418.71 HCl
Example 48

TABLE 3-continued
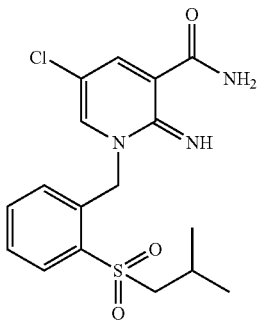
418.34 HCl
Example 49
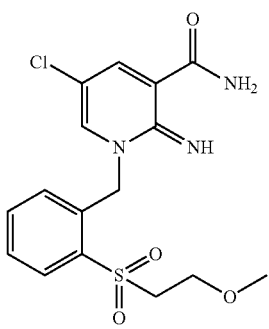
420.31 HCl
Example 50
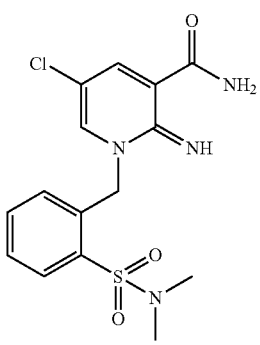
405.30 HCl
Example 51
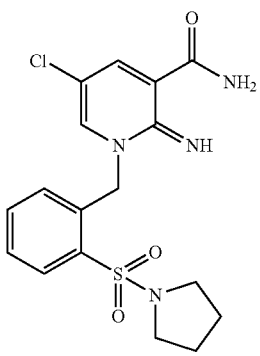
HCl
Example 52
TABLE 3-continued
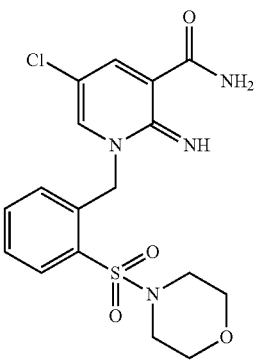
HCl
Example 53
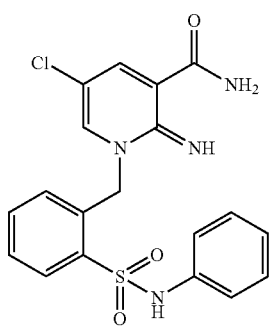
HCl
Example 54
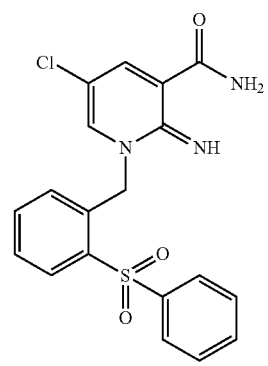
HCl
Example 55
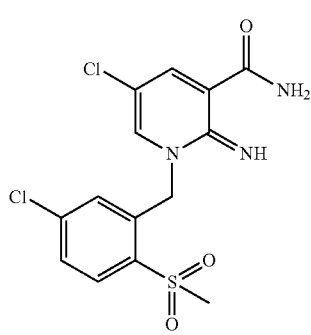
Example 56

TABLE 3-continued

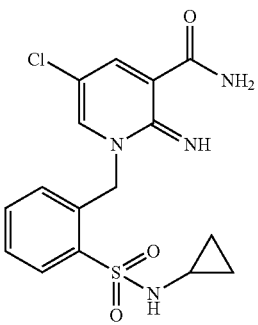

HCl
Example 57

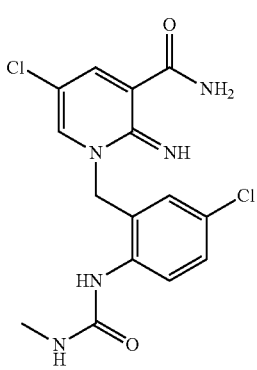

HCl
Example 58

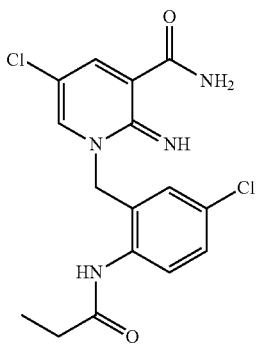

HCl
Example 59

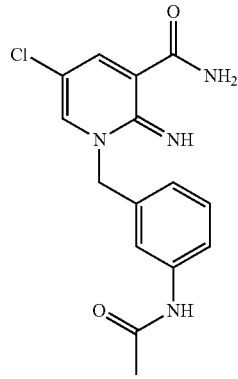

HCl

Experimental Example 1

Measurement of $\alpha_{1D}$ Adrenaline Receptor Binding Inhibitory Activity Genetic manipulation methods described below are based on the methods described in Maniatis et al., Molecular Cloning, Cold Spring Harbor Laboratory, 1989, the protocol appended to a reagent and the like.

(i) Preparation of Human $\alpha_{1D}$ Adrenaline Receptor Expression Plasmid $\alpha_{1D}$ Adrenaline receptor gene was cloned from human liver cDNA by the PCR method. PCR reaction was performed by Gene Amp PCR System 9700 (Applied Biosystems) with 50 pmol each of the primer set 5'-CCGACGGCCGCTAGC-GAGATGACTTTCCGCGATCTCCTGAGCGTC-3'[SEQ ID NO: 1] and 5'-GCTCTGGGTACCTTAAATATCG-GTCTCCCGTAGGTTGC-3' [SEQ ID NO: 2] prepared in reference to the base sequence of the $\alpha_{1D}$ adrenaline receptor gene reported by DEBRA A. et al. (J. Pharamacol. Exp. Ter., 272, 134-142 (1995)), 200 ng of human brain hippocampus cDNA library (Takara Shuzo Co., Ltd.) as a template and TaKaRa LA-Taq DNA Polymerase (Takara Shuzo Co., Ltd.) (reaction conditions: 45 cycles of 94° C. for 15 sec, 68° C. for 3.5 min).

The PCR fragment obtained above was digested with restriction enzymes NheI (Takara Shuzo Co., Ltd.) and Kpn I (Takara Shuzo Co., Ltd.), and applied to agarose gel electrophoresis to recover DNA fragments. The DNA fragments were ligated with animal cell expression plasmid pcDNA3.1/Zeo (Invitrogen) digested with NheI and Kpn I, by DNA Ligation Kit Ver. 2 (Takara Shuzo Co., Ltd.), and transformed the competent cells of *Escherichia coli* JM109 to obtain plasmid, pcDNA3.1/Zeo-Adre$\alpha_{1D}$.

(ii) Introduction of Human $\alpha_{1D}$ Adrenaline Receptor Expression Plasmid into CHO-K1 Cells and Preparation of Membrane Fraction CHO-K1 cells passage cultured in HamF12 medium (Invitrogen) containing 10% fetal bovine serum (TRACE SCIENCETIFIC) in a 150 cm² culture flask (Corning Coaster) were detached with 0.5 g/L trypsin-0.2 g/L EDTA (Invitrogen), and the cells were washed with D-PBS(-) (Invitrogen) and centrifuged (1000 rpm, 5 min). Then, using Gene Pulser II (BioRad), DNA was introduced into the cells under the following conditions. 1×10⁷ cells suspended in D-PBS(-) (700 μl) and 10 μg of pcDNA3.1/Zeo-Adre$\alpha_{1D}$ were added in a 0.4 cm gap cuvette (BioRad), and electroporation was performed under voltage 0.25 kV, capacitance 960 μF. The cells were cultured in HamF12 medium containing 10% fetal bovine serum and 250 μg/mL Zeocin (Invitrogen) and the Zeocin resistance clones were selected.

Plurality of Zeocin resistance clones were selected and cultured in a cell culture flask (150 cm²) until semiconfluent, and the cellular membrane fraction was prepared as follows.

The semiconfluent cells were detached with 0.02% EDTA containing D-PBS(-) and recovered by centrifugation. The cells were suspended in membrane preparation buffer (10 mM NaHCO₃ pH 7.4, protease inhibitor cocktail (Roche)) and disrupted by 3 times of treatment in a polytron homogenizer (model PT-3100, KINEMATICA AG) at 20000 rpm for 20 seconds. After disruption, the cells were centrifuged at 2000 rpm for 10 min and the supernatant containing membrane fractions was obtained. The supernatant was centrifuged using an ultracentrifuge (model L8-70M, rotor 70 Ti, Beckman Instruments) at 30000 rpm for 1 hr to obtain a precipitate containing membrane fractions. The obtained membrane fraction of each clone was subjected to the binding experiment shown below.

The membrane fraction (20 μg/well) and [$^3$H] prazosin (2.5 nM, PerkinElmer Lifescience), as a ligand, were diluted with a binding assay buffer (50 mM Tris-HCl, 10 mM MgCl$_2$, 0.5% BSA, protease inhibitor cocktail pH 7.5), added to a 96 well microplate, and reacted at room temperature for 1 hr. For the measurement of non-specific binding, phentolamine (Sigma) was further added to 10 μM. Then, the reaction mixture was filtered and transferred to unifilter GF/C (PerkinElmer Lifescience) by using a cell harvester (PerkinElmer Lifescience). The filter was washed 3 times with ice-cooled 50 mM Tris buffer (pH 7.5). After drying the filter, MicroScinti 0 (PerkinElmer Lifescience) was added to the filter and the radioactivity was measured by TopCount (PerkinElmer Lifescience). Membrane fractions for compound evaluation shown below were prepared by a method similar to the above-mentioned method from the clones that showed the most superior S/B value (total binding radioactivity/non-specific binding radioactivity) in the binding measurement using the membrane fractions.

(iii) Evaluation of Example Compound

The membrane fraction (10 μg/well), the compound and prazosin (2.5 nM, PerkinElmer Lifescience) were diluted with a compound binding assay buffer (50 mM Tris-HCl, 10 mM MgCl$_2$, 5 mM EDTA, 0.5% BSA, pH 7.5), added to a 96 well microplate, and the mixture was reacted at room temperature for 1 hr. For the measurement of non-specific binding, phentolamine (Sigma), which is a cold ligand, was further added to 10 μM. Then, the reaction mixture was filtered and transferred to unifilter GF/C (PerkinElmer Lifescience) by using a cell harvester (PerkinElmer Lifescience). The filter was washed 3 times with cooled 50 mM Tris buffer (pH 7.5). After drying the filter, MicroScinti 0 (PerkinElmer Lifescience) was added to the filter and the radioactivity was measured by TopCount (PerkinElmer Lifescience).

The concentration of the compound necessary for decreasing the amount of binding of [$^3$H]-prazosin to the membrane fraction to 50% (IC$_{50}$) was calculated by GlaphPad Prism Ver3.2 (GlaphPad Software).

The results measured by the above-mentioned method ($\alpha_{1D}$ adrenaline receptor binding inhibitory rate at 1 μM) are shown in Table 4.

TABLE 4

| test compound (Example No.) | binding inhibitory rate (%) |
|---|---|
| 1 | 100.0 |
| 8 | 93.5 |
| 12 | 87.5 |
| 14 | 92.0 |
| 15 | 72.8 |

TABLE 4-continued

| test compound (Example No.) | binding inhibitory rate (%) |
|---|---|
| 17 | 100.0 |
| 18 | 93.5 |
| 24 | 98.4 |
| 28 | 91.2 |
| 35 | 89.0 |

Formulation Example 1

| | |
|---|---|
| (1) compound of Example 1 | 10 mg |
| (2) lactose | 60 mg |
| (3) cornstarch | 35 mg |
| (4) hydroxypropylmethylcellulose | 3 mg |
| (5) magnesium stearate | 2 mg |

A mixture of the compound (10 mg) obtained in Example 1, lactose (60 mg) and cornstarch (35 mg) is granulated using 10 wt % aqueous hydroxypropylmethylcellulose solution (0.03 mL, 3 mg as hydroxypropylmethylcellulose), dried at 40° C. and passed through a sieve. The obtained granules are mixed with magnesium stearate (2 mg), and the mixture is compressed. The obtained core tablet is coated with a sugar coating of a suspension of saccharose, titanium dioxide, talc and gum arabic in water. The coated tablet is polished with beeswax to give a coated tablet.

Formulation Example 2

| | |
|---|---|
| (1) compound of Example 1 | 10 mg |
| (2) lactose | 70 mg |
| (3) cornstarch | 50 mg |
| (4) soluble starch | 7 mg |
| (5) magnesium stearate | 3 mg |

The compound (10 mg) obtained in Example 1 and magnesium stearate (3 mg) are granulated with an aqueous soluble starch solution (0.07 mL, 7 mg as soluble starch), dried, and mixed with lactose (70 mg) and cornstarch (50 mg). The mixture is compressed to give a tablet.

INDUSTRIAL APPLICABILITY

The compound of the present invention has a superior selective $\alpha_{1D}$ adrenaline receptor antagonistic action, and is useful as an agent for the prophylaxis or treatment of a lower urinary tract disease and the like.

This application is based on patent application No. 113135/2008 filed in Japan, the contents of which are hereby incorporated by reference.

The invention claimed is:
1. 5-Chloro-1-[5-chloro-2-(methylsulfonyl)benzyl]-2-imino-1,2-dihydropyridine-3-carboxamide or a salt thereof.

* * * * *

UNITED STATES PATENT AND TRADEMARK OFFICE
CERTIFICATE OF CORRECTION

PATENT NO. : 7,982,044 B2
APPLICATION NO. : 13/022563
DATED : July 19, 2011
INVENTOR(S) : Masato Yoshida, Nobuki Sakauchi and Ayumu Sato It is certified that error appears in the above-identified patent and that said Letters Patent is hereby corrected as shown below:

Column 1, line 18, "contends" should be -- contents --;

Column 16, line 37, "acid and the like, and the like, for" should be -- acid and the like, for --;

Column 17, line 22, "piperazine and the like, and the like." should be -- piperazine and the like. --;

Column 24, lines 39-40, "and the like) and the like." should be -- and the like). --;

Column 24, lines 48-49, "and the like, and the like, nitro," should be -- and the like, nitro, --;

Column 24, line 57, "and the like, and the like," should be -- and the like, --;

Column 24, line 60, "and the like, and the like)," should be -- and the like), --;

Column 25, line 4, "hexyl and the like, and the like)," should be -- hexyl and the like), --;

Column 25, line 6, "2-hexynyl and the like, and the like)," should be -- 2-hexynyl and the like), --;

Column 25, line 8, "3-hexynyl and the like, and the like)," should be -- 3-hexynyl and the like), --;

Column 25, line 10, "and the like, and the like)," should be -- and the like), --;

Column 25, line 23, "and the like) and the like, and the like]," should be -- and the like) and the like], --;

Column 25, line 27, "and the like, and the like)." should be -- and the like). --;

Column 35, line 6, "hydride and the like, and the like." should be -- hydride and the like). --;

Column 35, line 52, "hydride and the like; and the like." should be -- hydride and the like. --;

Column 36, line 46, "acetic acid and the like, and the like." should be -- acetic acid and the like. --;

Column 39, line 42, "potassium hydride and the like, and the like." should be -- potassium hydride and the like. --;

Column 40, lines 17-18, "potassium hydride and the like, and the like." should be -- potassium hydride and the like. --;

Column 41, line 5, "potassium hydride and the like, and the like." should be -- potassium hydride and the like. --;

Signed and Sealed this
Seventh Day of February, 2012

David J. Kappos
*Director of the United States Patent and Trademark Office*

Column 41, line 8, "acid and the like, and the like." should be -- acid and the like. --;

Column 44, lines 20-21, "an optical method and the like can also be mentioned." should be -- an optical method and the like. --;

Column 48, line 30, "ray•infrared ray•laser ray, altitude sickness etc.)," should be -- ray, infrared ray or laser ray, altitude sickness etc.), --;

Column 53, line 53, "causes no problems of side effects." should be -- causes no side effects. --; and Column 57, lines 4-5, "ride obtained in
   Step 3 (0.26 g) in ethanol (3 ml) was added N,N-diisopro-" should be -- ride obtained in
Step 3 (0.26 g) in ethanol (3 ml) was added N,N-diisopro- --.

UNITED STATES PATENT AND TRADEMARK OFFICE
CERTIFICATE OF CORRECTION

PATENT NO. : 7,982,044 B2
APPLICATION NO. : 13/022563
DATED : July 19, 2011
INVENTOR(S) : Masato Yoshida and Nobuki Sakauchi It is certified that error appears in the above-identified patent and that said Letters Patent is hereby corrected as shown below:

Column 1, line 18, "contends" should be -- contents --;

Column 16, line 37, "acid and the like, and the like, for" should be -- acid and the like, for --;

Column 17, line 22, "piperazine and the like, and the like." should be -- piperazine and the like. --;

Column 24, lines 39-40, "and the like) and the like." should be -- and the like). --;

Column 24, lines 48-49, "and the like, and the like, nitro," should be -- and the like, nitro, --;

Column 24, line 57, "and the like, and the like," should be -- and the like, --;

Column 24, line 60, "and the like, and the like)," should be -- and the like), --;

Column 25, line 4, "hexyl and the like, and the like)," should be -- hexyl and the like), --;

Column 25, line 6, "2-hexynyl and the like, and the like)," should be -- 2-hexynyl and the like), --;

Column 25, line 8, "3-hexynyl and the like, and the like)," should be -- 3-hexynyl and the like), --;

Column 25, line 10, "and the like, and the like)," should be -- and the like), --;

Column 25, line 23, "and the like) and the like, and the like]," should be -- and the like) and the like], --;

Column 25, line 27, "and the like, and the like)." should be -- and the like). --;

Column 35, line 6, "hydride and the like, and the like." should be -- hydride and the like). --;

Column 35, line 52, "hydride and the like; and the like." should be -- hydride and the like. --;

Column 36, line 46, "acetic acid and the like, and the like." should be -- acetic acid and the like. --;

Column 39, line 42, "potassium hydride and the like, and the like." should be -- potassium hydride and the like. --;

Column 40, lines 17-18, "potassium hydride and the like, and the like." should be -- potassium hydride and the like. --;

This certificate supersedes the Certificate of Correction issued February 7, 2012.

Signed and Sealed this
Twentieth Day of November, 2012

David J. Kappos
*Director of the United States Patent and Trademark Office*

CERTIFICATE OF CORRECTION (continued)
U.S. Pat. No. 7,982,044 B2

Column 41, line 5, "potassium hydride and the like, and the like." should be -- potassium hydride and the like. --;

Column 41, line 8, "acid and the like, and the like." should be -- acid and the like. --;

Column 44, lines 20-21, "an optical method and the like can also be mentioned." should be -- an optical method and the like. --;

Column 48, line 30, "ray•infrared ray•laser ray, altitude sickness etc.)," should be -- ray, infrared ray or laser ray, altitude sickness etc.), --;

Column 53, line 53, "causes no problems of side effects." should be -- causes no side effects. --; and Column 57, lines 4-5, "ride obtained in
   Step 3 (0.26 g) in ethanol (3 ml) was added N,N-diisopro-" should be -- ride obtained in
Step 3 (0.26 g) in ethanol (3 ml) was added N,N-diisopro- --.